United States Patent [19]
Holt et al.

[11] Patent Number: 5,891,857
[45] Date of Patent: Apr. 6, 1999

[54] CHARACTERIZED BRCA1 AND BRCA2 PROTEINS AND SCREENING AND THERAPEUTIC METHODS BASED ON CHARACTERIZED BRCA1 AND BRCA2 PROTEINS

[75] Inventors: Jeffrey T. Holt, Brentwood; Roy A. Jensen, Franklin, both of Tenn.; Mary-Claire King, Seattle, Wash.; David L. Page, Nashville, Tenn.; Csilla I. Szabo, Seattle, Wash.; Thomas L. Jetton, Kingston Springs, Tenn.; Cheryl L. Robinson-Benion; Marilyn E. Thompson, both of Nashville, Tenn.

[73] Assignees: Vanderbilt University, Nashville, Tenn.; University of Washington, Seattle, Wash.

[21] Appl. No.: 603,753

[22] Filed: Feb. 20, 1996

[51] Int. Cl.$^6$ ..................................... A61K 48/00
[52] U.S. Cl. ........................... 514/44; 514/44; 435/173.3; 435/325; 435/69.1; 435/172.3; 424/93.21; 536/23.1
[58] Field of Search ............................. 514/44; 435/173.3, 435/240.2, 320.1, 69.1, 172.3, 325; 935/33, 23, 32, 55, 57; 424/93.21; 536/70, 71, 23.1

[56] References Cited

U.S. PATENT DOCUMENTS 5,399,346   3/1995   Anderson et al. .................... 424/93.21

FOREIGN PATENT DOCUMENTS

| | | |
|---|---|---|
| 0 699 754 A1 | 3/1996 | European Pat. Off. . |
| 0 705 902 A1 | 4/1996 | European Pat. Off. . |
| 0 705 903 A1 | 4/1996 | European Pat. Off. . |
| WO 95/19369 | 7/1995 | WIPO . |
| WO 95/25429 | 9/1995 | WIPO . |
| WO 95/25813 | 9/1995 | WIPO . |
| WO 96/05306 | 2/1996 | WIPO . |
| WO 96/05307 | 2/1996 | WIPO . |
| WO 96/05308 | 2/1996 | WIPO . |

OTHER PUBLICATIONS

Wallace et al. Methods in Enzymology 1987, 152:432, Jan. 27, 1996.
Sambrook et al. Molecular Cloning 1989, CSH:11.47, Jan. 27, 1996.
Reek et al. Cell 1987, vol. 50:667, Jan. 27, 1997.
Gunzburg et al. Mol. Med. Today 1995:410–417 vol. 11, No. 9, pp. 410–417, 1995, Jan. 27, 1997.
Coghlan. New Scientist, Nov. 1995, vol. 148, pp. 14–15, Jan. 27, 1997.
Marshall. Science Dec. 1995:1751, Jan. 27, 1997.

(List continued on next page.)

*Primary Examiner*—Christopher S. F. Low
*Assistant Examiner*—Dave Trong Nguyen
*Attorney, Agent, or Firm*—Jenkins & Wilson, P.A.

[57] ABSTRACT

Genetic analysis of familial breast and ovarian cancer indicates that BRCA1 is a tumor suppressor gene. The BRCA1 gene encodes a 190 kDa protein with sequence homology and biochemical analogy to the granin family of proteins. Granins are secreted from endocrine cells via the regulated secretory pathway and are proteolytically cleaved to yield biologically active peptides. BRCA1 protein localizes to secretory vesicles, and was demonstrated to be secreted. Gene transfer of BRCA1 inhibits growth and tumorigenesis of breast and ovarian cancer cells, but not colon or lung cancer cells or fibroblasts, suggesting that BRCA1 encodes a tissue-specific growth inhibitor. Thus, BRCA1 is a secreted growth inhibitor and functions by a mechanism not previously described for tumor suppressor genes. The BRCA2 breast and ovarian cancer gene encodes a protein that also includes a granin region, indicating that the BRCA2 protein is also a secreted tumor suppressor. Therapeutic methods using the BRCA1 and BRCA proteins and genes are also described. A method of screening for the receptors of the BRCA1 protein and BRCA2 proteins is also described.

2 Claims, 28 Drawing Sheets

BRCA1 Antigens

C-19 (19 C-terminal amino acids): [Seq ID No: 5]
    Tyr Gln Cys Gln Glu Leu Asp Thr Tyr Leu Ile Pro Gln Ile Pro His Ser His Tyr C-20 (20 C-terminal amino acids): [Seq ID No: 6]
    Leu Tyr Gln Cys Gln Glu Leu Asp Thr Tyr Leu Ile Pro Gln Ile Pro His Ser His Tyr D-20 ( 20 N-terminal amino acids): [Seq ID No: 7]
    Met Asp Leu Ser Ala Leu Arg Val Glu Glu Val Gln Asn Val Ile Asn Ala Met Gln Lys

OTHER PUBLICATIONS

Ledley. Human Gene Therapy 1995, 6:1129–1144, Jan. 27, 1997.

Mastrangelo et al. Seminars in Oncology, vol. 23, No. 1:4–21, 1996, Jan. 27, 1997.

Jain et al. Scientific America, 271 (1):58–63, 1994, Jan. 27, 1997.

Carol Ezzell, News, BRCA1 Shock; Breast Cancer Gene Encodes a Secreted Protein, The Journal of NIH Research, vol. 8, pp. 21–22 (Mar. 1996).

Takahashi, H., "Mutation analysis of the BRCA1 gene in ovarian cancers," *Cancer Res.* 55: 2998–3002 (1995).

Burtness, B.A., "Oncology and Hematology," *JAMA* 273:1702–1703 (1995).

Weber et al., "Familial Breast Cancer–Approaching the Isolation of a Susceptibility Gene," *Cancer* (Supp.) 74:1013–20 (1994).

Norris et al., "Identification of a New Subclass of Ala DNA Repeats Which Can Function as Estrogen Receptor–dependent Transcriptional Enhancers," *Journal of Biological Chemistry* 39:22, 777–82 (1995).

Steeg, P., "Granin expectations in breast cancer?," *Nature Genetics* 12:223–25 (1996).

Lemoine, N.R., "Molecular biology of Breast Cancer," *Annals of Oncology* 5 (Supp. 4):S31–S37 (1994).

Easton et al., "Inherited Susceptibility to Breast Cancer," *Cancer Surveys* 18:95–113 (1993).

Narod, S. A., "Genetics of breast and ovarian cancer," *British Medical Bulletin* 50:656–76 (1994).

Hopkin, K., "MTSI, Telomerase May Be New Target For Cancer Therapy," *The Journal of NIH Research* 6:38–42 (1994).

Hall et al., "Linkage of Early Onset–Familial Breast Cancer to Chromososme 17q21," *Science* 250: 1684–89 (1990).

Helzouer et al., "Epidemiology, prevention, and early detection of breast cancer," *Current Opinion in Oncology* 7:489–95 (1995).

Szabo et al., "Inherited breast and ovarian cancer," *Human Molecular Genetics* 4:1811–17 (1995).

U.S. Ser. No. 289,221, filed Aug. 12, 1994.
U.S. Ser. No. 289,221, filed Aug. 12, 1994.
U.S. Ser. No. 308,104, filed Sep. 16, 1994.
U.S. Ser. No. 348,824, filed Nov. 29, 1994.
U.S. Ser. No. 409,305, filed Mar. 24, 1995.
U.S. Ser. No. 480,784, filed Jun. 7, 1995.
U.S. Ser. No. 483,553, filed Jun. 7, 1995.
U.S. Ser. No. 483,554 filed Jun. 7, 1995.
U.S. Ser. No. 488,011 filed Jun. 7, 1995.
U.S. Ser. No. 487,002 filed Jun. 7, 1995.

Yoshio, Miki, Jeff Swensen, Donna Shattuck–Eidens, P. Andrew Futreal, Keith Harshman, Sean Tavtigian, Qinhyun Liu, Charles Cochran, L. Michelle Bennett, Wei Ding, Russell Bell, Judith Rosenthal, Charles Hussey, Thanh Tran, Melody McClure, Cheryl Frye, Tom Hattier, Robert Phelps, Astrid Haugen–Strano, Harold Katcher, Kazuko Yakumo, Zahra Gholami, Daniel Shaffer, Steven Stone, Steven Bayer, Christian Wray, Robert Bogden, Priya Dayananth, John Ward, Patricia Tonin, Steven Narod, Pam K. Bristow, Frank H. Norris, Leah Helvering, Paul Morrison, Paul Rosteck, mei Lai, J. Carl Barrett, Cathryn Lewis, Susan Neuhausen, Lisa Cannon–Albright, David Foldgar, Roger Wiseman, Alexander Kamb, and Mark J. Skolnick, A Strong Candidate for the Breast and Ovarian Cancer Susceptibility Gene BRCA1, *Science*, vol. 266, pp. 66–71 (7 Oct. 1994).

Steven A. Narod, Deborah Ford, Peter Devilee, Rosa B. Barkardottir, Henry T. Lynch, Simon A. Smith, Bruce A.J. Ponder Barbara L. Weber, Judy E. Garber, Jill M. Birch, Renee S. cornelis, David P. Kelsell, Nigel K. Spurr, Elizabeth Smyth, Neva Haites, Hagay Sobol, Yves–jean Bignon, Jenny Chang–Claude, Ute Hamann, Annika Lindblom, Ake Brog, M. Steven Piver, Holly H. Gallion, Jeffrey P. Struewing, Alice Whittemore, Patricia Tonin, David E. Goldgar, Douglas F. Easton, and the Breast Cancer Linkage Consortium, An Evaluation of Genetic Heterogeneity in 145 Breast–Ovarian Cancer Families, *Am.J.Hum.Genet.*, 56:254–264 (1995).

Ian G. Campbell, Hans M. Nicolai, William D. Foulkes, Gabriel Senger, Gordon W. Stamp, Gordon Allan, Cinda Boyer, Karen Jones, Robert C. Bast, Jr., Ellen Solomon, John Trowsdale and Donald M. Black, A Novel Gene Encoding a B–Box Protein Within the BRCA1 Region at 17q21.1, *Human Molecular Genetics*, vol. 3, No. 4, pp. 589–594 (1994).

Joseph N. Marcus, Patrice Watson, David L. Page, and Henry T. Lynch, Pathology and Heredity of Breast Cancer in Younger Women, *Journal of the National Cancer Institute Monographs*, No. 16, pp. 23–33 (1994).

D.E. Porter, B.B. Cohen, M.R. Wallace, E. Smyth, U. Chetty, J.M. Dixon, C.M. Steel, and D.C. Carter, Breast Cancer Incidence, Penetrance and Survival in Probable Carriers of BRCA1 Gene Mutation in Families Linked to BRCA1 on Chromosome 17q12–21, *British Journal of Surgery*, 81, pp. 1512–1515 (1994).

Giorgio R. Merlo, Tiziana Venesio, Amelia Bernardi, Craig S. Cropp, Francesca Diella, Alberto P.M. Cappa, Robert Callahan, and Daniel S. Liscia, Evidence for a Second Tumor Suppressor Gene on 17p Linked to High S–Phase Index in Primary Human Breast Carcinomas, *Cancer Genet Cytogenet*, 76:106–111(1994).

Susan L. Neuhausen and C. Jay Marshall, Loss of Heterozygosity in Familial Tumors from Three BRCA1–linked Kindreds, *Cancer Research*, 54, pp. 6069–6072 (1994).

Melissa Brown, Hans Nicolai, Chun–Fang Xu, Beatrice L. Griffiths, Karen A. Jones, Ellen Solomon, Louise Hosking, John Trowsdale, Donald M. Black, and Robert McFarlane, Regulation of BRCA1, *Nature*, vol. 372, p. 733 (1994).

J. Simard, P. Tonin, F. Durocher, K. Morgan, J. Rommens, S. Gingras, C. Samson, J.–F. Leblanc, C. Belanger, F. Dion, Q. Liu, M. Skolnick, D. Goldgar, D. Shattuck–Eidens, F. Labrie & S.A. Narod, Common Origins of BRCA1 Mutations in Canadian Breast and Ovarian Cancer Families *Nature Genetics*, vol. 8, pp. 392–398 (1994).

Lori S. Friedman, Elizabeth A. Ostermeyer, Csilla I. Szabo, Patrick Dowd, Eric D. Lynch, Sarah E. Rowell & Mary–Claire King, Confirmation of BRCA1 by Analysis of Germline Mutations Linked to Breast and Ovarian Cancer in Ten Families, *Nature Genetics*, pp. 1–6.

Lucio H. Castilla, Fergus J. Couch, Michael R. Erdos, Kent F. Hoskins, Kathy Calzone, Judy E. Garber, Jeff Boyd, Matthew B. Lubin, Michelle L. Deshano, Lawrence C. Brody, Francis S. Collins & Barbara L. Weber, Mutations in the BRCA1 Gene in Families with Early–Onset Breast and Ovarian Cancer, *Nature Genetics*, vol. 8, pp. 387–391 (1994).

P. Andrew Futreal, Qingyun Liu, Donna Shattuck–eidens, Charles Cochran, Keith Harshaman, Sean Tavtigian, L. Michelle Bennett, Astrid Haugen–Strano, Jeff Swenson, Yoshio Miki, Ken Eddington, Melody McClure, Cheryl Frye, Jane Weaver–Feldhaus, Wei Ding, Zahra Gholami, Peter Soderkvist, Lori Terry, Suresh Jhanwar, Andrew Berchuck, J. Dirk Iglehard, Jeff Marks, Dennis G. Ballinger, J. Carl Barrett, Mark H. Skolnick, Alexander Kamb, and Rober Wiseman, BRCA1 Mutations in Primary Breast and Ovarian Carcinomas, *Science,* vol. 266, pp. 120–122 (1994).

Leonard G. Davis, Mark D in Molecu. Dibner and James F. Battey, 17–1. $S_1$ Nuclease Protection Assay, *Methods in Molecular Biology,* pp. 276–284 (1986).

Liang, et al., Differential Display and Cloning of Messenger RNAs from Breast Cancer versus Mammary Epithelial Cells, *Cancer Research,* vol. 52, pp. 6966–6968 (1992).

Holt, et al., Histophathology: Old Principles and New Methods, *Cancer Surveys,* vol. 18, pp. 1–16, Tables 1 and 2 and Figures 1–5b (1993).

Neuhold, et al., Dioxin–Inducible Enhancer Region Upstream from the Mouse P–1450, Gene and Interaction with a Heterologous SV–40 Promoter, *DNA (N.Y.),* vol. 15, No. 5 (1986).

Chen, Y., Chen, C–F., Riley, D.J., Allred, D.G., Chen, P–L., Von Hoff, D., Osborne, C.K., and Lee, W–H. (1995) Aberrant subcellular localization of BRCA1 in breast cancer. *Science* 270:789–791.

Cornelius, R. S., Neuhausen, S. L., Johansson, O., Arason, A., Kelsell, D., Ponder, B. A., Tonin, P. Hamann, U., Lindblom, A., Lalle, P., et al. (1995). High allele loss rates at 17q12–q21 in breast and ovarian tumors from BRCA1–linked families. The Breast Cancer Linkage Consortium. *Genes Chrom Cancer* 13: 203–210.

Gayther, S. A., Mazoyer, S., Warren, W., Russell, P. A., Harrington, P. A., Chiano, M., Seal, S., Hamoudi, R., van Rensberg, E. J., Dunning, A. M., Love, R., Evans, G., Easton, D., Clayton, D., Stratton, M. R., Ponder, B. A. J. (1995). Germline mutations of the BRCA1 gene in breast/ovarian cancer families: Evidence for a genotype/phenotype correlation. *Nature Genet* 11: 428–433.

Gudas, J., Nguyen, H., Li, T., and Cowan, K. H. (1995). Hormone pendent regulation of BRCA1 in human breast cancer cells. *Cancer Res,* 55, 4561–4565.

Hall, J. M., Lee, M. K., Newman, B., Morrow, J. E., Anderson, L. A., Huey, B., King, M.–C. (1990). Linkage of early–onset breast cancer to chromosome 17q21. *Science* 250, 1684–1689.

Hosking, L., Trowsdale, J., Nicolai, H., Solomon, E., Foulkes, W., Stamp, G., Signer, E., Jeffreys, A. (1995). A somatic BRCA1 mutation in an ovarian tumour. *Nature Genetics* 9: 343–344.

Huttner, W. B., Gerdes, H. H., Rosa, P. (1991). The granin (chromogranin/secretogranin) family. *Trends Biochem. Sci.* 16, 27–30.

Marquis, S. T., Rajan, J. V., Wynshaw–Boris, A., Xu, J., Yin, G.–Y., Abel, K. J., Weber, B. L., and Chodosh, L. A. (1995). The development pattern of Brca1 expression implies a role in differentiation of the breast and other tissues. *Nature Genetics* 11, 17–26.

Merajver, S. D., Pham, T. M., Caduff, R. F., Chen, M., Poy, E. L., Cooney, K. A., Weber, B. L., Collins, F. S., Johnston, C., Frank, T.S. (1995). Somatic mutations in the BRCA1 gene in sporadic ovarian tumours, *Nature Genetics* 9, 439–443.

Takahashi, H., Behbakht, K., McGovern, P. E., Chiu, H.–C., Couch, F. J., Weber, B. L., Friedman, L. S., King, M.–C., Furusato, M., LiVolsi, V. A., Menzin, A. W., Liu, P. C., Benjamin, I., Morgan, M. A., King, S. A., Rebane, B. A., Cardonick, A., Mikuta, J. J., Rubin, S. C., and Boyd, J. (1995). Mutation analysis of the BRCA1 gene in ovarian cancers. *Cancer Res.* 55, 2998–3002.

Thompson, M. E., Jensen, R. A., Obermiller, P. S., Page, D. L., Holt, J. T. (1995). Decreased expression of BRCA1 accelerates growth and is often present during sporadic breast cancer progression. *Nature Genetics* 9, 444–450.

Wooster, et al., *Nature,* 379:789–792 (1995).

Figure 1: BRCA1 Antigens

C-19 (19 C-terminal amino acids): [Seq ID No: 5]
　　　Tyr Gln Cys Gln Glu Leu Asp Thr Tyr Leu Ile Pro Gln Ile Pro His Ser His Tyr C-20 (20 C-terminal amino acids): [Seq ID No: 6]
　　　Leu Tyr Gln Cys Gln Glu Leu Asp Thr Tyr Leu Ile Pro Gln Ile Pro His Ser His Tyr D-20 ( 20 N-terminal amino acids): [Seq ID No: 7]
　　　Met Asp Leu Ser Ala Leu Arg Val Glu Glu Val Gln Asn Val Ile Asn Ala Met Gln Lys

FIG. 1

Table of the Genetic Code

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

FIG. 2

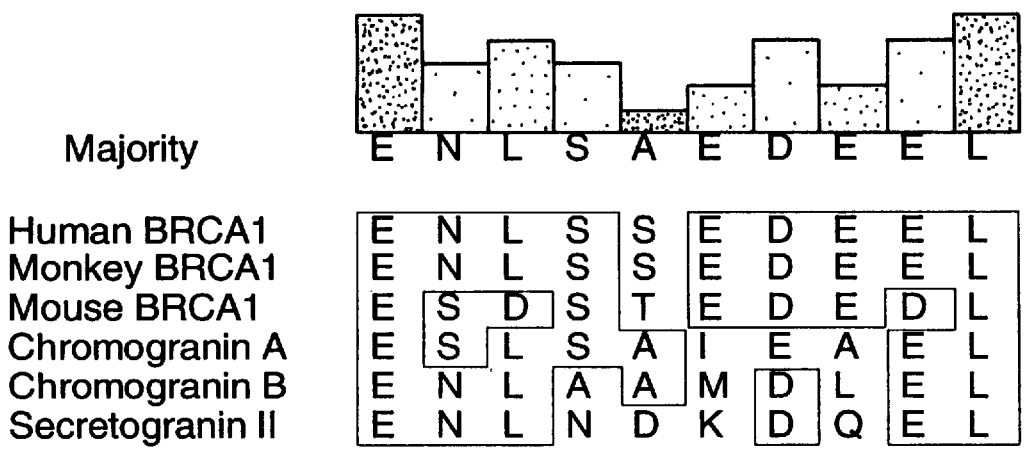

|                | AA1 | AA2 | AA3 | AA4 | AA5 | AA6 | AA7 | AA8 | AA9 |
|----------------|-----|-----|-----|-----|-----|-----|-----|-----|-----|
| Majority       | E   | N   | L   | S   | A   | E   | D   | E   | E   | L |
| Human BRCA1    | E   | N   | L   | S   | S   | E   | D   | E   | E   | L |
| Monkey BRCA1   | E   | N   | L   | S   | S   | E   | D   | E   | E   | L |
| Mouse BRCA1    | E   | S   | D   | S   | T   | E   | D   | E   | D   | L |
| Chromogranin A | E   | S   | L   | S   | A   | I   | E   | A   | E   | L |
| Chromogranin B | E   | N   | L   | A   | A   | M   | D   | L   | E   | L |
| Secretogranin II | E | N   | L   | N   | D   | K   | D   | Q   | E   | L |

Consensus

```
              S
   E  N  L  A  X  X  D  X  E  L
   D  S     N           E     D
```

The probability that BRCA1 would contain a polypeptide that would satisfy the granin consensus by chance alone is approximately 1 in 55. This calculation is based on the following rationale:

$$(N-n+1) \prod_{}^{n} \sum_{i=1}^{k} A_i$$

Where  $n$ = length of the consensus sequence
       $k$ = number of alternative amino acids at site $i$ of the consensus
       $A_i$ = frequency of amino acid $i$ in the entire sequence $N$ amino acids long

```
AA1  AA2  AA3  AA4  AA5  AA6  AA7  AA8  AA9  AA10  N-n+1  Probability
          S
 E    N    L    A    X    X    D    X    E    L
 D    L         N              E         D
0.15      0.08 1.0  1.0       1.0       0.08
     0.19     0.23           0.15      0.15         1854 = 0.0018
```

Note that this does not take into account the likelihood of amino acid pairs that frequently co-occur.

FIG. 4

Granin Sequences

| Granin | Species | Amino Acid | | | | | | | | |
|---|---|---|---|---|---|---|---|---|---|---|
| Consensus | | E<br>D | N<br>S | L | S<br>A<br>N | X | X | D<br>E | X | E<br>D | L |
| BRCA1 | Human | E | N | L | S | S | E | D | E | E | L |
| | Rhesus | E | N | L | S | S | E | D | E | E | L |
| | Mouse | E | S | D | S | T | E | D | E | D | L |
| BRCA2 | Human | E | S | N | S | I | A | D | E | E | L |
| Chromogranin A | Human | E | S | L | S | A | I | E | A | E | L |
| | Bovine | E | S | L | S | A | I | E | A | E | L |
| | Rat | E | S | L | S | A | I | E | A | E | L |
| | Pig | E | S | L | S | A | I | E | A | E | L |
| Chromogranin B | Human | E | N | L | A | A | M | D | L | E | L |
| | Bovine | E | N | L | A | A | M | D | L | E | L |
| | Mouse | E | N | L | A | A | M | D | L | E | L |
| Secretogranin II | Human | E | N | L | N | D | K | D | Q | E | L |
| | Bovine | E | N | L | N | D | K | D | Q | E | L |
| | Rat | D | N | L | N | D | K | D | Q | E | L |
| | Mouse | E | N | L | N | - | - | D | Q | E | L |
| Secretogranin III | Rat | E | N | L | D | E | T | I | A | L | Q |
| | Mouse | E | N | L | D | E | T | I | A | L | Q |
| Secretogranin V | Human | G | N | I | P | N | I | V | A | E | L |
| | Pig | G | N | I | P | N | I | V | A | E | L |
| | Rat | G | N | I | P | N | I | V | A | E | L |
| | Xenopus | G | N | I | P | N | I | V | A | E | L |
| Frequency of consensus amino acid in complete BRCA1 sequence | | 0.15 | 0.19 | 0.08 | 0.23 | 1 | 1 | 0.15 | 1 | 0.15 | 0.08 |

FIG. 5

Table I Effect of BRCA1 Expression Vectors on Growth

| Vector | Fibroblast | MCF-7 | CaOV-4 | Lung Ca | Colon Ca |
|---|---|---|---|---|---|
| LXSN | 85+2.5 | 85+3.7 | 72+2.3 | 98+1.7 | 433+9.4 |
| BRCA1 | 87+2.2 | 0+0* | 0+0* | 101+4.2 | 480+16.3 |
| Δ343-1081 | 84+1.4 | 96+3.7 | 76+4.9 | 97+3.7 | 460+29.4 |
| Δ515-1092 | 88+2.4 | 93+15.9 | 77+4.2 | 99+5.0 | 473+28.7 |
| 1835 Stop | 85+1.2 | 88+3.3 | 3+1.7 | 102+5.8 | 473+20.5 |
| 340 Stop | 87+1.4 | 89+3.3 | 80+2.7 | 99+5.0 | 483+33.0 |

G418-resistant transfectants per 107 cells, Mean + Standard Error
Lung cancer cells = FK111; colon cancer cells = OK3;
Breast cancer cell line = MCF-7; Ovarian cancer cell line = CaOV-4
* 10-20 small colonies were identified in each transfection but these never grew beyond 30 cells per clone.

FIG. 6

Table II. Inherited BRCA1 mutation and type of cancer

| Termination codon of mutant protein | Cancer site Breast | Ovary |
|---|---|---|
| 0a | 16 | 3 |
| 36 | 2 | |
| 37 | 7 | 1 |
| 39 | 17 | 9 |
| 64 | 6 | 4 |
| 81 | 4 | 2 |
| 313 | 5 | 1 |
| 766 | 3 | 4 |
| 780 | 7 | |
| 901 | 14 | 4 |
| 915 | 4 | 3 |
| 123 | 6 | |
| 1214-1223 | Granin motif | |
| 1265 | 5 | |
| 1364 | 12 | 1 |
| 1829 | 6 | |
| 1853 | 7 | |
| 1863b | 13 | |
| 0-1223 | 91 | 31  25% |
| 1223-1863 | 43 | 1  2% | a Nonsense mutations leading to loss of transcript
b Complete problem: missense mutations in RING finger

FIG. 7

Table III. Inhibition of Tumorigenesis by BRCA1

| Vector | MCF-7 (4wks) | MCF-7 (8wks) | Weight of MCF Tumor | MCF-7 stables | Established tumors | Colon Tumors* |
|---|---|---|---|---|---|---|
| None | 6/6 | 6/6* | Not done | Not done | Not done | 5/6 |
| BRCA1 | 0/6 | 4/6* | 60g+24 | 0/20 | 24.4+2.1# | 6/6 |
| Δ343-1081 | 5/6 | 6/6* | 569g+60 | 13/15 | 8.6+1.3# | 6/6 |

The columns headed MCF-7 (4wks) and (8wks) and colon tumors are results following retroviral transduction of cultured cells. The assay for inhibition of established tumor growth was whether the retrovirus could delay survival for an additional 14 days. The column labeled MCF-7 stables shows tumor development of cloned BRCA1 and mutant cell lines. MCF-7 stables are results of stable transformants.
*colon tumor weights: BRCA1=1540+128; Δ343-1081=1633+110
mean+SE of post injection survivals (days): BRCA1=15,18,22,26,41
　　Δ343-1081=4,8,9,11,11

FIG. 8

Gene sequence for BRCA1 [SEQ ID NO: 1]
(reference Miki et al. Science 266:66, 1994)

agctcgctgagacttcctggaccccgcaccaggctgtggggtttctcagataactgggcccctgcgctca ggaggccttcaccctctgctctgggtaaagttcattggaacagaaagaaatggatttatctgctcttcgcgt tgaagaagtacaaaatgtcattaatgctatgcagaaaatcttagagtgtcccatctgtctggagttgatcaa ggaacctgtctccacaaagtgtgaccacatattttgcaaattttgcatgctgaaacttctcaaccagaagaa agggccttcacagtgtcctttatgtaagaatgatataaccaaaaggagcctacaagaaagtacgagattta gtcaacttgttgaagagctattgaaaatcatttgtgcttttcagcttgacacaggtttggagtatgcaaacag ctataattttgcaaaaaggaaaataactctcctgaacatctaaaagatgaagtttctatcatccaaagtatg ggctacagaaaccgtgccaaaagacttctacagagtgaacccgaaaatccttccttgcaggaaaccagtc tcagtgtccaactctctaaccttggaactgtgagaactctgaggacaaagcagcggatacaacctcaaaa gacgtctgtctacattgaattgggatctgattcttctgaagataccgttaataaggcaacttattgcagtgtg ggagatcaagaattgttacaaatcacccctcaaggaaccagggatgaaatcagtttggattctgcaaaaa aggctgcttgtgaattttctgagacggatgtaacaaatactgaacatcatcaacccagtaataatgatttgaa caccactgagaagcgtgcagctgagaggcatccagaaaagtatcagggtagttctgtttcaaacttgcat gtggagccatgtggcacaaatactcatgccagctcattacagcatgagaacagcagtttattactcactaa agacagaatgaatgtagaaaaggctgaattctgtaataaaagcaaacagcctggcttagcaaggagcca acataacagatgggctggaagtaaggaaacatgtaatgataggcggactcccagcacagaaaaaaagg tagatctgaatgctgatccctgtgtgagagaaaagaatggaataagcagaaactgccatgctcagagaa tcctagagatactgaagatgttccttggataacactaaatagcagcattcagaaagttaatgagtggttttcc agaagtgatgaactgttaggttctgatgactcacatgatggggagtctgaatcaaatgccaaagtagctga tgtattggacgttctaaatgaggtagatgaatattctggttcttcagagaaaatagacttactggccagtgat cctcatgaggctttaatatgtaaaagtgaaagagttcactccaaatcagtagagagtaatattgaagacaaa atatttgggaaaacctatcggaagaaggcaagcctccccaacttaagccatgtaactgaaaatctaattata

FIG. 9A ggagcatttgttactgagccacagataatacaagagcgtcccctcacaaataaattaaagcgtaaaagga
gacctacatcaggccttcatcctgaggattttatcaagaaagcagatttggcagttcaaaagactcctgaaa
tgataaatcagggaactaaccaaacggagcagaatggtcaagtgatgaatattactaatagtggtcatga
gaataaaacaaaaggtgattctattcagaatgagaaaaatcctaacccaatagaatcactcgaaaaagaat
ctgctttcaaaacgaaagctgaacctataagcagcagtataagcaatatggaactcgaattaaatatccac
aattcaaaagcacctaaaaagaataggctgaggaggaagtcttctaccaggcatattcatgcgcttgaact
agtagtcagtagaaatctaagcccacctaattgtactgaattgcaaattgatagttgttctagcagtgaaga
gataaagaaaaaaagtacaaccaaatgccagtcaggcacagcagaaacctacaactcatggaaggta
aagaacctgcaactggagccaagaagagtaacaagccaaatgaacagacaagtaaaagacatgacag
cgatactttcccagagctgaagttaacaaatgcacctggttcttttactaagtgttcaaataccagtgaactta
agaatttgtcaatcctagccttccaagagaagaaaaagaagagaaactagaaacagttaaagtgtctaat
aatgctgaagaccccaaagatctcatgttaagtggagaaagggttttgcaaactgaaagatctgtagaga
gtagcagtatttcattggtacctggtactgattatggcactcaggaaagtatctcgttactggaagttagcac
tctagggaaggcaaaaacagaaccaaataaatgtgtgagtcagtgtgcagcatttgaaaaccccaaggg
actaattcatggttgttccaaagataatagaaatgacacagaaggctttaagtatccattgggacatgaagt
taaccacagtcgggaaacaagcatagaaatggaagaaagtgaacttgatgctcagtatttgcagaataca
ttcaaggtttcaaagcgccagtcatttgctccgttttcaaatccaggaaatgcagaagaggaatgtgcaac
attctctgcccactctgggtccttaaagaaacaaagtccaaaagtcacttttgaatgtgaacaaaaggaag
aaaatcaaggaaagaatgagtctaatatcaagcctgtacagacagttaatatcactgcaggctttcctgtg
gttggtcagaaagataagccagttgataatgccaaatgtagtatcaaaggaggctctaggttttgtctatca
tctcagttcagaggcaacgaaactggactcattactccaaataaacatggacttttacaaaacccatatcgt
ataccaccacttttttcccatcaagtcatttgttaaaactaaatgtaagaaaaatctgctagaggaaaactttga
ggaacattcaatgtcacctgaaagagaaatgggaaatgagaacattccaagtacagtgagcacaattagc
cgtaataacattagagaaaatgttttţaaagaagccagctcaagcaatattaatgaagtaggttccagtact
aatgaagtgggctccagtattaatgaaataggttccagtgatgaaaacattcaagcagaactaggtagaa

FIG. 9B acagagggccaaaattgaatgctatgcttagattaggggttttgcaacctgaggtctataaacaaagtcttc ctggaagtaattgtaagcatcctgaaataaaaaagcaagaatatgaagaagtagttcagactgttaataca gatttctctccatatctgatttcagataacttagaacagcctatgggaagtagtcatgcatctcaggtttgttct gagacacctgatgacctgttagatgatggtgaaataaaggaagatactagttttgctgaaaatgacattaa ggaaagttctgctgtttttagcaaaagcgtccagaaaggagagcttagcaggagtcctagcccttcaccc atacacatttggctcagggttaccgaagaggggccaagaaattagagtcctcagaagagaacttatctag tgaggatgaagagcttccctgcttccaacacttgttatttggtaaagtaaacaatatacctcctcagtctacta ggcatagcaccgttgctaccgagtgtctgtctaagaacacagaggagaatttattatcattgaagaatagc ttaaatgactgcagtaaccaggtaatattggcaaaggcatctcaggaacatcaccttagtgaggaaacaa aatgttctgctagcttgttttcttcacagtgcagtgaattggaagacttgactgcaaatacaaacacccagg atcctttcttgattggttcttccaaacaaatgaggcatcagtctgaaagccagggagttggtctgagtgaca aggaattggtttcagatgatgaagaaagaggaacgggcttggaagaaaataatcaagaagagcaaagc atggattcaaacttaggtgaagcagcatctgggtgtgagagtgaaacaagcgtctctgaagactgctcag ggctatcctctcagagtgacattttaaccactcagcagagggataccatgcaacataacctgataaagctc cagcaggaaatggctgaactagaagctgtgttagaacagcatgggagccagccttctaacagctacccctt ccatcataagtgactcttctgcccttgaggacctgcgaaatccagaacaaagcacatcagaaaaagcagt attaacttcacagaaaagtagtgaatacctataagccagaatccagaaggcctttctgctgacaagttga ggtgtctgcagatagttctaccagtaaaaataaagaaccaggagtggaaaggtcatccccttctaaatgcc catcattagatgataggtggtacatgcacagttgctctgggagtcttcagaatagaaactacccatctcaag aggagctcattaaggttgttgatgtggaggagcaacagctggaagagtctgggccacacgatttgacgg aaacatcttacttgccaaggcaagatctagagggaaccccttacctggaatctggaatcagcctcttctctg atgaccctgaatctgatccttctgaagacagagccccagagtcagctcgtgttggcaacataccatcttca acctctgcattgaaagttccccaattgaaagttgcagaatctgcccagagtccagctgctgctcatactact gatactgctgggtataatgcaatggaagaaagtgtgagcagggagaagccagaattgacagcttcaaca gaaagggtcaacaaaagaatgtccatggtggtgtctggcctgaccccagaagaatttatgctcgtgtaca

FIG. 9C agtttgccagaaaacaccacatcactttaactaatctaattactgaagagactactcatgttgttatgaaaac
agatgctgagtttgtgtgtgaacggacactgaaatattttctaggaattgcgggaggaaaatgggtagtta
gctatttctgggtgacccagtctattaaagaaagaaaaatgctgaatgagcatgattttgaagtcagagga
gatgtggtcaatggaagaaaccaccaaggtccaaagcgagcaagagaatcccaggacagaaagatctt
caggggggctagaaatctgttgctatgggcccttcaccaacatgcccacagatcaactggaatggatggta
cagctgtgtggtgcttctgtggtgaaggagctttcatcattcacccttggcacaggtgtccacccaattgtg
gttgtgcagccagatgcctggacagaggacaatggcttccatgcaattgggcagatgtgtgaggcacct
gtggtgacccgagagtgggtgttggacagtgtagcactctaccagtgccaggagctggacacctacctg
atacccagatcccccacagccactactgat

FIG. 9D

Sequence of the BRCA2 cDNA [SEQ ID NO: 3]

ggtggcgcgagcttctgaaactaggcggcagaggcggagccgctgtggcactgctgcgcctctgctgcgcc tcgggtgtcttttgcggcggtgggtcgccgccgggagaagcgtgaggggacagatttgtgaccggcgcggt ttttgtcagcttactccggccaaaaaagaactgcacctctggagcggacttatttaccaagcattggaggaatatc gtaggtaaaaatgcctattggatccaaagagaggccaacattttttgaaattttaagacacgctgcaacaaagc agatttaggaccaataagtcttaattggtttgaagaactttcttcagaagctccaccctataattctgaacctgcag aagaatctgaacataaaaacaacaattacgaaccaaacctatttaaaactccacaaaggaaaccatcttataatca gctggcttcaactccaataatattcaaagagcaagggctgactctgccgctgtaccaatctcctgtaaaagaatta gataaattcaaattagacttaggaaggaatgttcccaatagtagacataaaagtcttcgcacagtgaaaactaaa atggatcaagcagatgatgtttcctgtccacttctaaattcttgtcttagtgaaagtcctgttgttctacaatgtacac atgtaacaccacaaagagataagtcagtggtatgtgggagtttgtttcatacaccaaagtttgtgaagggtcgtc agacaccaaaacatatttctgaaagtctaggagctgaggtggatcctgatatgtcttggtcaagttctttagctac accacccacccttagttctactgtgctcatagtcagaaatgaagaagcatctgaaactgtatttcctcatgatacta ctgctaatgtgaaaagctattttttccaatcatgatgaaagtctgaagaaaaatgatagatttatcgcttctgtgaca gacagtgaaaacacaaatcaaagagaagctgcaagtcatggatttggaaaaacatcagggaattcatttaaagt aaatagctgcaaagaccacattggaaagtcaatgccaaatgtcctagaagatgaagtatatgaaacagttgtag atacctctgaagaagatagttttttcattatgtttttctaaatgtagaacaaaaaatctacaaaaagtaagaactagca agactaggaaaaaaattttccatgaagcaaacgctgatgaatgtgaaaaatctaaaaaccaagtgaaagaaaaa tactcatttgtatctgaagtggaaccaaatgatactgatccattagattcaaatgtagcacatcagaagcccttga gagtggaagtgacaaaatctccaaggaagttgtaccgtctttggcctgtgaatggtctcaactaacccttcagg tctaaatggagcccagatggagaaaatacccctattgcatatttcttcatgtgaccaaaatatttcagaaaaagac ctattagacacagagaacaaaagaaagaaagattttcttacttcagagaattctttgccacgtatttctagcctacc aaaatcagagaagccattaaatgaggaaacagtggtaaataagagagatgaagagcagcatcttgaatctcat acagactgcattcttgcagtaaagcaggcaatatctggaacttctccagtggcttcttcatttcagggtatcaaaa agtctatattcagaataagagaatcacctaaagagactttcaatgcaagttttcaggtcatatgactgatccaaac

FIG. 10A tttaaaaaagaaactgaagcctctgaaagtggactggaaatacatactgtttgctcacagaaggaggactcctta tgtccaaatttaattgataatggaagctggccagccaccaccacacagaattctgtagctttgaagaatgcaggtt taatatccactttgaaaaagaaaacaaataagtttatttatgctatacatgatgaaacattttataaaggaaaaaaaa taccgaaagaccaaaaatcagaactaattaactgttcagcccagtttgaagcaaatgcttttgaagcaccacttac atttgcaaatgctgattcaggtttattgcattcttctgtgaaaagaagctgttcacagaatgattctgaagaaccaa ctttgtccttaactagctcttttgggacaattctgaggaaatgttctagaaatgaaacatgttctaataatacagtaat ctctcaggatcttgattataaagaagcaaaatgtaataaggaaaaactacagttatttattaccccagaagctgatt ctctgtcatgcctgcaggaaggacagtgtgaaaatgatccaaaaagcaaaaaagtttcagatataaagaaga ggtcttggctgcagcatgtcacccagtacaacattcaaaagtggaatacagtgatactgactttcaatcccagaa aagtcttttatatgatcatgaaaatgccagcactcttatttaactcctacttccaaggatgttctgtcaaacctagtc atgatttctagaggcaaagaatcatacaaaatgtcagacaagctcaaaggtaacaattatgaatctgatgttgaat taaccaaaaatattcccatggaaaagaatcaagatgtatgtgctttaaatgaaaattataaaaacgttgagctgttg ccacctgaaaaatacatgagagtagcatcaccttcaagaaaggtacaattcaaccaaaacacaaatctaagagt aatccaaaaaaatcaagaagaaactacttcaatttcaaaaataactgtcaatccagactctgaagaacttttctcag acaatgagaataattttgtcttccaagtagctaatgaaaggaataatcttgctttaggaaatactaaggaacttcat gaaacagacttgacttgtgtaaacgaacccattttcaagaactctaccatggttttatatggagacacaggtgata aacaagcaacccagtgtcaattaaaaaagatttggtttatgttcttgcagaggagaacaaaaatagtgtaaagc agcatataaaaatgactctaggtcaagatttaaaatcggacatctccttgaatatagataaaataccagaaaaaaa taatgattacatgaacaaatgggcaggactcttaggtccaatttcaaatcacagttttggaggtagcttcagaaca gcttcaaataaggaaatcaagctctctgaacataacattaagaagagcaaaatgttcttcaaagatattgaagaac aatatcctactagtttagcttgtgttgaaattgtaaataccttggcattagataatcaaaagaaactgagcaagcct cagtcaattaatactgtatctgcacatttacagagtagtgtagttgtttctgattgtaaaaatagtcatataaccccctc agatgttattttccaagcaggattttaattcaaaccataatttaacacctagccaaaaggcagaaattacagaacttt ctactatattagaagaatcaggaagtcagtttgaatttactcagtttagaaaaccaagctacatattgcagaagagt acatttgaagtgcctgaaaaccagatgactatcttaaagaccacttctgaggaatgcagagatgctgatcttcatg tcataatgaatgccccatcgattggtcaggtagacagcagcaagcaatttgaaggtacagttgaaattaaacgg aagtttgctggcctgttgaaaaatgactgtaacaaaagtgcttctggttatttaacagatgaaaatgaagtgggt

FIG. 10B ttaggggcttttattctgctcatggcacaaaactgaatgtttctactgaagctctgcaaaaagctgtgaaactgttta
gtgatattgagaatattagtgaggaaacttctgcagaggtacatccaataagtttatcttcaagtaaatgtcatgatt
ctgttgtttcaatgtttaagatagaaaatcataatgataaaactgtaagtgaaaaaaataataaatgccaactgatat
tacaaaataatattgaaatgactactggcactttgttgaagaaattactgaaaattacaagagaaatactgaaaat
gaagataacaaatatactgctgccagtagaaattctcataacttagaatttgatggcagtgattcaagtaaaaatg
atactgtttgtattcataaagatgaaacggacttgctatttactgatcagcacaacatatgtcttaaattatctggcca
gtttatgaaggagggaaacactcagattaaagaagatttgtcagatttaacttttttggaagttgcgaaagctcaa
gaagcatgtcatggtaatacttcaaataaagaacagttaactgctactaaaacggagcaaaatataaaagattttg
agacttctgatacatttttcagactgcaagtgggaaaaatattagtgtcgccaaagagttatttaataaaattgtaa
atttctttgatcagaaaccagaagaattgcataacttttccttaaattctgaattacattctgacataagaaagaaca
aaatggacattctaagttatgaggaaacagacatagttaaacacaaaatactgaaagaaagtgtcccagttggta
ctggaaatcaactagtgaccttccagggacaacccgaacgtgatgaaaagatcaaagaacctactctgttgggt
tttcatacagctagcggaaaaaaagttaaaattgcaaaggaatctttggacaaagtgaaaaacctttttgatgaaa
aagagcaaggtactagtgaaatcaccagttttagccatcaatgggcaaagaccctaaagtacagagaggcctg
taaagaccttgaattagcatgtgagaccattgagatcacagctgccccaaagtgtaaagaaatgcagaattctct
caataatgataaaaaccttgtttctattgagactgtggtgccacctaagctcttaagtgataatttatgtagacaaac
tgaaaatctcaaaacatcaaaaagtatctttttgaaagttaaagtacatgaaaatgtagaaaaagaaacagcaaaa
agtcctgcaacttgttacacaaatcagtccccttattcagtcattgaaaattcagccttagcttttacacaagttgta
gtagaaaaacttctgtgagtcagacttcattacttgaagcaaaaaaatggcttagagaaggaatatttgatggtca
accagaaagaataaatactgcagattatgtaggaaattatttgtatgaaaataattcaaacagtactatagctgaaa
atgacaaaaatcatctctccgaaaaacaagatacttatttaagtaacagtagcatgtctaacagctattcctaccatt
ctgatgaggtatataatgattcaggatatctctcaaaaaataaacttgattctggtattgagccagtattgaagaat
gttgaagatcaaaaaaacactagttttccaaagtaatatccaatgtaaaagatgcaaatgcatacccacaaactg
taaatgaagatatttgcgttgaggaacttgtgactagctcttcaccctgcaaaaataaaaatgcagccattaaattg
tccatatctaatagtaataattttgaggtagggccacctgcatttaggatagccagtggtaaaatccgtttgtgttc
acatgaaacaattaaaaaagtgaaagacatatttacagacagtttcagcaaagtaattaaggaaaacaacgaga
ataaatcaaaaatttgccaaacgaaaattatggcaggttgttacgaggcattggatgattcagaggatattcttcat

FIG. 10C aactctctagataatgatgaatgtagcatgcattcacataaggttttgctgacattcagagtgaagaaattttacaa
cataaccaaaatatgtctggattggagaaagtttctaaaatatcaccttgtgatgttagtttggaaacttcagatata
tgtaaatgtagtatagggaagcttcataagtcagtctcatctgcaaatacttgtgggattttttagcacagcaagtg
gaaaatctgtccaggtatcagatgcttcattacaaaacgcaagacaagtgttttctgaaatagaagatagtaccaa
gcaagtcttttccaaagtattgtttaaaagtaacgaacattcagaccagctcacaagagaagaaaatactgctata
cgtactccagaacatttaatatcccaaaaaggcttttcatataatgtggtaaattcatctgctttctctggatttagta
cagcaagtggaaagcaagtttccattttagaaagttccttacacaaagttaagggagtgttagaggaatttgattt
aatcagaactgagcatagtcttcactattcacctacgtctagacaaaatgtatcaaaaatacttcctcgtgttgataa
gagaaacccagagcactgtgtaaactcagaaatggaaaaaacctgcagtaaagaatttaaattatcaaataactt
aaatgttgaaggtggttcttcagaaaataatcactctattaaagtttctccatatctctctcaatttcaacaagacaaa
caacagttggtattaggaaccaaagtctcacttgttgagaacattcatgttttgggaaaagaacaggcttaccta
aaaacgtaaaaatggaaattggtaaaactgaaacttttctgatgttcctgtgaaaacaaatatagaagtttgttcta
cttactccaaagattcagaaaactactttgaaacagaagcagtagaaattgctaaagcttttatggaagatgatga
actgacagattctaaactgccaagtcatgccacacattctcttttacatgtcccgaaaatgaggaaatggttttgt
caaattcaagaattggaaaaagaagaggagagccccttatcttagtgggagaaccctcaatcaaaagaaactta
ttaaatgaatttgacaggataatagaaaatcaagaaaaatccttaaaggcttcaaaaagcactccagatggcaca
ataaaagatcgaagattgtttatgcatcatgtttctttagagccgattacctgtgtacccttcgcacaactaaggaa
cgtcaagagatacagaatccaaattttaccgcacctggtcaagaatttctgtctaaatctcatttgtatgaacatctg
actttggaaaaatcttcaagcaatttagcagtttcaggacatccattttatcaagtttctgctacaagaaatgaaaaa
atgagacacttgattactacaggcagaccaaccaaagtctttgttccaccttttaaaactaaatcacattttcacag
agttgaacagtgtgttaggaatattaacttggaggaaaacagacaaaagcaaaacattgatggacatggctctg
atgatagtaaaaataagattaatgacaatgagattcatcagtttaacaaaaacaactccaatcaagcagcagctgt
aactttcacaaagtgtgaagaagaacctttagatttaattacaagtcttcagaatgccagagatatacaggatatg
cgaattaagaagaaacaaaggcaacgcgtctttccacagccaggcagtctgtatcttgcaaaaacatccactct
gcctcgaatctctctgaaagcagcagtaggaggccaagttccctctgcgtgttctcataaacagctgtatacgta
tggcgtttctaaacattgcataaaaattaacagcaaaaatgcagagtcttttcagtttcacactgaagattatttgg
taaggaaagtttatggactggaaaaggaatacagttggctgatggtggatggctcatacccctccaatgatgaa

FIG. 10D aggctggaaaagaagaattttatagggctctgtgtgacactccaggtgtggatccaaagcttatttctagaatttg ggtttataatcactatagatggatcatatggaaactggcagctatggaatgtgcctttcctaaggaatttgctaata gatgcctaagcccagaaagggtgcttcttcaactaaaatacagatatgatacggaaattgatagaagcagaaga tcggctataaaaaagataatggaaagggatgacacagctgcaaaaacacttgttctctgtgtttctgacataattt cattgagcgcaaatatatctgaaacttctagcaataaaactagtagtgcagatacccaaaaagtggccattattga acttacagatgggtggtatgctgttaaggcccagttagatcctcccctcttagctgtcttaaagaatggcagactg acagttggtcagaagattattcttcatggagcagaactggtgggctctcctgatgcctgtacacctcttgaagcc ccagaatctcttatgttaaagatttctgctaacagtactcggcctgctcgctggtataccaaacttggattctttcct gaccctagaccttttcctctgccccttatcatcgcttttcagtgatggaggaaatgttggttgtgttgatgtaattattc aaagagcatacctatacagcggatggagaagacatcatctggattatacatatttcgcaatgaaagagaggaa gaaaaggaagcagcaaaatatgtggaggcccaacaaaagagactagaagccttattcactaaaattcaggag gaatttgaagaacatgaagaaaacacaacaaaaccatatttaccatcacgtgcactaacaagacagcaagttcg tgctttgcaagatggtgcagagctttatgaagcagtgaagaatgcagcagacccagcttaccttgagggttattt cagtgaagagcagttaagagccttgaataatcacaggcaaatgttgaatgataagaaacaagctcagatccagt tggaaattaggaaggccatggaatctgctgaacaaaaggaacaaggtttatcaagggatgtcacaaccgtgtg gaagttgcgtattgtaagctattcaaaaaaagaaaaagattcagttatactgagtatttggcgtccatcatcagatt tatattctctgttaacagaaggaaagagatacagaatttatcatcttgcaacttcaaaatctaaaagtaaatctgaaa gagctaacatacagttagcagcgacaaaaaaaactcagtatcaacaactaccggtttcagatgaaattttatttca gatttaccagccacgggagccccttcacttcagcaaattttagatccagactttcagccatcttgttctgaggtgg acctaataggatttgtcgtttctgttgtgaaaaaaacaggacttgccccttcgtctatttgtcagacgaatgttaca atttactggcaataaagttttggatagaccttaatgaggacattattaagcctcatatgttaattgctgcaagcaacc tccagtggcgaccagaatccaaatcaggccttcttactttatttgctggagattttctgtgttttctgctagtccaaa agagggccactttcaagagacattcaacaaaatgaaaaatactgttgagaatattgacatactttgcaatgaagc agaaaacaagcttatgcatatactgcatgcaaatgatcccaagtggtccaccccaactaaagactgtacttcagg gccgtacactgctcaaatcattcctggtacaggaaacaagcttctgatgtcttctcctaattgtgagatatattatca aagtcctttatcactttgtatggccaaaaggaagtctgtttccacacctgtctcagcccagatgacttcaaagtctt gtaaaggggagaaagagattgatgaccaaaagaactgcaaaaagagaagagccttggatttcttgagtagact

FIG. 10E gcctttacctccacctgttagtcccatttgtacatttgtttctccggctgcacagaaggcatttcagccaccaagga gttgtggcaccaaatacgaaacacccataaagaaaaaagaactgaattctcctcagatgactccatttaaaaaatt caatgaaatttctcttttggaaagtaattcaatagctgacgaagaacttgcattgataaatacccaagctcttttgtct ggttcaacaggagaaaaacaatttatatctgtcagtgaatccactaggactgctcccaccagttcagaagattatc tcagactgaaacgacgttgtactacatctctgatcaaagaacaggagagttcccaggccagtacggaagaatgt gagaaaaataagcaggacacaattacaactaaaaaatatatctaagcatttgcaaaggcgacaataaaattattga cgcttaacctttccagtttataagactggaatataatttcaaaccacacattagtacttatgttgccaatgagaaaag aaattagtttcaaatttacctcagcgtttgtgtatcgggcaaaaatcgttttgcccgattccgtattggtatactttg cctcagttgcatatcctaaaactaaatgtaatttattaactaatcaagaaaaacatctttggctgagctcggtggctc atgcctgtaatcccaacactttgagaagctgaggtgggaggagtgcttgaggccaggagttcaagaccagcct gggcaacatagggagaccccatctttacgaagaaaaaaaaaaggggaaaagaaaatcttttaaatctttggat ttcactacaagtattattttacaagtgaaataaacataccatttttcttttagattgtgtcattaaatggaatgaggtctc ttagtacagttattttgatgcagataattccttttagtttagctactattttaggggatttttttttagaggtaactcactat gaaatagttccccttaatgcaaatatgttggttctgcaatagttccatcctgttcaaaatcggtgaaatgaagagtg gtgttccttttgagcaattctcatccttaagtcagctgattataagaaaaatagaaccccagtgtaacctaattccttt ttctattccagtgtgatctctgaaataaattacttcactaaaaattcaaaaacttaatcagaaattcaagtaatttatttt ttttt

FIG. 10F

BRCA2 Protein sequence [SEQ ID NO: 4]

MPIGSKERPTFFEIFKTRCNKADLGPISLNWFEELSSEAPPYNSEPAEE
SEHKNNNYEPNLFKTPQRKPSYNQLASTPIIFKEQGLTLPLYQSPVKE
LDKFKLDLGRNVPNSRHKSLRTVKTKMDQADDVSCPLLNSCLSESPV
VLQCTHVTPQRDKSVVCGSLFHTPKFVKGRQTPKHISESLGAEVDPD
MSWSSSLATPPTLSSTVLIVRNEEASETVFPHDTTANVKSYFSNHDES
LKKNDRFIASVTDSENTNQREAASHGFGKTSGNSFKVNSCKDHIGKS
MPNVLEDEVYETVVDTSEEDSFSLCFSKCRTKNLQKVRTSKTRKKIF
HEANADECEKSKNQVKEKYSFVSEVEPNDTDPLDSNVAHQKPFESGS
DKISKEVVPSLACEWSQLTLSGLNGAQMEKIPLLHISSCDQNISEKDL
LDTENKRKKDFLTSENSLPRISSLPKSEKPLNEETVVNKRDEEQHLES
HTDCILAVKQAISGTSPVASSFQGIKKSIFRIRESPKETFNASFSGHMTD
PNFKKETEASESGLEIHTVCSQKEDSLCPNLIDNGSWPATTTQNSVAL
KNAGLISTLKKKTNKFIYAIHDETFYKGKKIPKDQKSELINCSAQFEA
NAFEAPLTFANADSGLLHSSVKRSCSQNDSEEPTLSLTSSFGTILRKCS
RNETCSNNTVISQDLDYKEAKCNKEKLQLFITPEADSLSCLQEGQCE
NDPKSKKVSDIKEEVLAAACHPVQHSKVEYSDTDFQSQKSLLYDHEN
ASTLILTPTSKDVLSNLVMISRGKESYKMSDKLKGNNYESDVELTKNI
PMEKNQDVCALNENYKNVELLPPEKYMRVASPSRKVQFNQNTNLR
VIQKNQEETTSISKITVNPDSEELFSDNENNFVFQVANERNNLALGNT
KELHETDLTCVNEPIFKNSTMVLYGDTGDKQATQVSIKKDLVYVLA
EENKNSVKQHIKMTLGQDLKSDISLNIDKIPEKNNDYMNKWAGLLG
PISNHSFGGSFRTASNKEIKLSEHNIKKSKMFFKDIEEQYPTSLACVEIV
NTLALDNQKKLSKPQSINTVSAHLQSSVVVSDCKNSHITPQMLFSKQD
FNSNHNLTPSQKAEITELSTILEESGSQFEFTQFRKPSYILQKSTFEVPE

FIG. 11A

NQMTILKTTSEECRDADLHVIMNAPSIGQVDSSKQFEGTVEIKRKFAG
LLKNDCNKSASGYLTDENEVGFRGFYSAHGTKLNVSTEALQKAVKL
FSDIENISEETSAEVHPISLSSSKCHDSVVSMFKIENHNDKTVSEKNNKC
QLILQNNIEMTTGTFVEEITENYKRNTENEDNKYTAASRNSHNLEFD
GSDSSKNDTVCIHKDETDLLFTDQHNICLKLSGQFMKEGNTQIKEDLS
DLTFLEVAKAQEACHGNTSNKEQLTATKTEQNIKDFETSDTFFQTAS
GKNISVAKELFNKIVNFFDQKPEELHNFSLNSELHSDIRKNKMDILSY
EETDIVKHKILKESVPVGTGNQLVTFQGQPERDEKIKEPTLLGFHTAS
GKKVKIAKESLDKVKNLFDEKEQGTSEITSFSHQWAKTLKYREACK
DLELACETIEITAAPKCKEMQNSLNNDKNLVSIETVVPPKLLSDNLC
RQTENLKTSKSIFLKVKVHENVEKETAKSPATCYTNQSPYSVIENSAL
AFYTSCSRKTSVSQTSLLEAKKWLREGIFDGQPERINTADYVGNYLY
ENNSNSTIAENDKNHLSEKQDTYLSNSSMSNSYSYHSDEVYNDSGYLS
KNKLDSGIEPVLKNVEDQKNTSFSKVISNVKDANAYPQTVNEDICVE
ELVTSSSPCKNKNAAIKLSISNSNNFEVGPPAFRIASGKIRLCSHETIKK
VKDIFTDSFSKVIKENNENKSKICQTKIMAGCYEALDDSEDILHNSLD
NDECSMHSHKVFADIQSEEILQHNQNMSGLEKVSKISPCDVSLETSDIC
KCSIGKLHKSVSSANTCGIFSTASGKSVQVSDASLQNARQVFSEIEDST
KQVFSKVLFKSNEHSDQLTREENTAIRTPEHLISQKGFSYNVVNSSAFS
GFSTASGKQVSILESSLHKVKGVLEEFDLIRTEHSLHYSPTSRQNVSKI
LPRVDKRNPEHCVNSEMEKTCSKEFKLSNNLNVEGGSSENNHSIKVSP
YLSQFQQDKQQLVLGTKVSLVENIHVLGKEQASPKNVKMEIGKTET
FSDVPVKTNIEVCSTYSKDSENYFETEAVEIAKAFMEDDELTDSKLPS
HATHSLFTCPENEEMVLSNSRIGKRRGEPLILVGEPSIKRNLLNEFDRI
IENQEKSLKASKSTPDGTIKDRRLFMHHVSLEPITCVPFRTTKERQEIQ
NPNFTAPGQEFLSKSHLYEHLTLEKSSSNLAVSGHPFYQVSATRNEK

FIG. 11B

MRHLITTGRPTKVFVPPFKTKSHFHRVEQCVRNINLEENRQKQNIDG
HGSDDSKNKINDNEIHQFNKNNSNQAAAVTFTKCEEEPLDLITSLQN
ARDIQDMRIKKKQRQRVFPQPGSLYLAKTSTLPRISLKAAVGGQVPS
ACSHKQLYTYGVSKHCIKINSKNAESFQFHTEDYFGKESLWTGKGIQ
LADGGWLIPSNDGKAGKEEFYRALCDTPGVDPKLISRIWVYNHYRW
IIWKLAAMECAFPKEFANRCLSPERVLLQLKYRYDTEIDRSRRSAIKK
IMERDDTAAKTLVLCVSDIISLSANISETSSNKTSSADTQKVAIIELTD
GWYAVKAQLDPPLLAVLKNGRLTVGQKIILHGAELVGSPDACTPLE
APESLMLKISANSTRPARWYTKLGFFPDPRPFPLPLSSLFSDGGNVGC
VDVIIQRAYPIQRMEKTSSGLYIFRNEREEEKEAAKYVEAQQKRLEA
LFTKIQEEFEEHEENTTKPYLPSRALTRQQVRALQDGAELYEAVKN
AADPAYLEGYFSEEQLRALNNHRQMLNDKKQAQIQLEIRKAMESAE
QKEQGLSRDVTTVWKLRIVSYSKKEKDSVILSIWRPSSDLYSLLTEGK
RYRIYHLATSKSKSKSERANIQLAATKKTQYQQLPVSDEILFQIYQPR
EPLHFSKFLDPDFQPSCSEVDLIGFVVSVVKKTGLAPFVYLSDECYNL
LAIKFWIDLNEDIIKPHMLIAASNLQWRPESKSGLLTLFAGDFSVFSAS
PKEGHFQETFNKMKNTVENIDILCNEAENKLMHILHANDPKWSTPT
KDCTSGPYTAQIIPGTGNKLLMSSPNCEIYYQSPLSLCMAKRKSVSTP
VSAQMTSKSCKGEKEIDDQKNCKKRRALDFLSRLPLPPPVSPICTFVS
PAAQKAFQPPRSCGTKYETPIKKKELNSPQMTPFKKFNEISLLESNSIA
DEELALINTQALLSGSTGEKQFISVSESTRTAPTSSEDYLRLKRRCTTS
LIKEQESSQASTEECEKNKQDTITTKKYI

FIG. 11C

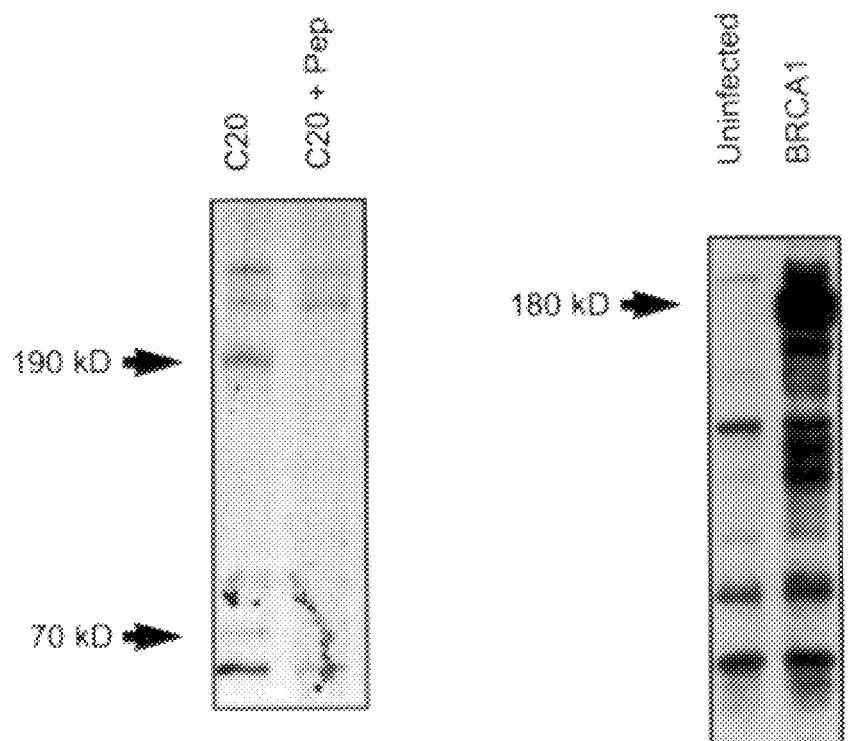
FIG. 13
FIG. 14
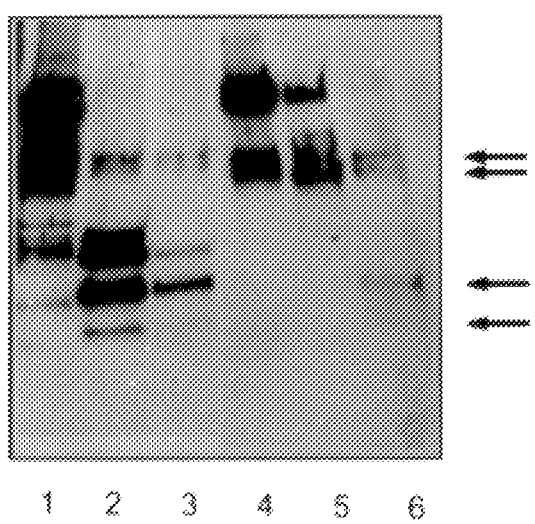
FIG. 15

CHARACTERIZED BRCA1 AND BRCA2 PROTEINS AND SCREENING AND THERAPEUTIC METHODS BASED ON CHARACTERIZED BRCA1 AND BRCA2 PROTEINS

This invention was made in part from government support under Grant No. ES-00267 from the National Institutes of Health, National Institute of Environmental Health Sciences; and under Grants R29-CA62161, T32-CA09592, F32-CA66293 and R01-CA27632 from the National Institutes of Health. The government has certain rights in the invention.

UTILITY STATEMENT

Both the BRCA1 and BRCA2 proteins have been identified as inhibitors of the growth of breast and ovarian cancer cells and thus a DNA segment encoding the BRCA1 protein and a DNA segment encoding the BRCA2 protein can be used in a gene therapy methods for the treatment of breast cancer and for the treatment of ovarian cancer.

The discovery and purification of the BRCA1 protein has broad utility. The purified BRCA1 protein can be used in treating breast or ovarian cancer. Moreover, since it has been determined that the BRCA1 protein is secreted, the BRCA1 protein can be also be used to identify the BRCA1 receptor. Once the BRCA1 receptor is identified, BRCA1 protein-mimetic agents which act on the receptor can be identified. Such agents are also useful in the treatment of breast and ovarian cancer.

The BRCA2 protein is also a secreted protein and can be used to identify the BRCA2 receptor. Once the BRCA2 receptor is identified, BRCA2 protein-mimetic agents which act on the receptor can be identified. Such agents are also useful in the treatment of breast and ovarian cancer.

ACTIVITY STATEMENT

The BRCA1 gene product is an inhibitor of the growth and proliferation of human breast and ovarian cancer cells. The BRCA1 gene product is a secreted protein, thus indicating that it acts on a receptor to produce this activity.

The BRCA2 protein is an inhibitor of the growth and proliferation of human breast and ovarian cancer cells. The BRCA2 protein is a secreted protein, thus indicating that it acts on a receptor to produce this activity.

BACKGROUND OF THE INVENTION

The present invention relates generally to purified and isolated proteins and DNA molecules; to methods of screening for receptors; and to methods of treatment of ovarian and breast cancer, and more particularly to a purified and isolated BRCA1 protein cleavage products; and to gene therapy methods using the BRCA1 gene and the BRCA2 gene in the treatment of breast and ovarian cancer; and to methods for identifying the receptors of the BRCA1 protein and the BRCA2 protein.

The human breast and ovarian cancer susceptibility gene BRCA1 is mutated in the germline and lost in tumor tissue in hereditary breast and ovarian cancer (Hall et al., 1990, Science 250, 1684–1689; Miki et al., 1995 Science 266, 66–71; Smith et al., 1992; Cornelius et al., 1995, The Breast Cancer Linkage Consortium. Genes Chrom Cancer 13: 203–210).

Despite much excitement with the discovery of BRCA1, mutations were only found in the germline which accounts for only a small minority of breast cancers (Futreal et al., 1994, Science 266, 120–121). In addition, BRCA1 was found to be expressed at the same levels in normal individuals and sporadic breast cancers (Mili et al., 1994, Science 266, 66–71). Thus, the initial excitement over BRCA1 was followed by great disappointment.

The BRCA2 breast and ovarian cancer susceptibility gene has also recently been identified. (Wooster, R., et al., Nature 379: 789–792, 1995).

To date all tumor suppressors discovered encode proteins which are not secreted. Steeg, (review article), 1996, Nature Genetics 12:223. To treat the cancer associated with these tumor suppressors requires expressing the normal protein in the affected cell. Thus, these cancers have not been treatable with extracellular administration of the normal protein encoded by the tumor suppressor gene. For this reason, gene therapy has been proposed as the most likely means to supply a normal functional tumor suppressor protein.

This invention significantly modifies the state of the BRCA art by providing thaT the BRCAs are secreted and thus are amenable to direct therapy or prevention by contacting the BRCA receptor on the cell surface. In addition, the invention provides that BRCA1 is indeed underexpressed in sporadic breast cancer and thus sporadic breast cancer is amendable to therapy and prevention by correcting the BRCA deficiency. Other embodiments are also provided.

SUMMARY OF THE INVENTION

An aspect of this invention concerns a purified and isolated BRCA1 cleavage protein; and biologically functional and structural equivalents thereof.

Another aspect of this invention is that the BRCA1 protein is a secreted tumor suppressor/growth inhibitor protein that exhibits tissue-specific tumor suppression/growth inhibition activity.

Important aspects of the present invention concern isolated DNA segments and recombinant vectors encoding the BRCA1 and the BRCA2 proteins, and the creation and use of recombinant host cells through the application of DNA technology, which express the BRCA1 and BRCA2 proteins.

The present invention concerns DNA segments, isolatable from human breast and ovarian tissue, which are free from genomic DNA and which are capable of conferring tumor suppressor/growth inhibitor activity in a recombinant host cell when incorporated into the recombinant host cell. As used herein, the term "breast or ovarian tissue" refers to normal and cancerous ovarian breast tissues, as exemplified, but not limited to, by HMEC or MCF-7 cell lines. DNA segments capable of conferring tumor suppressor activity may encode complete BRCA1 and BRCA2 proteins, cleavage products and biologically actively functional domains thereof.

As used herein, the term "DNA segment" refers to a DNA molecule which has been isolated free of total genomic DNA of a particular species. Furthermore, a DNA segment encoding a BRCA1 protein or encoding a BRCA2 protein refers to a DNA segment which contains BRCA1 coding sequences or contains BRCA2 coding sequences, yet is isolated away from, or purified free from, total genomic DNA of Homo sapiens. Included within the term "DNA segment", are DNA segments and smaller fragments of such segments, and also recombinant vectors, including, for example, plasmids, cosmids, phage, viruses, and the like.

Similarly, a DNA segment comprising an isolated or purified BRCA1 gene or BRCA2 gene refers to a DNA segment including BRCA1 coding sequences isolated substantially away from other naturally occurring genes or protein encoding sequences or including BRCA2 coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the BRCA1 gene or the BRCA2 gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a BRCA1 protein that includes within its amino acid sequence the amino acid sequence of SEQ ID NO:2. In other particular embodiments, the invention concerns isolated DNA segments and recombinant vectors incorporating DNA sequences which encode a protein that includes within its amino acid sequence the amino acid sequence of the BRCA1 protein corresponding to human breast or ovarian tissue.

In particular embodiments, the invention concerns isolated DNA segments and recombinant vectors incorporating DNA sequences which encode a BRCA2 protein that includes within its amino acid sequence the amino acid sequence of SEQ ID NO:4. In other particular embodiments, the invention concerns isolated DNA segments and recombinant vectors incorporating DNA sequences which encode a protein that includes within its amino acid sequence the amino acid sequence of the BRCA2 protein corresponding to human breast or ovarian tissue.

It will also be understood that this invention is not limited to the particular nucleic acid and amino acid sequences of SEQ ID NOS:1, 2, 3 and 4. Recombinant vectors and isolated DNA segments may therefore variously include the BRCA1 and BRCA2 encoding regions themselves, coding regions bearing selected alterations or modifications in the basic coding region, or they may encode larger polypeptides which nevertheless include BRCA1 or BRCA2 encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in SEQ ID NO:2 or SEQ ID NO:4, and methods of treating breast or ovarian cancer using these DNA segments. Naturally, where the DNA segment or vector encodes a full length BRCA1 or BRCA2 protein, or is intended for use in expressing the BRCA1 or BRCA2 protein, the most preferred sequences are those which are essentially as set forth in SEQ ID NO:1 and SEQ ID NO:3 and which encode a protein that exhibits tumor suppressor activity in human breast and ovarian cancer cells, as may be determined by the breast and ovarian cancer cell growth inhibition experiments, as disclosed herein.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:2 will be sequences which are "essentially as set forth in SEQ ID NO:2". The term "a sequence essentially as set forth in SEQ ID NO:4" has a similar meaning.

In particular embodiments, the invention concerns gene therapy methods that use isolated DNA segments and recombinant vectors incorporating DNA sequences which encode a protein that includes within its amino acid sequence an amino acid sequence in accordance with SEQ ID NO:2 or in accordance with SEQ ID NO:4, SEQ ID NO:2 and SEQ ID NO:4 derived from breast or ovarian tissue from Homo sapiens. In other particular embodiments, the invention concerns isolated DNA sequences and recombinant DNA vectors incorporating DNA sequences which encode a protein that includes within its amino acid sequence the amino acid sequence of the BRCA1 protein from human breast or ovarian tissue, or which encode a protein that includes within its amino acid sequence the amino acid sequence of the BRCA2 protein from human breast or ovarian tissue.

In certain other embodiments, the invention concerns isolated DNA segments and recombinant vectors that include within their sequence a nucleic acid sequence essentially as set forth in SEQ ID NO:1, or a nucleic acid sequence essentially as set forth in SEQ ID NO:3, and methods of treating breast or ovarian cancer using these sequences. The term "essentially as set forth in SEQ ID NO:1" is used in the same sense as described above and means that the nucleic acid sequence substantially corresponds to a portion of SEQ ID NO:1, respectively, and has relatively few codons which are not identical, or functionally equivalent, to the codons of SEQ ID NO:1, respectively. Again, DNA segments which encode proteins exhibiting tumor suppression activity of the BRCA1 and BRCA2 proteins will be most preferred. The term "functionally equivalent codon" is used herein to refer to codons that encode the same amino acid, such as the six codons for arginine or serine, and also refers to codons that encode biologically equivalent amino acids (see FIG. 2). The term "essentially as set forth in SEQ ID NO:3" has a similar meaning.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1 or SEQ ID NO:3, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent BRCA1 and BRCA2 proteins and peptides. Such sequences may rise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test BRCA1 and BRCA2 mutants in order to examine tumor suppression activity at the molecular level.

If desired, one may also prepare fusion proteins and peptides, e.g., where the BRCA1 or BRCA2 coding regions are aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the BRCA1 or BRCA2 gene(s), e.g., in breast or ovarian cancer cells, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a BRCA1 or BRCA2 gene in its natural environment. Such promoters may include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, *Molecular Cloning Laboratory Manual*, 2d Edition. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, a breast selective MMTV promoter and the LXSN promoter, which are more fully described below.

As mentioned above, in connection with expression embodiments to prepare recombinant BRCA1 and BRCA2 proteins and peptides, it is contemplated that longer DNA segments will most often be used, with DNA segments encoding the entire BRCA1 or BRCA2 protein, functional domains or cleavage products thereof, being most preferred. However, it will be appreciated that the use of shorter DNA segments to direct the expression of BRCA1 and BRCA2 peptides or epitopic core regions, such as may be used to generate anti-BRCA1 or anti-BRCA2 antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins may have a minimum coding length on the order of about 5,600 nucleotides for a protein in accordance with SEQ ID NO:2 or a minimum coding length on the order of about 10,300 nucleotides for a protein in accordance with SEQ ID NO:4.

Naturally, the present invention also encompasses DNA segments which are complementary, or essentially complementary, to the sequence set forth in SEQ ID NO:1 or the sequence set forth in SEQ ID NO:4. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of base pairing to codons that encode the same amino acid, such as the six codons for arginine or serine, and also refers to codons that encode biologically equivalent amino acids (See FIG. 2).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 20% and about 50%; or more preferably, between about 50% and about 70%; or even more preferably, between about 70% and about 99%; of nucleotides which are identical to the nucleotides of SEQ ID NO:1 or to the nucleotides of SEQ ID NO:3, will be sequences which are "essentially as set forth in SEQ ID NO:1" and will be sequences which are "essentially as set forth in SEQ ID NO:3". Sequences which are essentially the same as those set forth in SEQ ID NO:1 or as those set forth in SEQ ID NO:3 may also be functionally defined as sequences which are capable of hybridizing to a nucleic acid segment containing the complement of SEQ ID NO:1 or to a nucleic acid segment containing the complement of SEQ ID NO:3 under relatively stringent conditions. Suitable relatively stringent hybridization conditions will be well known to those of skill in the art (Sambrook et al, 1989, Molecular Cloning Laboratory Manual, 2d Edition).

| List of Abbreviations | |
|---|---|
| MCF-7 | An immortalized cell line derived from a metastasis of human breast cancer |
| HMEC | A primary (non-immortalized) cell line derived from breast epithelial cells obtained during reduction mammoplasty |

List of Abbreviations

| | |
|---|---|
| MDA-MB-468 | An immortalized cell line derived from a metastasis of human breast cancer |
| Sf9 | Insect cells widely used in the art of baculovirus vectors |
| cDNA | Complementary DNA obtained from an RNA template |
| DNA | Deoxyribonucleic Acid |
| RT-PCR | Reverse Transcriptase-Polymerase Chain Reaction |

BRIEF DESCRIPTION OF THE DRAWINGS

FIG. 1 lists the C-terminal and N-terminal amino acid sequences [SEQ ID NOs:5, 6, 7] used as antigens to generate antibodies for the purified and isolated BRCA1 protein described herein.

FIG. 2 is a table of the genetic code.

FIG. 4 is a diagram showing sequence alignment of the granin region of selected granin family members compared with BRCA1.

FIG. 5 is a diagram showing sequence alignment of the granin region of selected granin family members compared with BRCA1 and BRCA2.

FIG. 6 is Table I, which shows inherited BRCA1 mutations and type of cancer.

FIG. 7 is Table II, which shows effect of BRCA1 Expression Vectors on growth.

FIG. 8 is Table III, which shows inhibition of tumorigenesis by BRCA1.

FIG. 9 is the sequence of the BRCA1 gene [SEQ ID NO:1].

FIG. 10 is the sequence of the BRCA2 gene [SEQ ID NO:3].

FIG. 11 is the sequence of the BRCA2 protein [SEQ ID NO:4].

FIG. 13 is an immunoprecipitation/immunoblot analysis of MDA-MB-468 cell lysates with C-19 antisera.

FIG. 14 is a C-20 immunoblot analysis of recombinant Baculovirus produced BRCA1 (marked by arrow) compared with uninfected Sf9 cells (Control).

FIG. 15 is a V8 Protease Map of Native and Recombinant BRCA1.

DESCRIPTION OF THE PREFERRED EMBODIMENT

Figure 3:
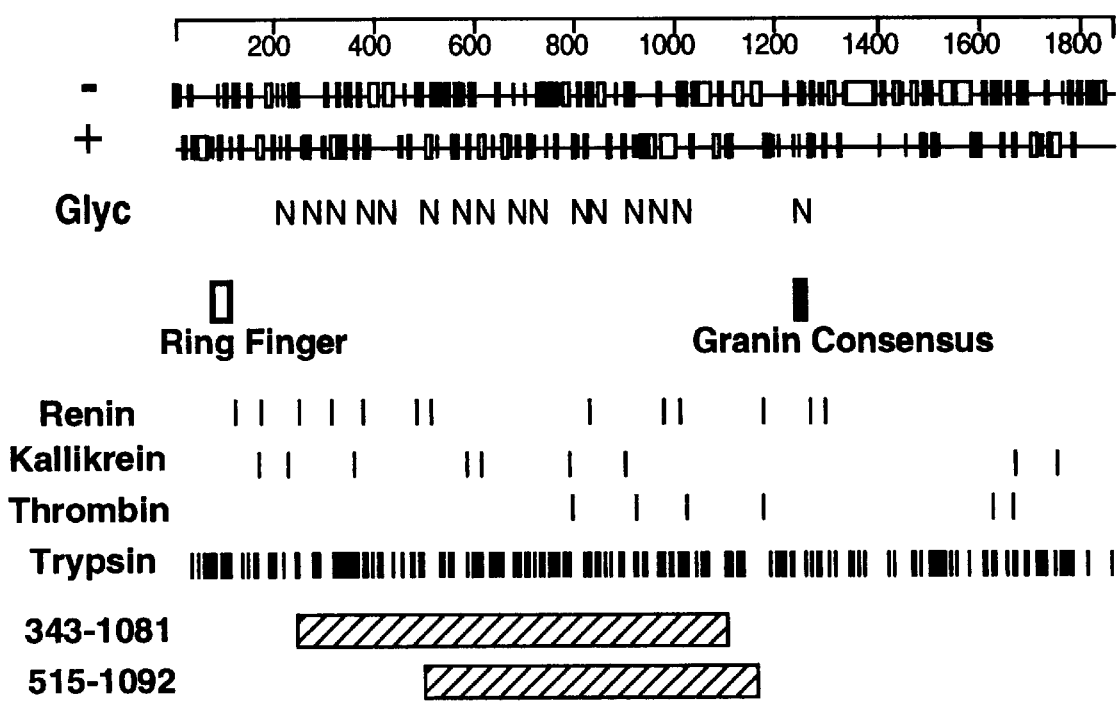
FIG. 3 is a diagram showing structural features of the human BRCA1 protein [SEQ ID NO:2] covering 1864 amino acids.

For the purposes of the subsequent description, the following definitions will be used:

Nucleic acid sequences which are "complementary" are those which are capable of base-pairing according to the standard Watson-Crick complementarity rules. That is, that the larger purines will always base pair with the smaller pyrimidines to form only combinations of Guanine paired with Cytosine (G:C) and Adenine paired with either Thymine (A:T) in the case of DNA or Adenine paired with Uracil (A:U) in the case of RNA.

"Hybridization techniques" refer to molecular biological techniques which involve the binding or hybridization of a probe to complementary sequences in a polynucleotide. Included among these techniques are northern blot analysis, southern blot analysis, nuclease protection assay, etc.

"Hybridization" and "binding" in the context of probes and denatured DNA are used interchangeably. Probes which are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher must be the degree of complementarity and/or the longer the probe.

"Probe" refers to an oligonucleotide or short fragment of DNA designed to be sufficiently complementary to a sequence in a denatured nucleic acid to be probed and to be bound under selected stringency conditions.

"Label" refers to a modification to the probe nucleic acid that enables the experimenter to identify the labeled nucleic acid in the presence of unlabeled nucleic acid. Most commonly, this is the replacement of one or more atoms with radioactive isotopes. However, other labels include covalently attached chromophores, fluorescent moieties, enzymes, antigens, groups with specific reactivity, chemiluminescent moieties, and electrochemically detectable moieties, etc.

"Tissuemizer" describes a tissue homogenization probe.

"PCR technique" describes a method of gene amplification which involves sequenced-based hybridization of primers to specific genes within a DNA sample (or library) and subsequent amplification involving multiple rounds of annealing, elongation and denaturation using a heat-stable DNA polymerase.

"RT-PCR" is an abbreviation for reverse transcriptase-polymerase chain reaction. Subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase produced by *Thermus aquaticus* for its amplification action.

"Nuclease protection assay" refers to a method of RNA quantitation which employs strand specific nucleases to identify specific RNAs by detection of duplexes.

"In situ hybridization of RNA" refers to the use of labeled DNA probes employed in conjunction with histological sections on which RNA is present and with which the labeled probe can hybridize allowing an investigator to visualize the location of the specific RNA within the cell.

"Cloning" describes separation and isolation of single genes.

"Sequencing" describes the determination of the specific order of nucleic acids in a gene or polynucleotide.

The term "BRCA1 targeted growth inhibitor agent", as used herein and in the claims, is defined as the BRCA1 protein characterized herein, whether isolated and purified directly from a natural source such as mammalian ovarian or breast cells, or produced using recombinant methods; the targeted growth inhibitor having the biological activity of tumor suppression and/or growth inhibition activity in mammalian breast or ovarian cancer cells and which binds the BRCA1 receptor; and the term "BRCA1 targeted growth inhibitor agent" also including biologically functional equivalents of the BRCA1 protein characterized herein, the term biologically functional equivalent defined herein to include, among others, proteins and protein fragments in which biologically functionally equivalent amino acids have been inserted and peptidomimetics.

The term "BRCA2 targeted growth inhibitor agent" is used herein as "BRCA1 targeted growth inhibitor agent" above but applies to BRCA2.

The term "homology" describes a mathematically based comparison of sequence similarities which is used to identify genes or proteins with similar functions or motifs.

The term "cleavage product" is defined as a polypeptide fragment produced from the targeted growth inhibitor described above by natural proteolytic processes. Preferably such a cleavage product will have biological activity including, but not limited to, tumor suppression and/or growth inhibition activity in mammalian breast or ovarian cancer cells. This term also includes such polypeptide fragments when produced via recombinant techniques and also includes biological functional equivalents of such fragments, the term biologically functional equivalent defined herein to include, among others, proteins in which biologically functionally equivalent amino acids have been inserted and peptidomimetics.

The term "granin box domain" is defined as the consensus granin box domain of amino acids set forth in FIGS. 3 and 5.

The term "recombinant host cell" is defined as a single cell or multiple cells within a cell line which are capable of undergoing genetic manipulation through well-known and art recognized techniques of transformation, transfection, transduction and the like. Examples of contemplated recombinant host cells include, but are not limited to, cell lines derived from normal or cancerous mammalian breast or ovarian tissue, other eukaryotic cells, and microorganisms. Specific examples of recombinant host cells described herein include Sf9 cells and HMEC cells.

The phrase "substantially identical to the carboxyl terminus of an amino acid sequence as essentially set forth in SEQ ID NO:2" is defined as an amino acid sequence including amino acids identical to the C-terminal amino acids in the amino acid sequence set forth in SEQ ID NO:2, or biologically functional equivalents of these amino acids. Preferred examples of the amino acid sequences are set forth in FIG. 1.

EXAMPLE 1

BRCA1 Encodes a 190 kDa Protein Expressed in Breast Epithelial Cells

As an initial step in the biochemical characterization of the BRCA1 gene product, antibodies were developed and the expression, localization, and function of BRCA1 protein were studied. These studies demonstrate that BRCA1 is a secreted, selectively growth inhibitory and represents a new member of the granin gene family.

Figure 12:
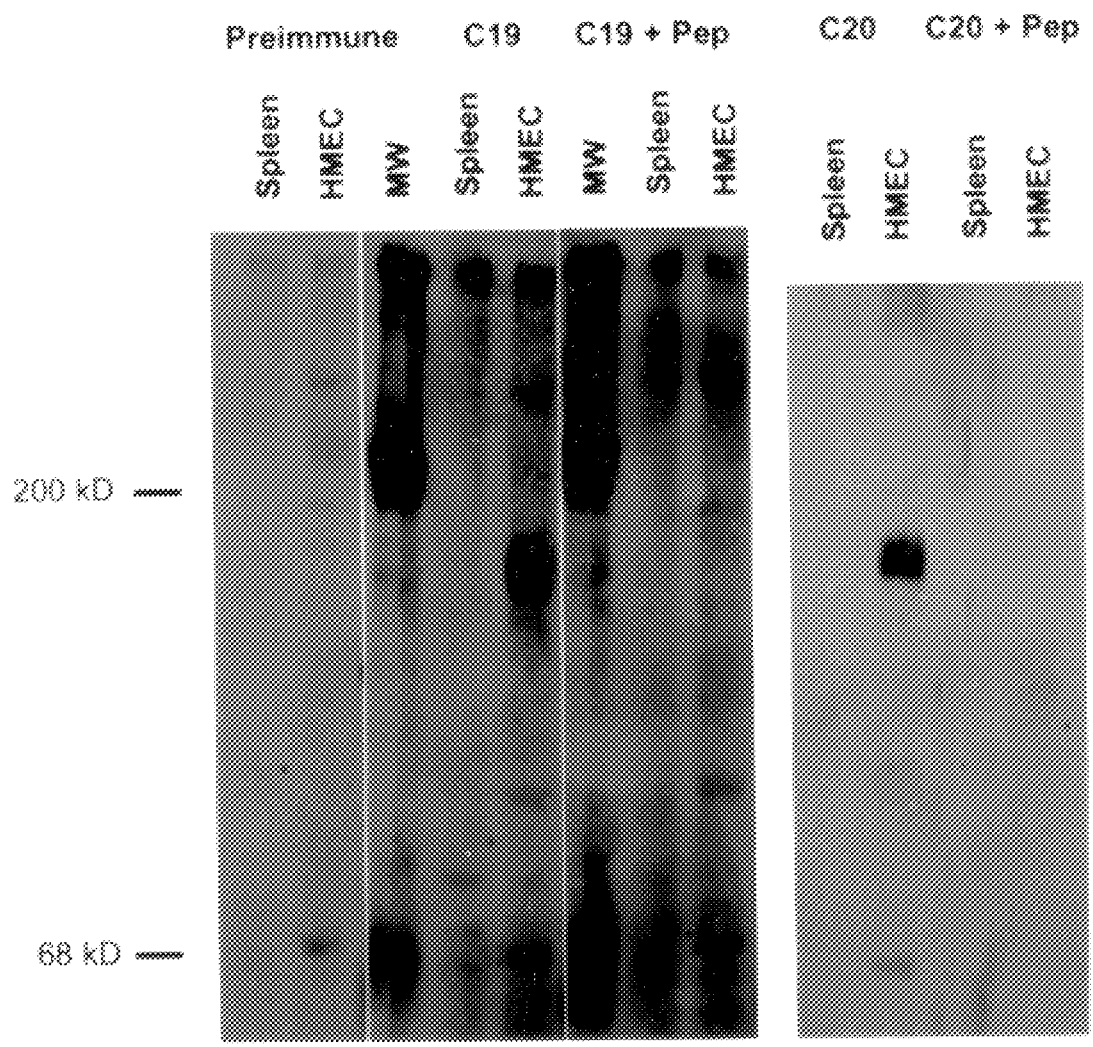
FIG. 12 is an immunoblot analysis of spleen and HMEC cell whole cell lysates probed with preimmune, immune, and immune plus peptide for C-19 antisera and C-20 affinity purified antibody and antibody plus peptide.

To enable BRCA1 protein expression studies a polyclonal rabbit antisera was raised against a peptide from the C-terminal portion of the predicted BRCA1 protein [SEQ ID NO:2]. This peptide corresponded to the last 19 C-terminal amino acids (C-19) [SEQ ID NO:5], which is listed in FIG. 1. The results produced by this antibody, which are more fully described below, were confirmed with antibodies against peptides from the last 20 C-terminal amino acids (C-20) [SEQ ID NO:6] and from the first 20 N-terminal amino acids (D-20) [SEQ ID NO:7] of the predicted BRCA1 protein [SEQ ID NO:2]. These antibodies were purchased from Santa Cruz Biotechnology, Santa Cruz, CA, and the peptide sequences are also are listed in FIG. 1. A search of the SWISS PROT protein sequence database for the N-terminal and C-terminal 20 amino acid peptides at the 60% homology level revealed no entries other than BRCA1. Initially these antisera were screened using Western blot analysis of whole cell lysates from normal human mammary epithelial cells (HMEC-Clonetics, (Stampfer et al., 1980, *Growth of Normal Human Mammary Cells in Culture.* 16, 415–425)) and normal human spleen. Spleen was chosen as a negative control because Northern analysis demonstrated no expression of BRCA1 in spleen (Miki et al., 1994, *Science* 266, 66–71). The results of the experiments with the C-terminal antibodies were obtained with an immunoblot analysis of spleen and HMEC cell whole cell lysates probed with preimmune, immune, and immune plus peptide for C-19 antisera and C-20 affinity purified antibody and antibody plus peptide (FIG. 12). An immunoreactive band that is blocked by the addition of corresponding peptide is present at 190 kDa in the HMEC cells for both the C-19 and C-20 anti-peptide antisera. Note that the C-19 blot has been probed with immune serum diluted 1:200 and that the C-20 blot has been probed with affinity purified antibody. No specific immunoreactivity is detected in the C-19 preimmune sera, and as expected no specific bands are detected in the spleen whole cell lysate by either C-19 or C-20. Several non-specific bands are present in the immune sera that do not block with the addition of peptide, but affinity purified C-20 antibody exhibits minimal non-specific cross reactivity. A minor band at approximately 70 kDa is identified, but appears to block with peptide indicating that this band represents a processed C-terminal fragment of the 190 kDa band. Similar studies were performed on antisera from three separate rabbits, raised against the C-terminal 19 peptide, and in each case, essentially similar results were seen, with some variation in the non-specific bands among individual rabbits, but all three react with a band at approximately 190 kDa that is not present in preimmune serum and is blocked with peptide.

A number of normal tissues and breast cancer cell lines were surveyed for the immunoreactive 190 kDa protein and the majority exhibited a decreased relative expression of BRCA1 in comparison to HMEC cells. The cell line MDA-MB-468 exhibited a very high level of BRCA1 expression, but the majority of other cells tested showed very low to absent (MCF-7, MB-157, MB-361) levels of expression. To analyze the ability of the antisera to immunoprecipitate the 190 kDa protein, radiolabelled whole cell lysates from MDA-MB-468 cells were immunoprecipitated with C-20 antisera (FIG. 13). The 190 kDa and 70 kDa species in the HMEC lane are blocked with the addition of peptide, but a number of non-specific bands including a 220 kDa species (Chen, et al, 1995, *Science* 270:789–791) are not blocked. Immunoprecipitation of MDA-MB-468 cells demonstrates a 190 kDa protein that is not present in the peptide addition control. In addition, the 70 kDa species is immunoprecipitated with antibody and blocked by the addition of peptide. It is noted that several other bands are identified that are not blocked with peptide, in particular at 205 and 220 kDa. This indicates that despite the 207 kDa size predicted from the BRCA1 coding sequence, the 205 kDa and 220 kDa bands do not represent BRCA1. These results are consistent with the 185 kDa estrogen-regulated protein reported by Gudas (Gudas, et al. 1995, *Cancer Res.*, 55:4561–4565) but differ from the 220 kDa ubiquitous protein reported by Chen, particularly because the 220 kDa protein does not block with peptide.

While these results strongly suggested that the antisera was specific for a 190 kDa protein present in breast epithelial cells, further experiments were performed to demonstrate that this protein corresponded to BRCA1. A concern was that the full length coding sequence for BRCA1 predicts a protein of 207 kDa molecular weight and the protein that the antisera recognized was definitely less than 200 kDa, and approximately 190 kDa.

Figure 16:
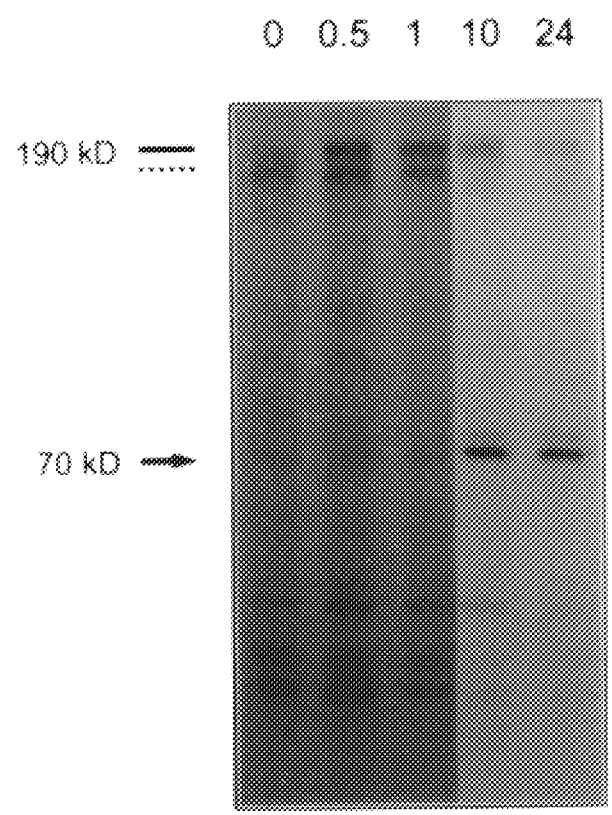
FIG. 16 is a Pulse-Chase Analysis of MDA-MB-468 Cells.

Therefore to confirm that the antisera recognized BRCA1 a full length BRCA1 cDNA was constructed and cloned into the baculovirus transfer vector pAcSG2 (PharMingen). This plasmid was subsequently utilized to produce recombinant BRCA1 baculovirus by co-transfection and homologous recombination. The antisera was then tested for its ability to recognize baculovirus expressed recombinant BRCA1. The results of these experiments were that the antibodies recognize a 180 kDa band in the BRCA1 recombinant virus infected cell lysates that is not present in the no infection control (FIG. 14). The recognition of this band is blocked by the addition of peptide and it is not present in the preimmune serum blot. To verify that the native 190 kDa protein and the recombinant 180 kDa protein were in fact the same protein, peptide mapping of the 190 kDa band from MDA-MB-468 cells and the 180 kDa protein from BRCA1 recombinant Sf9 cell lysates was performed as described in the methods. The digests were loaded onto a 4–20% gradient SDS-PAGE gel and immunoblotted with C-20 (FIG. 16). In FIG. 15, Lanes 1 through 3 and 4 through 6 represent increasing concentrations of V8 protease. The arrows at right indicate four identical sized molecular weight bands in lanes 3 and 6 that document that recombinant BRCA1 and the 190 kD band from MDA-MB-468 cells are identical proteins. This data confirmed that the antibodies are specific for BRCA1 protein. The difference in molecular weight between the recombinant and native protein is likely to be due to differences in glycosylation. These experiments demonstrate that the immunoreactive band completely blocks with peptide and is not present in control wild type virus infected lysates.

To characterize the 70 kDa species a pulse-chase experiment was performed that demonstrates that this band is a proteolytic fragment derived from the 190 kDa form. MDA-MB-468 cells were starved in cysteine and methionine deficient media and then pulsed with 35S labelled cysteine and methionine containing media with 3% dialyzed fetal bovine serum for three hours. The cells were then chased in L-15 media with 10% fetal bovine serum for increasing periods of time and harvested in lysis buffer. The lysates were immunoprecipitated, electrophoresed and the dried gel was autoradiographed (FIG. 16). In this experiment, it was shown that BRCA1 is initially synthesized as a 185 kDa form that is subsequently processed to a 190 kDa species. This represents glycosylation of the newly synthesized protein. Initially, no 70 kDa form is present, but co-incident with the appearance of the fully glycosylated form, the 70 kDa form appears. Subsequently, as the 190 kDa signal decreases with time post-labelling, the 70 kDa band increases in intensity. These findings indicate that the 70 kDa band is a proteolytic fragment, or cleavage product, of the 190 kDa protein. Other cleavage products were also isolated, including a 110 kDa species and a 130 kDa species.

Having demonstrated that the antibodies recognize BRCA1 protein, immunohistochemical analysis on formalin fixed, paraffin-embedded normal breast tissue were performed to analyze the distribution of BRCA1 within the breast. The results demonstrated that luminal epithelial cells (Page and Anderson, 1987, *Nature Genetics* 2, 128–131) within breast acini and ducts stain positively but myoepithelial cells and supporting stromal cells did not stain. No staining was observed when either primary antibody was deleted or peptide was added to the incubation. Staining was present diffusely throughout the cytoplasm and was not localized to the nucleus.

In summary, then, a 190 kDa protein was demonstrated to be the BRCA1 gene product by a number of independent criteria: 1) three different antibodies directed against two different regions of the predicted gene product react specifically in western blots and are blocked by appropriate peptides; 2) The C-20 antibody specifically immunoprecipitates the protein; 3) The C-20 antibody specifically recognizes the recombinant protein expressed in baculovirus; 4) Peptide mapping experiments definitely demonstrate that the 190 kDa protein recognized in MDA-MB-468 cells and the recombinant virus infected Sf9 cells are the same. Immunohistochemical studies indicate that BRCA1 protein is present in the luminal epithelial cells which are presumed be the cells of origin for the vast majority of hereditary and sporadic breast cancers.

EXAMPLE 2

Figure 17:
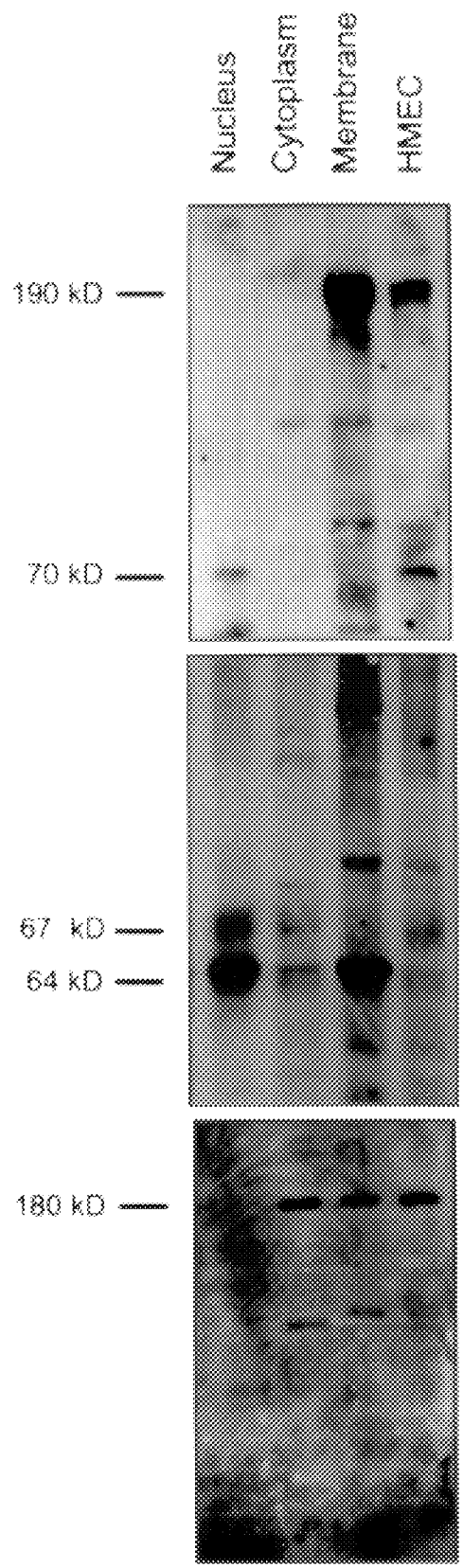
FIG. 17 is an immunoblot analysis of nuclear, cytoplasmic and membrane fractions of HMEC cells paired with corresponding whole cell lysate and probed for BRCA1 (C-19), c-myc, and PDGFR beta.
Figure 18:
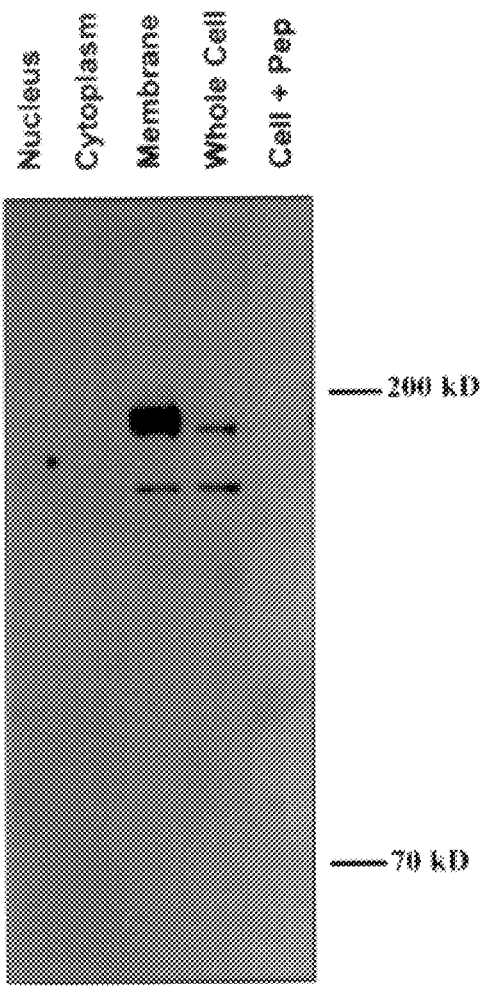
FIG. 18 is an immunoblot analysis of nuclear, cytoplasmic and membrane fractions of HMEC cells paired with corresponding whole cell lysate and probed with D-20 N-terminal antibody plus and minus peptide.
Figure 19:
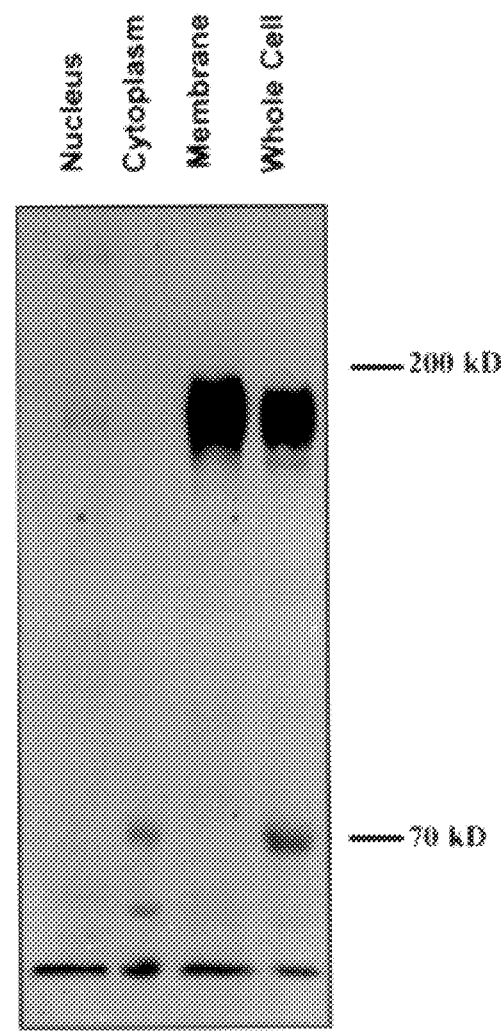
FIG. 19 is an immunoblot analysis of nuclear, cytoplasmic and membrane fractions of MDA-MB-468 cells paired with corresponding whole cell lysate probed with C-20 antibody.

BRCA1 is Predominately Localized in the Membrane Fraction of Breast Epithelial Cells Due to the immunohistochemical studies, a series of experiments to determine more precisely the localization of BRCA1 within the cell was initiated. The first such experiment was a cell fractionation experiment designed to segregate nuclear, cytoplasmic, and membrane compartments of HMEC cells. As shown in FIG. 17, the cell fractionation analysis included immunoblot analysis of nuclear, cytoplasmic and membrane fractions of HMEC cells paired with corresponding whole cell lysate and probed for BRCA1 (C-19 antibody), c-myc, and PDGFR beta; and identical fractions as above probed with D-20 N-terminal antibody plus and minus peptide (FIG. 18). The cell fractionation analysis also included immunoblot analysis of nuclear, cytoplasmic and membrane fractions of MDA-MB-468 cells paired with corresponding whole cell lysate probed with C-20 antibody (FIG. 19). The results of this cell fractionation experiment clearly demonstrate that the 190 kDa species of BRCA1 is present and greatly enriched for in the membrane fraction of HMEC cells. Essentially no 190 kDa BRCA1 could be detected in either the nuclear or cytoplasmic fractions, although the 70 kDa protein is present in the nuclear fraction. As a control for the fractionation procedure parallel blots were probed with antisera for c-myc and platelet-derived growth factor receptor beta (PDGFR). These blots demonstrated that the nuclear fraction is greatly enriched for the 67 and 64 kDa c-myc proteins (Alexandrova et al., 1995, *Mol.Cell.Biol.* 15:5188–5195) and the cytosolic and membrane fractions show PDGFR as expected. These results were confirmed with the antibody to the N-terminal portion of BRCA1 (D-20). This antibody detects the 190 kDa form of BRCA1 and an additional 165 kDa species in HMEC cells. Both of these bands are blocked with the addition of peptide and are present in the membrane fraction exclusively. Note that this antibody does not detect the 70 kDa species identified in the C-terminal peptide blots.

To investigate the possibility that subcellular localization of BRCA1 might be altered in malignant breast cells, fractionation studies on MDA-MB-468 cells that express high levels of BRCA1 protein were performed (FIG. 19). These studies demonstrated that in parallel with findings in HMEC cells the 190 kDa form of BRCA1 is also greatly enriched in the membrane fraction of MDA-MB-468 cells. In contrast to HMEC cells however, there appears to be a small amount of the 190 kDa species in the nuclear fraction of MDA-MB-468 cells. It is also noted that in contrast to HMEC cells, the 70 kDa species is present exclusively in the cytosolic fraction of MDA-MB-468 cells.

To further investigate the precise subcellular localization of BRCA1 confocal microscopy utilizing the affinity purified C-20 antisera was employed. These experiments indicated that the C-20 antibody exhibits diffuse granular staining that is predominately localized in the cytoplasm of HMEC cells. The nucleus and Golgi compartment were localized in these experiments, and this provided the capability to identify co-localization of BRCA1 in both the nucleus and Golgi complex. Simultaneous triple staining for the nucleus, Golgi complex and BRCA1 again demonstrated a predominant granular cytoplasmic distribution for BRCA1, with co-localization in both the nucleus and Golgi complex. These findings are in agreement with the cell fractionation studies of HMEC cells, despite the inability of those studies to detect the 190 kDa BRCA1 form in the nucleus, because the 70 kDa form was present in the nuclear fraction and would be expected to be detected by C-terminal antibody.

In summary, then, the above studies demonstrate that the majority of BRCA1 protein is non-nuclear and membrane-associated. Cell fractionation studies show the 190 kDa BRCA1 protein resides primarily in the membrane-associated fraction, but the p70 protein is localized in the nucleus of normal breast cells and the cytoplasm of MB-486 breast cancer cells. The distinct membrane-associated and nuclear localization patterns result from the unprocessed and the 70 kDa processed form, respectively. There is definite co-localization with the 190 kDa BRCA1 protein and the Golgi marker supporting the trafficking of BRCA1 through the Golgi prior to its packaging into secretory granules.

EXAMPLE 3

BRCA1 is a Member of the Granin Family of Secretory Proteins and Localizes to Secretory Vesicles Having identified BRCA1 as being present in the membrane fraction of breast epithelial cells and having a large granular cytoplasmic pattern of staining, a homology search of BRCA1 was performed, focusing on motifs that might explain the apparent membrane localization of BRCA1. A search on the SWISS PROT database of the MacDNAsis PRO v3.0 software package was performed and several features of biologic and functional importance were identified, as shown in FIG. 3. In FIG. 3, (−) and (+) mark location of charged residues and glyc shows potential N-linked glycosylation sites. RING finger and granin (amino acids 1214–1223) consensus are shown by open and closed boxes. Predicted protease cleavage sites for renin, kallikrein, thrombin, and trypsin are shown as thin lines. Regions deleted in the internal deletion mutants are shown as shaded boxes below (343–1081 and 515–1092).

The SWISS PROT search revealed that BRCA1 has homology to the granin consensus site as shown in FIG. 4. In FIG. 4, consensus sequence is shown in bold at the bottom. Sequences are human unless otherwise stated. The granin motif spans amino acids 1214–1223 of BRCA1. Note that human BRCA1 completely satisfies the ten amino acid granin consensus and exhibits the other structural features of the family. The probability that BRCA1 would exhibit a perfect granin consensus by chance alone is 0.0018 (or one in 555). The rationale for this calculation is given at the bottom of FIG. 4.

Figure 20:
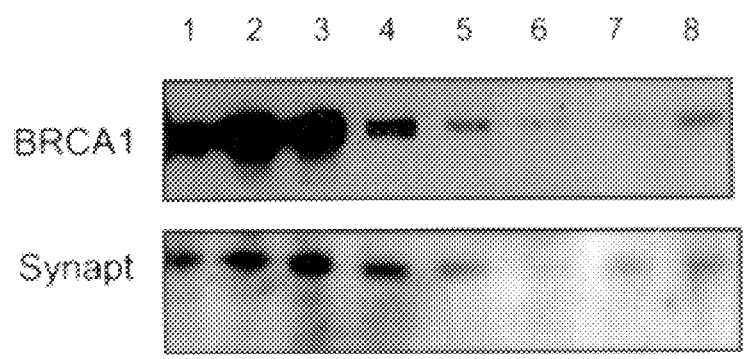
FIG. 20 depicts assay of MDA-MB-468 cell fractions produced by sucrose gradient for synaptophysin and BRCA1 immunoreactivity.

To investigate the hypothesis that BRCA1 behaves biochemically as a granin, the following series of experiments were executed. To document the presence of BRCA1 in secretory vesicles, cell organelles from MDA-MB-468 cells were fractionated by sucrose gradient centrifugation and the fractions were assayed for synaptophysin (a highly specific marker for secretory vesicles) and BRCA1 immunoreactivity. As seen in FIG. 20, coordinate expression of BRCA1 and synaptophysin was noted, which indicates the co-localization of these proteins in secretory vesicles. These results document the co-localization of synaptophysin and BRCA1 in fractions expected to contain secretory vesicles.

Figure 21:
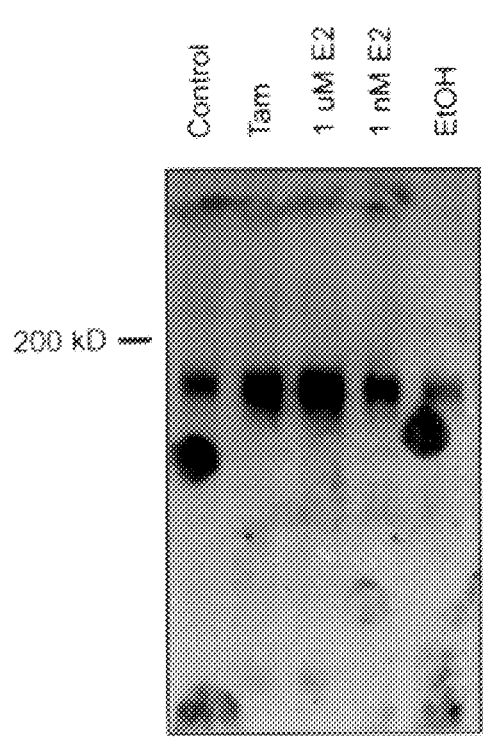
FIG. 21 depicts estrogen regulation of BRCA1 protein.

Since granins have been shown to be regulated by estrogens (Fischer-Colbrie et al., 1991, *J. Neuroendocrinol.* 121, 125–130) HMEC cells were stimulated with estrogen and tamoxifen and increased expression of BRCA1 was demonstrated, as reported previously by others (Gudas, et al. 1995, *Cancer Res.,* 55:4561–4565; Marquis et al., 1995, *Nature Genetics* 11, 17–26; Lane et al., 1995, *Genes & Development* 9, 2712–2722). The dose response was consistent with estrogen regulation of BRCA1 expression. As presented in FIG. 21, cell lysates from HMEC cells treated for 24 hours with tamoxifen (TAM), indicated concentrations of estrogen (E2), or ethanol control (ETOH). Note E2 dosage effect.

Figure 22:
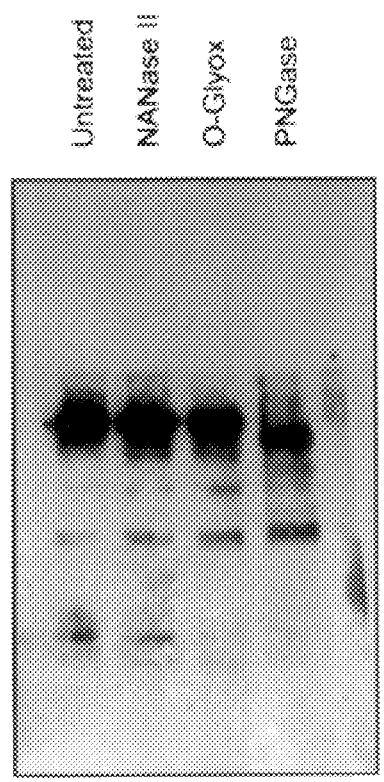
FIG. 22 depicts N-Linked glycosylation of BRCA1 protein.

HMEC cell membrane fractions were then treated with sequential deglycosylation enzymes (NANase II>O-Glycosidase DS>PNGase F to remove a2–3 and a2–6 N-acetylneuraminic acid, serine/threonine glycosylation (FIG. 22). N-linked glycosylation). A shift of protein following PNGase F treatment was noted, confirming N-linked glycosylation. Thus, BRCA1 exhibits N-linked glycosylation as predicted from the sequence analysis and shows little Ser/Thr glycosylation.

Figure 23:
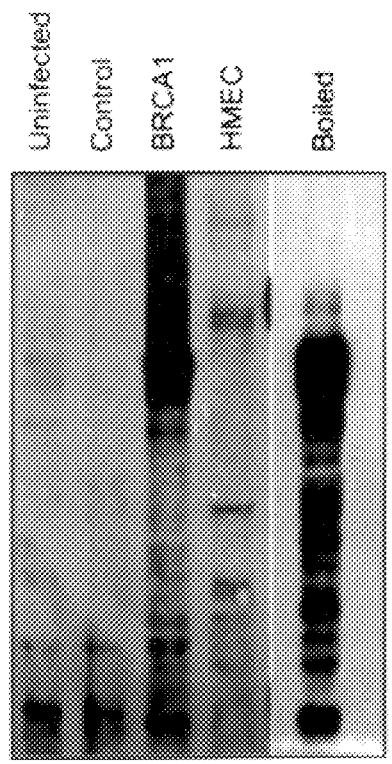
FIG. 23 depicts heat solubility of BRCA1 protein.

In addition, a heat stable fraction was prepared from recombinant baculovirus BRCA1 in a modification of the procedure of Thompson et al., (1992b), *Mol. Brain Res.* 12, 195–202, where cell pellets of infected Sf9 cells were sonicated, centrifuged, boiled for five minutes, and then centrifuged again. This heat soluble fraction was then analyzed by immunoblotting. BRCA1 remained soluble after boiling, which is characteristic of granins. As seen in FIG. 23, the immunoblots included cell lysates from uninfected Sf9 cells, wild-type infected cells (control), BRCA1 infected cells, HMEC cells, and heat soluble fraction of Baculovirus produced recombinant BRCA1. Recombinant BRCA1 remains soluble after boiling.

Figure 24:
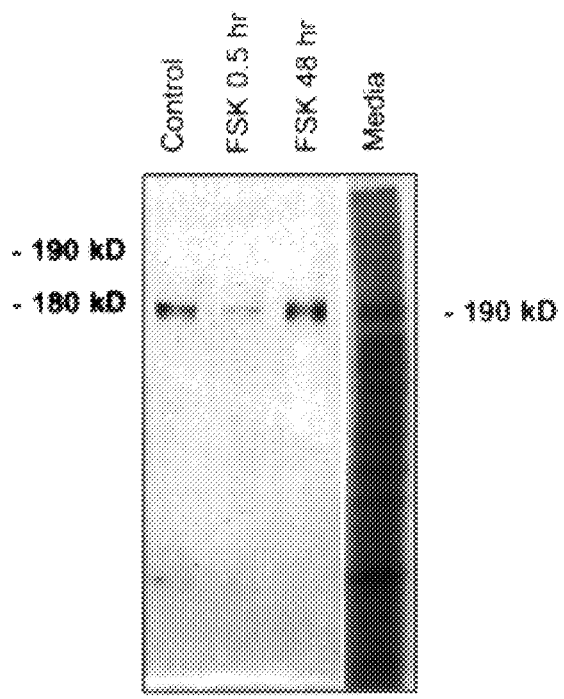
FIG. 24 is a Western blot of HMEC cell lysates: control; stimulated with 10 mM forskolin 0.5 hours post stimulation; and 48 hours post stimulation and also includes radioimmunoprecipitation of BRCA1 From conditioned media (lane 4).

Additionally, HMEC cells were treated with 10 mM forskolin and a marked decrease in BRCA1 levels in whole cell lysates after 0.5 hours of treatment and a return to normal levels 48 hours later was observed. This data is consistent with forskolin stimulated release of secretory granules and subsequent replenishment. As seen in FIG. 24, the Western blot of HMEC cell lysates included: control, stimulated with 10 mM forskolin 0.5 hours post stimulation and 48 hours post stimulation. The Western blot also included a lane marked Media, which showed the results of radioimmunoprecipitation of 24 hour conditioned media from 35S-labelled MDA-MB-468 cells. These results indicate the presence of BRCA1 protein at 190 kDa. Media was supplemented with aprotinin, PMSF, leupeptin, and pepstatin.

To confirm that BRCAI is in fact secreted MDA-MB-468 cells were metabolically labelled and the 190 kDa band was immunoprecipitated from a 24 hour collection of labelled conditioned media. Finally, immunogold electron microscopy was performed with C-20 antibody on MDA-MB-468 cells and it was demonstrated that BRCA1 immunoreactivity localizes to secretory vesicles. These secretory vesicles were primarily located in the apical cytoplasm and were often found at the tips of microvilli extending into the extracellular space. A vesicle actively undergoing secretion was identified. These findings confirm that BRCA1 is a member of the granin family of secretory proteins.

In summary, then, BRCA1 has a granin box which shows 100% homology to the consensus (Huttner et al., 1991, Trends Biochem. Sci. 16, 27–30) and has the expected number of acidic residues and predicted isoelectric point of granin family members. Additional evidence that BRCA1 is a granin includes 1) Presence in secretory vesicle fractions; 2) Induction by estradiol; 3) Glycosylation which occurs on secretory proteins as they are transported through the rough endoplasmic reticulum (Kornfeld & Komfeld, 1985, Annu. Rev. Biochem. 54, 631–664); 4) Solubility of boiled protein, a biochemical feature of the granin family; 5) Release of BRCA1 protein by forskolin induction of regulated secretion; and 6) localization in secretory vesicles by immunogold electron microscopy.

As more fully described below, internal deletions which eliminate key structural elements and glycosylation sites destroy growth inhibition and tumor suppression, thus indicating that BRCA1 tumor suppression and growth inhibition are mediated through its granin-like properties.

EXAMPLE 4

Normal BRCA1 inhibits growth of breast and ovarian cancer cells

Experiments to determine whether BRCA1 could function as a growth inhibitor or tumor suppressor were performed. Analysis of BRCA1 protein levels in human breast cancer cell lines indicated that MCF-7 cells had little or no BRCA1 protein. Analysis of MCF-7 cells for allelic loss at markers in the BRCA1 region indicates loss of at least 2 Mb including the BRCA1 region on one chromosome 17q21, and that the coding sequence of the retained BRCA1 allele was normal. Sal I Tinkered BRCA1 cDNA was cloned into the unique Xho I site of the retroviral vector LXSN for transfection studies. To rule out trivial effects on localization or stability, two in-frame internal deletion mutants were constructed which eliminated much of the region of BRCA1 containing acidic residues and putative glycosylation sites (D343–1081 and D515–1092), but preserved the granin homology region. Two termination codon mutants were constructed which resulted in predicted proteins containing 1835 and 340 amino acids.

Table I shows that transfection of the LXSN vector or the internal deletion mutants resulted in similar numbers of G418-resistant stable clones in a number of human cell lines. Transfection of LXSN-BRCA1 into MCF-7 cells or Caov-4 ovarian cancer cells resulted in fewer clones which could not be expanded beyond 30 cells per clone. Some of these clones can be expanded in an enriched growth media containing GMSA, 10% fetal calf serum and 5 ng/ml EGF. This growth inhibitory effect of BRCA1 was confined to these cell types since fibroblast, lung cancer cells, and colon cancer cells were not growth inhibited by LXSN-BRCA1. The 340-amino acid truncated protein did not inhibit growth of any cell line. However, the 1835 amino acid protein significantly inhibited growth of ovarian cancer cells but not breast cancer cells. This indicates that distinct mechanisms mediate growth inhibition of ovarian cancer cells and breast cancer cells and that this difference depends on the length of the truncated protein.

EXAMPLE 5

Ovarian cancer susceptibility is differentially associated with protein truncations 5' of the granin region To determine whether the differential effects of short versus long truncated proteins on Caov-4 ovarian cancer cells were paralleled in human patients, the relative frequency of ovarian versus breast cancer among 166 patients in a series inheriting BRCA1 mutations was calculated (Table II). Mutations inherited by 19 patients were nonsense alterations leading to transcript instability and no mutant protein. Mutations inherited by 13 patients were missense alterations in the RING finger leading to complete but aberrant protein. All other mutations were protein-truncating mutations at sites throughout the gene. The difference in ovarian and breast cancer distribution between the two groups was statistically significant: ovarian cancer formed a significantly lower proportion (2%) of the cancers in patients with mutant proteins that would include the granin motif compared to the proportion (25%) of cancers in patients with more severely truncated proteins ($X2=11.12$, $P<0.001$). This result is consistent with the observation that the site of BRCA1 mutation is associated with relative susceptibility to ovarian versus breast cancer (Gayther et al., 1995, Nature Genet 11: 428–433). The analysis of Gayther et al., indicated that the correlation between genotype and phenotype was better described by a "change point" in the BRCA1 sequence than by a linear trend in locale of mutation. The granin consensus motif at codons 1214–1223 is well within the confidence limit for the estimated location (codons 1235–1243) of the optimal change point in that analysis.

EXAMPLE 6

BRCA1 Inhibits Breast but not Colon Tumorigenesis

BRCA1 gene transfer into MCF-7 cells inhibits tumorigenesis employing retroviral gene transfer. Supernatants containing $5 \times 10^7$ vector particles from LXSN and LXSN-BRCA1 PA317 producer clones were used to transduce $5 \times 10^7$ MCF-7 cells or OK3 colon cancer cells in culture which were subsequently injected into the flanks of six nude mice for each vector. The cells were not treated with G418 before injection because prior G418 treatment inhibits tumorigenesis in this model, but southern blots have demonstrated that 70–80% of MCF-7 cells are transduced by this protocol. Four weeks after injection there were MCF-7 tumors in 5/6 LXSN control mice but no tumors in LXSN-BRCA1 mice. Retroviral transduction by BRCA1 had no effect on colon tumor formation (Table III, FIG. 8). Tumors ultimately developed in all of the control mice and 4/6 LXSN-BRCA1 mice but the tumors in LXSN-BRCA1 mice were significantly smaller (LXSN: 569 grams+60; LXSN-BRCA1: 60 grams+24) as illustrated in Table III, FIG. 8. Molecular analysis of tumor RNAs showed that the vector neo gene was present and expressed in all MCF tumors and that BRCA1 was detectable only in the four LXSN-BRCA1 transduced tumors. Because the ex vivo transduction strategy could inhibit tumor establishment but not necessarily inhibit growth of already established tumors, whether in vivo injection of LXSN-BRCA1 into established MCF-7 intraperitoneal tumors could inhibit the growth rate and improve survival was tested. This experimental approach results in retroviral vector integration into 20–40% of tumor cells. The results showed that while all five of the mice given the mutant BRCA1 retrovirus died in less than two weeks, the five mice injected with LXSN-BRCA1 survived from 15–41 days because the injection decreased the size and sequelae of the intraperitoneal tumors (Table III, FIG. 8).

The above studies were confirmed with stable transfectants expressing BRCA1. Using an enriched growth media MCF-7 transfectants containing the transferred BRCA1 gene were obtained. Although these clones grow at 1/3 the rate of mutant BRCA1 transfected clones in vitro, whether they would form tumors in nude mice was determined. Three distinct clones transfected with D343–1081 and four distinct clones transfected with BRCA1 (five mice per clone) were injected with the MCF-7 transfectants. The results show that 0/20 mice injected with BRCA1 transfectants developed tumors while 13/15 mice injected with mutant BRCA1 transfectants developed tumors, providing confirmation that BRCA1 inhibits tumorigenesis in nude mice (Table III). RT-PCR analysis demonstrated that the transfectants expressed the expected transfected BRCA1 or mutant BRCA1 mRNA.

Lactation is the most important secretory process in the breast and is defining for mammals. Indeed, the human breast is unique in that it does not fully differentiate until the first pregnancy and active lactation is followed by involution (Battersby et al., 1994, *Histopathology* 15:415–433). Thus during each lactation, cell numbers must be increased with the end of proliferation coinciding with the gain of secretory function. Following cessation of lactation the cell numbers must decrease to allow breast involution. Pairing secretion feedback with cell proliferation and growth inhibition mechanisms is reasonable and to be expected in this setting. The identification of BRCA1 as a member of the granin family of secreted proteins indicates that it functions as a novel type of tumor suppressor gene.

Analysis of BRCA1 mutations shows that near full-length proteins do not protect against breast cancer, but far less often lead to ovarian cancer (Table II). Analysis of transfection experiments shows that near full-length BRCA I proteins do not inhibit growth of breast cancer cells but do inhibit growth of ovarian cancer cells. This indicates that the mechanism of tumor suppression by BRCA1 differs for breast versus ovarian cancer.

Pregnancy and lactation are important protective factors for breast cancer. Although the epidemiologic basis of this is well-demonstrated, molecular correlates are lacking. The demonstration that BRCA1 mRNA is induced during mouse pregnancies and this work showing a secretory function for BRCA1 link a tumor suppressor gene with a epidemiologically-defined tumor suppression activity, early pregnancy.

EXAMPLE 7

Method of Screening for BRCA1 or BRCA2 Receptor

That BRCA1 is secreted has important implications for lactation and growth regulation of normal and malignant breast cells. The secreted BRCA1 protein acts on a cell surface receptor. The interaction between the BRCA1 protein and the receptor produces the beneficial effects, i.e. tumor suppression, in the target breast or ovarian tissue. Methods for isolating the BRCA1 receptor follow. The BRCA2 receptor can be similarly isolated.

Baculovirus BRCA1 can be purified from the insect cells with the C20 antibody and then labelled with radioactive iodine by standard methods. Cys61Gly and termination codon mutant BRCA1 proteins are prepared and labelled as a control. The labelled BRCA1 can then be used to perform binding studies to identify cells with BRCA1 receptors using Scatchard analysis; and to perform cross-linking studies which demonstrate the BRCA1 receptor(s) on polyacrylamide gels. These initial characterization methods are used to identify cells with high and low numbers of BRCA1 receptor(s) for purification and isolation studies. Once a cell line with high levels of BRCA1 receptor has been identified, then the protein is purified by the following approaches:

Approach A: Biochemical purification

The cell line which expresses high levels of BRCA1 receptor is lysed and the protein from cell lysates or membrane preparations is purified by gel filtration followed by purification of the receptor with a column containing the BRCA1 ligand bound to a solid phase such as sepharose. The purified receptor protein can then be microsequenced and the gene cloned using degenerate oligonucleotides derived from the protein sequence.

Approach B:

Ligand is radiolabeled with 125I and then used to screen cell lines or tissues for specific binding by Scatchard analysis. Once such binding is identified, a cDNA library is constructed from that tissue or cell line and transfected into a cell line that does not exhibit specific binding. These transfected cells are then screened for newly acquired specific binding which indicates they have been transfected with a construct containing the gene for the BRCA1 receptor. Plasmid DNA from positive clones is then isolated and sequenced for identification. This single construct is then transfected back into the null cells to verify that binding of ligand is mediated by the transfected gene. (Kluzen et al, *Proc Natl Acad Sci USA* 89:4618–4622 (1992).

Alternatively, chimeric BRCA1 and immunoglobulin Fc molecules can be constructed. (LaRochelle et al, *J Cell Biol* 129:357–366 (1995)). These chimeric molecules are then be used to screen for binding to BRCA1 receptor on whole cells via flow cytometry. Alternatively, due to the presence of the immunoglobulin component of the molecule, cell lysates are screened by immunoblotting or by immunoprecipitation of metabolically labelled cells. This technique can identify BRCA1 binding proteins by a variety of different methods. Peptide digests of the identified proteins are then generated so that the peptides can be sequenced and the whole molecule cloned by a degenerative oligonucleotide approach.

EXAMPLE 8

Screen for BRCA1 Protein Mimetic Agents

Classical methods for identifying compounds which activate receptors are greatly facilitated by the prior identification of the receptor. However, knowledge of ligand structure domains and deletion and minimization methods allow the identification of active ligand mimetic drugs without first finding the receptor. As more fully described above, certain regions of the BRCA1 gene have been deleted to show which regions are essential for growth inhibitory activity. These studies can be continued in a systematic manner, revealing the regions of the molecule needed for its key activities. Upon identification of a small protein that can produce growth inhibition, systematic structural and functional analysis of the minimal protein can be performed as per the methods described in Li, et al., *Science* 270: 1657, 1995. Drugs can then be screened for and/or synthesized which mimic the peptide structure and consequently produce the desired effect.

Thus, provided also is a method of screening a compound for tumor suppressor activity comprising contacting the compounds with the BRCA1 or BRCA2 receptor, a compound which binds the receptor indicating a compound having potential tumor suppressor activity. Binding can be detected by well-known methods in the art, including, among others, radioimmunoassays and fluorescence assays.

EXAMPLE 9

Therapy method for ovarian cancer using the BRCA1 Gene

Viral vectors containing a DNA sequence that codes for a protein having an amino acid sequence as essentially set forth in SEQ ID NO:2 can be constructed using techniques that are well known in the art. This sequence includes the BRCA1 protein. Viral vectors containing a DNA sequence essentially as set forth in SEQ ID NO:1 (the BRCA1 gene) can be also constructed using techniques that are well known in the art. Retroviral vectors such as the LXSN vector described above, adenoviral vectors, or adeno-associated viral vectors are all useful methods for delivering genes into ovarian cancer cells. The viral vector is constructed by cloning the DNA sequence essentially as set forth in SEQ ID:1 into a retroviral vector such as an ovarian selective vector. Most preferably, the full-length (coding region) cDNA for BRCA1 is cloned into the retroviral vector. The retroviral vector would then be transfected into virus producing cells in the following manner: Viruses are prepared by transfecting PA317 cells with retroviral vector DNAs which are purified as described in Wong et al., 1988, *Proceeding of the UCLA Symposia on Biology of Leukemias and Lymphomas.*, Golde D. (ed.), Alan R. Liss, Inc. 61:553–566. Following transfection, the PA317 cells are split and then treated with G418 until individual clones can be identified and expanded. Each clone is then screened for its titer by analyzing its ability to transfer G418 resistance (since the retroviral vector contains a Neomycin resistance gene). The clones which have the highest titer are then frozen in numerous aliquots and tested for sterility, presence of replication-competent retrovirus, and presence of mycoplasma. Methods generally employed for construction and production of retroviral vectors have been described above and in Miller, et al., 1990, *Methods in Enzym.* 217:581–599.

Once high titer viral vector producing clones have been identified, then patients with ovarian cancer can be treated by the following protocol: Viral vector expressing BRCA1 is infused into either solid tumors or infused into malignant effusions as a means for altering the growth of the tumor (since it is shown above that the BRCA1 protein decreases the growth rate of ovarian cancer cells). Because viral vectors can efficiently transduce a high percentage of cancer cells, the tumors will be growth inhibited.

EXAMPLE 10

The protein encoded by the BRCA2 breast and ovarian cancer susceptibility gene is a granin and a secreted tumor suppressor The protein encoded by the BRCA2 breast and ovarian cancer susceptibility gene (Wooster, R., et al., *Nature* 379: 789–792, 1995) includes a domain similar to the granin consensus at the C-terminus of the protein. As seen in FIG. 5, the sequence at amino acids 3334–3344 of Genbank locus HUS43746 matches six of the seven constrained sites of the granin consensus. BRCA2 and murine BRCA1 differ from the consensus at the same site. The granin motif in BRCA2 lies at the extreme C-terminal end of the protein, a locale characteristic of a known granin. This indicates that the protein encoded by the BRCA2 gene is also a secreted growth inhibitor. Use of both the BRCA1 and BRCA2 genes offer the opportunity for a unified approach to the treatment of inherited and sporadic breast cancer. Accordingly, the examples set forth above depicting the treatment of ovarian cancer, are equally applicable to the BRCA2 gene and the BRCA2 protein.

The identification of BRCA1 and BRCA2 as granins indicated that there is a granin superfamily of which consists of the subfamilies of chromogranins (chromogranins A, B and C); secretogranins (secretogranins III–V) and the BROCAgranins (BRCA1, BRCA2 and other tumor suppressor genes). This classification of granins into these subclasses is based on greater similarities within the subfamilies than with the superfamily as a whole. For example, the chromogranins share an additional region of homology besides the granin consensus and exhibit similar expression patterns; the secretogranins show less homology to the granin consensus than either chromogranins or BROCAgranins; the BROCAgranins BRCA1 and BRCA2 are cancer susceptibility genes, contain additional regions of homology, and are significantly larger (two-twenty times larger) than other granins described to date.

Thus, the invention provides in Example 3 and in this example a granin box consensus sequence shown in FIG. 5. Thus, provided is a family of proteins which share the consensus sequence that are tumor suppressor genes. BRCA1 and BRCA2 are members of this family. Other members may be identified and purified as tumor suppressor genes by genetic methods, by DNA-based searches for granin homology; or by cloning and characterization of granins in ovarian or breast cancer cells by biochemical methods. Such biochemical methods include the isolation and purification of proteins from secretory vesicles or Golgi by physical isolation methods, followed by development of antibodies to determine which proteins, followed by cloning of genes for secreted proteins after protein sequencing and cloning with degenerate oligonucleotide primers. A example of this method is described in Colomer et al., 1996, *J. Biological Chemistry* 271:48–55. Thus, other BROCAgranins are contemplated to be within the scope of this invention.

EXAMPLE 11

Gene Therapy method using the BRCA2 Gene

Viral vectors containing a DNA sequence that codes for a protein having an amino acid sequence as essentially set forth in SEQ ID NO:4 can be constructed using techniques that are well known in the art, and as are more fully described above. This sequence includes the BRCA2 protein. Viral vectors containing a DNA sequence essentially as set forth in SEQ ID NO:3 (the BRCA2 gene) can be also constructed using techniques that are well known in the art. Retroviral vectors, adenoviral vectors, or adeno-associated viral vectors are all useful methods for delivering genes into breast cancer cells. An excellent candidate for use in breast cancer gene therapy is a Moloney-based retroviral vector with a breast selective MMTV promoter (Wong et al., 1988, *Proceeding of the UCLA Symposia on Biology of Leukemias and Lymphomas.*, Golde D. (ed.), Alan R. Liss, Inc. 61:553–566). The viral vector is constructed by cloning the DNA sequence essentially as set forth in SEQ ID NO:3 into a retroviral vector such as a breast selective vector. Most preferably, the full-length (coding region) cDNA for BRCA2 is cloned into the retroviral vector. The retroviral vector is then transfected into virus producing cells in the following manner: Viruses are prepared by transfecting PA317 cells with retroviral vector DNAs which are purified as described in Wong et al. Following transfection, the PA317 cells are split and then treated with G418 until individual clones can be identified and expanded. Each clone is then screened for its titer by analyzing its ability to transfer G418 resistance (since the retroviral vector contains a Neomycin resistance gene). The clones which have the highest titer are then frozen in numerous aliquots and tested for sterility, presence of replication-competent retrovirus, and presence of mycoplasm. The methods generally employed for construction and production of retroviral vectors have been described above and in Miller, et al., 1990, *Methods in Enzym.* 217:581–599.

Once high titer viral vector producing clones have been identified, then patients with breast cancer can be treated by the following protocol: Viral vector expressing BRCA2 protein is infused into either solid tumors or infused into malignant effusions as a means for altering the growth of the tumor. Because viral vectors can efficiently transduce a high percentage of cancer cells, the tumors will be growth inhibited.

EXAMPLE 12

Gene Transfer Using Liposomes

An alternative method of gene therapy using the BRCA1 and BRCA2 gene includes the use of liposome to deliver the DNA into the cells. By this method, the above described LXSN-BRCA1 plasmid would be incubated with a liposome preparation such as cationic liposomes and then the DNA liposome mix is added to cells or injected into an animal or patient. Generally, the liposome transfection method is of a lower efficiency than viral gene transfer methods. This method is useful because the BRCA1 and BRCA2 proteins are secreted proteins. Thus, if only a few percent of cells take up the DNA-liposome combination, it is likely that enough BRCA1 or BRCA2 protein will be produced and secreted from these cells to growth inhibit other cells. Liposomal transfection of nucleic acids into host cells is described in U.S. Pat. Nos. 5,279,833 and 5,286,634, the contents of each of which are herein incorporated by reference.

EXAMPLE 13

Anti-Sense Inhibition of the Production of BRCA1 Protein

The antisense inhibition of BRCA1 is described as follows. Antisense methods were used to demonstrate that BRCA1 expression inhibits cell growth. Unmodified 18 base deoxyribonucleotide complementary to the BRCA1 translation initiation site were synthesized and added to cultures of primary mammary epithelial cells (Stampfer et al. 1980, In Vitro 16: 415–425 (1980)) or MCF-7 breast cancer cells (Soule and McGrath, 1980, *Cancer Letters* 10, 177–189 (1980)).

The morphologic appearance of the cell lines was not noticeably changed by addition of antisense oligonucleotide, but the proliferative rate was faster. Incubation of cells with 40 uM anti-BRCA1 oligonucleotide produced accelerated growth of both normal and malignant mammary cells, but did not affect the growth of human retinal pigmented epithelial cells. An intermediate dose of anti-BRCA1 oligonucleotide produced a less pronounced but significant increase in cell growth rate. This was not a toxic effect of the oligonucleotide since a control "sense" oligomer with the same GC content did not increase the proliferation rate, and because an addition of a 10 fold excess of sense oligomer to the anti-BRCA1 oligomer reversed the growth activation.

Thus, antisense inhibition of BRCA1 accelerates the growth of breast cancer cells. Because chemotherapy is most effective in cancer cells which are rapidly dividing, it is possible then to treat breast or ovarian cancer by accelerating growth of cancer cells by antisense inhibition of BRCA1 protein expression and by treating with chemotherapeutic drugs using standard chemotherapy protocols.

EXAMPLE 14

Biological Functional Equivalent Proteins and Peptides

Modification and changes may be made in the structure of the BRCA1 protein and the BRCA2 protein, or in cleavage products of these proteins, and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules or receptors, specifically the BRCA1 or BRCA2 receptor. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of the BRCA 1 and BRCA2 proteins or peptides (or underlying DNA) without appreciable loss of their biological utility or activity.

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate= Glu (E); Glutamine=Gln (Q); Glycine=Gly (G); Histidine= His (H); Isoleucine=Ile (I); Leucine=Leu (L); Lysine=Lys (K); Methionine=Met (M); Phenylalanine=Phe (F): Proline= Pro (P); Serine=Ser (S); Threonine=Thr (T); Tryptophan= Trp (W); Tyrosine=Tyr (Y); Valine=Val (V).

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with this invention.

It is also well understood that where certain residues are shown to be particularly important to the biological or structural properties of a protein or peptide, e.g., residues in active sites, such residues may not generally be exchanged. This is the case in the present invention where an exchange in the granin box domain may alter the fact that the BRCA1 and BRCA2 proteins are secreted.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine, and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for another amino acids having a similar hydropathic index or score and still retain a similar biological activity. In making changes based upon the hydropathic index, the substitution of amino acids whose hydropathic indices are within ±1 are particularly preferred, and those within ±2 is preferred, those which are within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent, and in particular, an immunologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids hose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Kyte & Doolittle, *J. Mol. Biol.*, 157:105–132, 1982; Hopp, U.S. Pat. No. 4,554,101

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modelling and chemical design known to those of skill in the art. It will be understood that all such sterically similar constructs fall within the scope of the present invention.

U.S. Pat. No. 4,554,101 (Hopp, incorporated herein by reference) teaches the identification and preparation of epitopes from primary amino acid sequences on the basis of hydrophilicity. Through identify epitopes from within an amino acid sequence such as the BRCA1 and BRCA2 sequences disclosed herein (SEQ ID NOs:2, 4). These regions are also referred to as "epitopic core regions".

Numerous scientific publications have been devoted to the prediction of secondary structure, and to the identification of epitopes, from analyses of amino acid sequences (Chou & Fasman, 1974a,b; 1978a,b 1979). Any of these may be used, if desired, to supplement the teachings of Hopp in U.S. Pat. No. 4,554,101. Moreover, computer programs are currently available to assist with predicting antigenic portions and epitopic core regions of proteins. Examples include those programs based upon the Jameson-Wolf analysis (Jameson & Wolf, 1998; Wolf et al., 1988), the program PepPlot® (Brutlag et al., 1990; Weinberger et al., 1985), and other new programs for protein tertiary structure prediction (Fetrow & Bryant, 1993).

EXAMPLE 15

Treatment of Breast or Ovarian Cancer using Purified BRCA1 or BRCA2 Protein

Alternatively, breast or ovarian cancer be treated by the administration of a therapeutically effective amount of the BRCA1 or BRCA2 protein via an efficient method, such as injection into a tumor. A therapeutically effective amount can be determined by one having ordinary skill in the art using well-known protocols.

It is important to note that breast and ovarian cancer cells have surface receptors which must be contacted by the BRCA1 or BRCA2. Thus, the BRCA1 or BRCA2 protein, an active fragment, or a small molecule mimetic binds directly to a receptor on the surface of the breast or ovarian cancer cells.

EXAMPLE 16

Method of Treating Breast or Ovarian Cancer Comprising Introducing the BRCA1 Receptor Gene and the BRCA1 protein into a Breast or Ovarian Cancer Cell The loss of the BRCA1 receptor in breast and ovarian cancer cells will lead to the proliferation and tumorigenesis in these cells. Thus, breast and ovarian cancer can be treated by introducing the BRCA1 receptor gene into breast or ovarian cancer cells using the gene therapy methods described above. This step will be followed by the administration of a therapeutically effective amount of the BRCA 1 protein so that the BRCA1 protein contacts a receptor on a surface of the breast or ovarian cells. A therapeutically effective amount can be determined by one having ordinary skill in the art using well-known protocols.

EXAMPLE 17

Method of Preventing Breast or Ovarian Cancer using BRCA1 or BRCA2 Protein

It is a well-established epidemiologic fact that parity and particularly early parity has a protective effect in regards to both breast and ovarian cancer risk. Because of various changes in the structure of society it is now quite common for women to delay childbirth and lose this natural protective effect. Since it is known that BRCA1 is induced in pregnancy and lactation, and it is demonstrated herein that BRCA1 is a secreted growth inhibitor that is specific for breast and ovarian cancer, the protective effect of pregnancy and lactation is due to BRCA1 expression. BRCA1 mediation of this effect for both breast and ovarian cancer presents a variety of strategies that are useful in decreasing breast and ovarian cancer risk, particularly in women that did not have a baby in their first twenty years and thus, were at a higher risk to develop breast or ovarian cancer. Thus, one can use a BRCA to prevent the first occurrence or a recurrence of breast and ovarian cancer. Examples of such strategies are presented below. While examples are provided, such strategies should not be limited to the examples.

BRCA1 protein might be used a chemopreventive agent by introducing BRCA1 directly into the peritoneal cavity of women as the whole protein, as a functional fragment, or as a functional cleavage product. In addition, compounds that induce expression of BRCA1 or activate its receptor, e.g. a small molecule mimetic, could also be introduced. Since BRCA1 is a secreted protein, the introduced BRCA1 will decrease ovarian cancer risk in the same manner that BRCA1 does normally when its expression is induced by pregnancy. The protective effect is also expected where BRCA1 expression is mediated by gene therapy method by either directly or indirectly inducing expression of BRCA1.

A similar rationale can be applied to breast cancer prevention. In this case, the whole BRCA1 protein; a functional fragment or a functional cleavage product thereof; or a pharmacological mimic can be used. In addition, compounds that induce expression of BRCA1 or activate its receptor, e.g. a small molecule mimetic, could also be used. Gene therapy approaches for increasing the expression of BRCA1 in breast directly or indirectly could also be used. Systemic agents that induce expression of BRCA1, or that mimic function and can replace BRCA 1, such a peptidomimetic agent, could also be used. The delivery of such agents could take place by directly instilling the agent within the breast by introducing via the nipple. Finally, an implantable time release capsule can be used in a prevention strategy, either by placing such a capsule in the peritoneum for ovarian cancer, by implant such a capsule into the breast for breast cancer.

Since the BRCA2 protein includes a granin sequences and is also a secreted tumor suppressor protein, similar prevention strategies can be applied using the BRCA2 gene and protein.

Experimental Procedures for Examples 1–6
Tissues and Cell Culture

Cryopreserved primary cell lines (Passage 7) of normal human mammary epithelial (HMEC) cells, were obtained from Clonetics, Inc. The cryovial of HMEC was thawed and subcultured according to the instructions provided, which are a slight modification of published procedures (Stampfer et al, 1980, *Growth of Normal Human Mammary Cells in Culture.* 16, 415–425). Breast cancer cell lines were obtained from American Type Culture Collection (ATCC), Rockville, Md. Sf9 cells were obtained from ATCC.
Antibodies C-terminal 19 peptide fragment was conjugated to keyhole limpet hemacyanin and injected into New Zealand white rabbits along with Freund's adjuvant according to standard protocols. C-20 and D-20 were provided by Santa Cruz Biotechnology. c-myc and PDGFR antibodies were provided by Steve Hann and William LaRochelle, respectively.

Cell Extracts, Immunoblotting, Immunoprecipitation, Northern blotting Cell lysates, immunoblotting, and immunoprecipitation assays were performed according to previously published methods (Jensen et al, 1992, *Biochem.* 31: 10887–10892). RNA was isolated by published methods (Jensen et al, 1994, *Proc Natl Acad Sci USA* 91, 9257–9261) and probed with the T7 labelled EcoRI- Kpn I fragment from exon 11.
Cell Fractionation Studies Cell fractionations were performed according the method of Fazioli, et al (1993, *Mol. Cell. Bio.* 13, 5814–5828). Briefly, cells in T175 flasks were washed twice with cold PBS/0.5 mM sodium vanadate, followed by a single washing in cold isotonic fractionation buffer (FB). Then, cold FB+protease inhibitors (PI) are added to the plates. The plates are incubated for 10 min, scraped, and homogenized with a Dounce tissue homogenizer. The nuclei were gently pelleted (375 g) at 4° C. and the supernatant (cytosolic and plasma membrane fraction) was saved. After washing the nuclear pellet with four aliquots of cold FB+PI+0.1% NP40 followed by centrifugation at 4° C., the nuclei were resuspended in cold FB and 2× lysis buffer +PI. The cytosolic and plasma membrane fraction was then ultracentrifuged (35, 000 g) for 30 min at 4° C. and the supernatant was saved as the cytosolic fraction. The pellet (plasma membrane fraction) was resuspended in FB+PI and solubilized in 2× lysis buffer with PI. Following this, the nuclear and plasma membrane fractions are sonicated on ice for 10 seconds three times. They were then spun at 10,000 g at 4° C., and the supernatant was collected and saved as the soluble nuclear and plasma membrane fractions, respectively.

Confocal Imaging Studies

HMEC cells were plated into 35 mm culture dishes with glass bottom cover slips (Mat-Tek) and allowed to grow to 70% confluency. The cells were then rinsed, fixed in 4.0% paraformaldehyde in phosphate buffered saline at 4° C. (PBS, 0.01M phosphate salts, and 0.15M NaCl, pH 7.6) for ten minutes, and washed and permeabilized in PBS with 0.2% Triton X-100 for two minutes. Cells were blocked with 5% normal donkey serum in PBS. Primary antibodies were diluted in PBS containing 3.0% bovine serum albumin (BSA) and 0.1% Triton X-100 and consisted of rabbit anti-BRCA-1 (vendor) diluted 1:200 and a mouse monoclonal to a Golgi complex antigen (Biogenex; clone 371-4) diluted 1:10. No antibody and antibody to BRCA-1 preadsorbed with the peptide antigen were used as negative controls. Secondary antibodies were from Jackson Immunoresearch and consisted of extensively adsorbed, multiple-labeling grade donkey anti-rabbit-specific IgG conjugated to CY3 (diluted 1:1000) and donkey anti-mouse-specific IgG conjugated to either CY5 (diluted 1:500) or FITC (diluted 1:250). Nuclei were counterstained with YO-PRO1 (Molecular Probes, Inc.) diluted 1:500 for 20 minutes following immunostaining. Double-immunolabeling studies were carried out with all the necessary controls for staining specificity as outlined previously (Jetton et al., 1994, *J. Biol. Chem.* 269, 3641–3654). Following immunostaining, sections were mounted in Aqua-Polymount (Polysciences) and imaged using a Zeiss LSM 410 confocal microscope using the 488/647 and 543 nm lines of an Ar-Kr and He-Ne laser, respectively. Images were optimized using Adobe Photoshop 3.0 then transferred as TIFF files to a Silicon Graphics Indigo where figures were assembled using SGI Showcase and printed using a Tektronix Phaser IISDX color printer.

Glycosylation Analysis

Glycosylation analysis was performed on aliquots of HMEC membrane fractions with the Enzymatic Deglycosylation Kit from Glyko, Inc. according to the manufacturer's recommended protocol, and the samples were immunoblotted and probed with C-20 antibody.

Isolation of Secretory Vesicles

Secretory vesicles were isolated as described (Tooze and Huttner, 1990, *Cell* 60, 837–847) with minor modifications. All steps were performed at 4° C. MDA-MB-468 cells were washed with cold PBS containing protease inhibitors. After centrifugation at 700×g for 5 min, the pellet was resuspended in homogenization buffer (0.25M sucrose, 1 mM EDTA, 1 mM Mg acetate, 10 mM HEPES-KOH, pH 7.2) with protease inhibitors.and centrifuged at 1700×g for 5 min. The pellet was resuspended in 5 times the cell volume of homogenization buffer with protease inhibitors. Cells were passed through a 22 gauge needle 10 times and homogenized with 50 strokes of a Pyrex homogenizer. Unbroken cells and nuclei were pelleted at 1000×g for 10 min. One ml of the postnuclear supernatant was loaded onto a 0.3M–1.2M sucrose gradient (made in 10 mM HEPES-KOH, pH 7.2) with protease inhibitors and centrifuged at 25,000 rpm in a Beckman SW41 rotor for 15 min. One ml fractions were collected from the bottom and fractions 9–12 were pooled and loaded onto a 0.5M–2M sucrose gradient. The gradient was centrifuged at 25,000 rpm in a Beckman SW41 rotor for 16 hours and fractions collected from the bottom. Fractions 4–12 were analyzed by Western blot analysis.

Expression of Recombinant Clones in the Baculovirus Expression System

A full length BRCA1 cDNA containing consensus translation initiation and stop sites was cloned into the baculovirus transfer vector pAcSG2 as a Sal I fragment. Recombinant baculovirus were produced by cotransfecting Sf9 cells with Baculogold (PharMingen) virus DNA and the recombinant vector DNA. The resulting culture supernatants were harvested after four days, screened for homologous recombination by limiting dilution (Jensen et al., 1992, *Biochem.* 31: 10887–10892), and confirmed by dot-blot hybridization using the 32P-labeled, BRCA1 cDNA probe. Recombinant protein was expressed by infecting with high titer virus at multiplicities of infection of 10:1 or greater.

Peptide Mapping

Whole cell lysates from MDA-MB-468 cells and BRCA1 recombinant virus infected Sf9 cells were electrophoresed and the 190 kDa MDA-MB-468 band and 180 kDa BRCA1 recombinant protein were identified by removing one lane for immunoblotting with C-20 antibody. The bands of interest were then cut out of the gel, eluted on Microcon spin columns (Amicon), and digested with increasing amounts of V8 protease. The digests were re-electrophoresed on 4–20% gradient gels and immunoblotted with C-20.

Immunogold electron microscopy MDA-MB-468 cells were trypsinized, washed in PBS, and fixed in 4.0% paraformaldehyde+0.1% glutaraldehyde/PBS (pH 7.4) for 10 minutes on ice. The cell pellet was washed in PBS, dehydrated in a graded series of alcohols, and embedded in LR White resin (medium grade; Polysciences, Inc.). Thin sections were mounted on nickel grids and blocked in PBS+1.0% bovine serum albumin (BSA) for two hours at room temperature. The grids were then incubated overnight in 1.0% BSA supplemented with 0.05% Tween with or without the C-20 antibody at a final dilution of 1:200. The grids were then washed in PBS/0.05% Tween and incubated in a 1:100 dilution of a goat anti-rabbit-gold conjugate (15 nm size; Electron Microscopy Sciences) for one hour at room temperature. The grids were washed as above, rinsed in distilled water and lightly counterstained with saturated aqueous uranyl acetate and lead citrate, and imaged with a Hitachi H-800 transmission electron microscope.

Gene Transfer Methods and Nude Mice Studies

MCF-7 cells were transfected by calcium phosphate coprecipitation for cell growth studies, but were transduced with retroviral stocks from PA317 producer clones for the nude mice studies as described in the results. Cultured MCF-7 cells were transduced in vitro and then injected subcutaneously into the left flank of 4 week old female nu/nu mice containing slow-release estrogen pellets (Soule et al., 1980, *Cancer Letters* 10, 177–189). Tumor size was determined weekly and animals were autopsied at 8 weeks after injection for determination of tumor weight and RT-PCR analysis for gene expression (Thompson et al., 1995, *Nature Genetics* 9, 444–450). For evaluation of effects of BRCA1 and mutant retroviral vectors on established tumors, $10^7$ MCF-7 cells were injected intraperitoneally and the animals were injected intraperitoneally with high titer retroviral vector stock ($10^7$ virions) once palpable tumors were identified.

What is claimed is:

1. A method to reduce the growth of an epithelial ovarian tumor in a mammal, comprising: injecting into the intraperitoneal cavity of said mammal, at the site of said epithelial ovarian tumor, a retroviral construct comprising BRCA1 cDNA encoding a functionally active BRCA1 polypeptide operably linked to a promoter, wherein said BRCA1 polypeptide is expressed in said epithelial ovarian tumor at a level and for a period of time sufficient to reduce the growth of said epithelial ovarian tumor.

2. A method according to claim 1 wherein the mammal is human.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
      ( A ) LENGTH: 5712
      ( B ) TYPE: nucleic acid
      ( C ) STRANDEDNESS: double
      ( D ) TOPOLOGY: linear ( i i ) MOLECULE TYPE: cDNA to mRNA ( i i i ) HYPOTHETICAL: no ( i v ) ANTI-SENSE: no ( v ) ORIGINAL SOURCE:
      ( A ) ORGANISM: Homo sapiens
      ( C ) INDIVIDUAL ISOLATE:
      ( D ) DEVELOPMENTAL STAGE: adult
      ( F ) TISSUE TYPE: female breast
      ( G ) CELL TYPE: ductal carcinoma in situ, invasive
             breast cancer and normal breast tissue
      ( H ) CELL LINE: not derived from a cell line
      ( I ) ORGANELLE: no ( v i i ) IMMEDIATE SOURCE:
      ( A ) LIBRARY: cDNA library derived from human
      ( B ) CLONE: obtained using published sequence ( v i i i ) POSITION IN GENOME:
      ( A ) CHROMOSOME/SEGMENT: unknown
      ( B ) MAP POSITION: unknown
      ( C ) UNITS: unknown ( i x ) FEATURE:
      ( A ) NAME/KEY: BRCA1
      ( B ) LOCATION: GenBank accession no. U14680
      ( C ) IDENTIFICATION METHOD: microscopicallydirected
             sampling and nuclease protection assay
      ( D ) OTHER INFORMATION: gene encoding BRCA1 protein ( x ) PUBLICATION INFORMATION:
      ( A ) AUTHORS: Miki, Y., et. al.
      ( B ) TITLE: A strong candidate gene for the breast and
             ovarian cancer susceptibility gene BRCA1.
      ( C ) JOURNAL: Science
      ( D ) VOLUME: 266
      ( E ) PAGES: 66-71
      ( F ) DATE: 1994
      ( K ) RELEVANT RESIDUES IN SEQ ID NO:1:

( x i ) SEQUENCE DESCRIPTION: SEQ ID NO:1:

```
agctcgctga gacttcctgg accccgcacc aggctgtggg gtttctcaga taactgggcc              60
cctgcgctca ggaggccttc accctctgct ctgggtaaag ttcattggaa cagaaagaa             119 atg gat tta tct gct ctt cgc gtt gaa gaa gta caa aat gtc att aat             167
Met Asp Leu Ser Ala Leu Arg Val Glu Glu Val Gln Asn Val Ile Asn
1               5                   10                  15 gct atg cag aaa atc tta gag tgt ccc atc tgt ctg gag ttg atc aag             215
Ala Met Gln Lys Ile Leu Glu Cys Pro Ile Cys Leu Glu Leu Ile Lys
            20                  25                  30 gaa cct gtc tcc aca aag tgt gac cac ata ttt tgc aaa ttt tgc atg             263
Glu Pro Val Ser Thr Lys Cys Asp His Ile Phe Cys Lys Phe Cys Met
        35                  40                  45 ctg aaa ctt ctc aac cag aag aaa ggg cct tca cag tgt cct tta tgt             311
Leu Lys Leu Leu Asn Gln Lys Lys Gly Pro Ser Gln Cys Pro Leu Cys
    50                  55                  60
```

| | | | | | | | | | | | | | | | | |
|---|---|---|---|---|---|---|---|---|---|---|---|---|---|---|---|---|
| aag | aat | gat | ata | acc | aaa | agg | agc | cta | caa | gaa | agt | acg | aga | ttt | agt | 359 |
| Lys | Asn | Asp | Ile | Thr | Lys | Arg | Ser | Leu | Gln | Glu | Ser | Thr | Arg | Phe | Ser | |
| 65 | | | | 70 | | | | | 75 | | | | | | 80 | |
| caa | ctt | gtt | gaa | gag | cta | ttg | aaa | atc | att | tgt | gct | ttt | cag | ctt | gac | 407 |
| Gln | Leu | Val | Glu | Glu | Leu | Leu | Lys | Ile | Ile | Cys | Ala | Phe | Gln | Leu | Asp | |
| | | | | 85 | | | | | 90 | | | | | 95 | | |
| aca | ggt | ttg | gag | tat | gca | aac | agc | tat | aat | ttt | gca | aaa | aag | gaa | aat | 455 |
| Thr | Gly | Leu | Glu | Tyr | Ala | Asn | Ser | Tyr | Asn | Phe | Ala | Lys | Lys | Glu | Asn | |
| | | | 100 | | | | | 105 | | | | | 110 | | | |
| aac | tct | cct | gaa | cat | cta | aaa | gat | gaa | gtt | tct | atc | atc | caa | agt | atg | 503 |
| Asn | Ser | Pro | Glu | His | Leu | Lys | Asp | Glu | Val | Ser | Ile | Ile | Gln | Ser | Met | |
| | | 115 | | | | | 120 | | | | | 125 | | | | |
| ggc | tac | aga | aac | cgt | gcc | aaa | aga | ctt | cta | cag | agt | gaa | ccc | gaa | aat | 551 |
| Gly | Tyr | Arg | Asn | Arg | Ala | Lys | Arg | Leu | Leu | Gln | Ser | Glu | Pro | Glu | Asn | |
| | 130 | | | | | 135 | | | | | 140 | | | | | |
| cct | tcc | ttg | cag | gaa | acc | agt | ctc | agt | gtc | caa | ctc | tct | aac | ctt | gga | 599 |
| Pro | Ser | Leu | Gln | Glu | Thr | Ser | Leu | Ser | Val | Gln | Leu | Ser | Asn | Leu | Gly | |
| 145 | | | | | 150 | | | | | 155 | | | | | 160 | |
| act | gtg | aga | act | ctg | agg | aca | aag | cag | cgg | ata | caa | cct | caa | aag | acg | 647 |
| Thr | Val | Arg | Thr | Leu | Arg | Thr | Lys | Gln | Arg | Ile | Gln | Pro | Gln | Lys | Thr | |
| | | | | 165 | | | | | 170 | | | | | 175 | | |
| tct | gtc | tac | att | gaa | ttg | gga | tct | gat | tct | tct | gaa | gat | acc | gtt | aat | 695 |
| Ser | Val | Tyr | Ile | Glu | Leu | Gly | Ser | Asp | Ser | Ser | Glu | Asp | Thr | Val | Asn | |
| | | | 180 | | | | | 185 | | | | | 190 | | | |
| aag | gca | act | tat | tgc | agt | gtg | gga | gat | caa | gaa | ttg | tta | caa | atc | acc | 743 |
| Lys | Ala | Thr | Tyr | Cys | Ser | Val | Gly | Asp | Gln | Glu | Leu | Leu | Gln | Ile | Thr | |
| | | 195 | | | | | 200 | | | | | 205 | | | | |
| cct | caa | gga | acc | agg | gat | gaa | atc | agt | ttg | gat | tct | gca | aaa | aag | gct | 791 |
| Pro | Gln | Gly | Thr | Arg | Asp | Glu | Ile | Ser | Leu | Asp | Ser | Ala | Lys | Lys | Ala | |
| | 210 | | | | | 215 | | | | | 220 | | | | | |
| gct | tgt | gaa | ttt | tct | gag | acg | gat | gta | aca | aat | act | gaa | cat | cat | caa | 839 |
| Ala | Cys | Glu | Phe | Ser | Glu | Thr | Asp | Val | Thr | Asn | Thr | Glu | His | His | Gln | |
| 225 | | | | | 230 | | | | | 235 | | | | | 240 | |
| ccc | agt | aat | aat | gat | ttg | aac | acc | act | gag | aag | cgt | gca | gct | gag | agg | 887 |
| Pro | Ser | Asn | Asn | Asp | Leu | Asn | Thr | Thr | Glu | Lys | Arg | Ala | Ala | Glu | Arg | |
| | | | | 245 | | | | | 250 | | | | | 255 | | |
| cat | cca | gaa | aag | tat | cag | ggt | agt | tct | gtt | tca | aac | ttg | cat | gtg | gag | 935 |
| His | Pro | Glu | Lys | Tyr | Gln | Gly | Ser | Ser | Val | Ser | Asn | Leu | His | Val | Glu | |
| | | | 260 | | | | | 265 | | | | | 270 | | | |
| cca | tgt | ggc | aca | aat | act | cat | gcc | agc | tca | tta | cag | cat | gag | aac | agc | 983 |
| Pro | Cys | Gly | Thr | Asn | Thr | His | Ala | Ser | Ser | Leu | Gln | His | Glu | Asn | Ser | |
| | | 275 | | | | | 280 | | | | | 285 | | | | |
| agt | tta | tta | ctc | act | aaa | gac | aga | atg | aat | gta | gaa | aag | gct | gaa | ttc | 1031 |
| Ser | Leu | Leu | Leu | Thr | Lys | Asp | Arg | Met | Asn | Val | Glu | Lys | Ala | Glu | Phe | |
| | 290 | | | | | 295 | | | | | 300 | | | | | |
| tgt | aat | aaa | agc | aaa | cag | cct | ggc | tta | gca | agg | agc | caa | cat | aac | aga | 1079 |
| Cys | Asn | Lys | Ser | Lys | Gln | Pro | Gly | Leu | Ala | Arg | Ser | Gln | His | Asn | Arg | |
| 305 | | | | | 310 | | | | | 315 | | | | | 320 | |
| tgg | gct | gga | agt | aag | gaa | aca | tgt | aat | gat | agg | cgg | act | ccc | agc | aca | 1127 |
| Trp | Ala | Gly | Ser | Lys | Glu | Thr | Cys | Asn | Asp | Arg | Arg | Thr | Pro | Ser | Thr | |
| | | | | 325 | | | | | 330 | | | | | 335 | | |
| gaa | aaa | aag | gta | gat | ctg | aat | gct | gat | ccc | ctg | tgt | gag | aga | aaa | gaa | 1175 |
| Glu | Lys | Lys | Val | Asp | Leu | Asn | Ala | Asp | Pro | Leu | Cys | Glu | Arg | Lys | Glu | |
| | | | 340 | | | | | 345 | | | | | 350 | | | |
| tgg | aat | aag | cag | aaa | ctg | cca | tgc | tca | gag | aat | cct | aga | gat | act | gaa | 1223 |
| Trp | Asn | Lys | Gln | Lys | Leu | Pro | Cys | Ser | Glu | Asn | Pro | Arg | Asp | Thr | Glu | |
| | | 355 | | | | | 360 | | | | | 365 | | | | |
| gat | gtt | cct | tgg | ata | aca | cta | aat | agc | agc | att | cag | aaa | gtt | aat | gag | 1271 |
| Asp | Val | Pro | Trp | Ile | Thr | Leu | Asn | Ser | Ser | Ile | Gln | Lys | Val | Asn | Glu | |
| 370 | | | | | 375 | | | | | 380 | | | | | | |

| | | | | | | | | | | | | | | | | |
|---|---|---|---|---|---|---|---|---|---|---|---|---|---|---|---|---|
| tgg | ttt | tcc | aga | agt | gat | gaa | ctg | tta | ggt | tct | gat | gac | tca | cat | gat | 1319 |
| Trp | Phe | Ser | Arg | Ser | Asp | Glu | Leu | Leu | Gly | Ser | Asp | Asp | Ser | His | Asp | |
| 385 | | | | 390 | | | | | 395 | | | | | | 400 | |
| ggg | gag | tct | gaa | tca | aat | gcc | aaa | gta | gct | gat | gta | ttg | gac | gtt | cta | 1367 |
| Gly | Glu | Ser | Glu | Ser | Asn | Ala | Lys | Val | Ala | Asp | Val | Leu | Asp | Val | Leu | |
| | | | | 405 | | | | 410 | | | | | 415 | | | |
| aat | gag | gta | gat | gaa | tat | tct | ggt | tct | tca | gag | aaa | ata | gac | tta | ctg | 1415 |
| Asn | Glu | Val | Asp | Glu | Tyr | Ser | Gly | Ser | Ser | Glu | Lys | Ile | Asp | Leu | Leu | |
| | | | 420 | | | | | 425 | | | | | 430 | | | |
| gcc | agt | gat | cct | cat | gag | gct | tta | ata | tgt | aaa | agt | gaa | aga | gtt | cac | 1463 |
| Ala | Ser | Asp | Pro | His | Glu | Ala | Leu | Ile | Cys | Lys | Ser | Asp | Arg | Val | His | |
| | | 435 | | | | 440 | | | | | 445 | | | | | |
| tcc | aaa | tca | gta | gag | agt | aat | att | gaa | gac | aaa | ata | ttt | ggg | aaa | acc | 1511 |
| Ser | Lys | Ser | Val | Glu | Ser | Asn | Ile | Glu | Asp | Lys | Ile | Phe | Gly | Lys | Thr | |
| 450 | | | | | 455 | | | | | 460 | | | | | | |
| tat | cgg | aag | aag | gca | agc | ctc | ccc | aac | tta | agc | cat | gta | act | gaa | aat | 1559 |
| Tyr | Arg | Lys | Lys | Ala | Ser | Leu | Pro | Asn | Leu | Ser | His | Val | Thr | Glu | Asn | |
| 465 | | | | 470 | | | | | 475 | | | | | 480 | | |
| cta | att | ata | gga | gca | ttt | gtt | act | gag | cca | cag | ata | ata | caa | gag | cgt | 1607 |
| Leu | Ile | Ile | Gly | Ala | Phe | Val | Ser | Glu | Pro | Gln | Ile | Ile | Gln | Glu | Arg | |
| | | | 485 | | | | | 490 | | | | | 495 | | | |
| ccc | ctc | aca | aat | aaa | tta | aag | cgt | aaa | agg | aga | cct | aca | tca | ggc | ctt | 1655 |
| Pro | Leu | Thr | Asn | Lys | Leu | Lys | Arg | Lys | Arg | Arg | Pro | Thr | Ser | Gly | Leu | |
| | | 500 | | | | | 505 | | | | | 510 | | | | |
| cat | cct | gag | gat | ttt | atc | aag | aaa | gca | gat | ttg | gca | gtt | caa | aag | act | 1703 |
| His | Pro | Glu | Asp | Phe | Ile | Lys | Lys | Ala | Asp | Leu | Ala | Val | Gln | Lys | Thr | |
| | 515 | | | | | 520 | | | | | 525 | | | | | |
| cct | gaa | atg | ata | aat | cag | gga | act | aac | caa | acg | gag | cag | aat | ggt | caa | 1751 |
| Pro | Glu | Met | Ile | Asn | Gln | Gly | Thr | Asn | Gln | Thr | Glu | Gln | Asn | Gly | Gln | |
| 530 | | | | | 535 | | | | | 540 | | | | | | |
| gtg | atg | aat | att | act | aat | agt | ggt | cat | gag | aat | aaa | aca | aaa | ggt | gat | 1799 |
| Val | Met | Asn | Ile | Thr | Asn | Ser | Gly | His | Glu | Asn | Lys | Thr | Lys | Gly | Asp | |
| 545 | | | | 550 | | | | | 555 | | | | | 560 | | |
| tct | att | cag | aat | gag | aaa | aat | cct | aac | cca | ata | gaa | tca | ctc | gaa | aaa | 1847 |
| Ser | Ile | Gln | Asn | Glu | Lys | Asn | Pro | Asn | Pro | Ile | Glu | Ser | Leu | Glu | Lys | |
| | | | | 565 | | | | | 570 | | | | | 575 | | |
| gaa | tct | gct | ttc | aaa | acg | aaa | gct | gaa | cct | ata | agc | agc | agt | ata | agc | 1895 |
| Glu | Ser | Ala | Phe | Lys | Thr | Lys | Ala | Glu | Pro | Ile | Ser | Ser | Ser | Ile | Ser | |
| | | | 580 | | | | | 585 | | | | | 590 | | | |
| aat | atg | gaa | ctc | gaa | tta | aat | atc | cac | aat | tca | aaa | gca | cct | aaa | aag | 1943 |
| Asn | Met | Glu | Leu | Glu | Leu | Asn | Ile | Met | His | Asn | Ser | Lys | Ala | Pro | Lys | Lys |
| | | 595 | | | | | 600 | | | | | 605 | | | | |
| aat | agg | ctg | agg | agg | aag | tct | tct | acc | agg | cat | att | cat | gcg | ctt | gaa | 1991 |
| Asn | Arg | Leu | Arg | Arg | Lys | Ser | Ser | Thr | Arg | His | Ile | His | Ala | Leu | Glu | |
| | 610 | | | | | 615 | | | | | 620 | | | | | |
| cta | gta | gtc | agt | aga | aat | cta | agc | cca | cct | aat | tgt | act | gaa | ttg | caa | 2039 |
| Leu | Val | Val | Ser | Arg | Asn | Leu | Ser | Pro | Pro | Asn | Cys | Thr | Glu | Leu | Gln | |
| 625 | | | | | 630 | | | | | 635 | | | | | 640 | |
| att | gat | agt | tgt | tct | agc | agt | gaa | gag | ata | aag | aaa | aaa | aag | tac | aac | 2087 |
| Ile | Asp | Ser | Cys | Ser | Ser | Ser | Glu | Glu | Ile | Lys | Lys | Lys | Lys | Tyr | Asn | |
| | | | | 645 | | | | | 650 | | | | | 655 | | |
| caa | atg | cca | gtc | agg | cac | agc | aga | aac | cta | caa | ctc | atg | gaa | ggt | aaa | 2135 |
| Gln | Met | Pro | Val | Arg | His | Ser | Arg | Asn | Leu | Gln | Leu | Met | Glu | Gly | Lys | |
| | | | 660 | | | | | 665 | | | | | 670 | | | |
| gaa | cct | gca | act | gga | gcc | aag | aag | agt | aac | aag | cca | aat | gaa | cag | aca | 2183 |
| Glu | Pro | Ala | Thr | Gly | Ala | Lys | Lys | Ser | Asn | Lys | Pro | Asn | Glu | Gln | Thr | |
| | | 675 | | | | | 680 | | | | | 685 | | | | |
| agt | aaa | aga | cat | gac | agc | gat | act | ttc | cca | gag | ctg | aag | tta | aca | aat | 2231 |
| Ser | Lys | Arg | His | Asp | Ser | Asp | Thr | Phe | Pro | Glu | Leu | Lys | Leu | Thr | Asn | |
| | 690 | | | | | 695 | | | | | 700 | | | | | |

| | | | | | | | | | | | | | | | | |
|---|---|---|---|---|---|---|---|---|---|---|---|---|---|---|---|---|
| gca | cct | ggt | tct | ttt | act | aag | tgt | tca | aat | acc | agt | gaa | ctt | aaa | gaa | 2279 |
| Ala | Pro | Gly | Ser | Phe | Thr | Lys | Cys | Ser | Asn | Thr | Ser | Glu | Leu | Lys | Glu | |
| 705 | | | | 710 | | | | 715 | | | | | | | 720 | |
| ttt | gtc | aat | cct | agc | ctt | cca | aga | gaa | gaa | aaa | gaa | gag | aaa | cta | gaa | 2327 |
| Phe | Val | Asn | Pro | Ser | Leu | Pro | Arg | Glu | Glu | Lys | Glu | Glu | Lys | Leu | Glu | |
| | | | | 725 | | | | 730 | | | | | | 735 | | |
| aca | gtt | aaa | gtg | tct | aat | aat | gct | gaa | gac | ccc | aaa | gat | ctc | atg | tta | 2375 |
| Thr | Val | Lys | Val | Ser | Asn | Asn | Ala | Glu | Asp | Pro | Lys | Asp | Leu | Met | Leu | |
| | | | 740 | | | | | 745 | | | | | 750 | | | |
| agt | gga | gaa | agg | gtt | ttg | caa | act | gaa | aga | tct | gta | gag | agt | agc | agt | 2423 |
| Ser | Gly | Glu | Arg | Val | Leu | Gln | Thr | Glu | Arg | Ser | Val | Glu | Ser | Ser | Ser | |
| | | 755 | | | | | 760 | | | | | 765 | | | | |
| att | tca | ttg | gta | cct | ggt | act | gat | tat | ggc | act | cag | gaa | agt | atc | tcg | 2471 |
| Ile | Ser | Leu | Val | Pro | Gly | Thr | Asp | Tyr | Gly | Thr | Gln | Glu | Ser | Ile | Ser | |
| | 770 | | | | | 775 | | | | | 780 | | | | | |
| tta | ctg | gaa | gtt | agc | act | cta | ggg | aag | gca | aaa | aca | gaa | cca | aat | aaa | 2519 |
| Leu | Leu | Glu | Val | Ser | Thr | Leu | Gly | Lys | Ala | Lys | Thr | Glu | Pro | Asn | Lys | |
| 785 | | | | | 790 | | | | | 795 | | | | | 800 | |
| tgt | gtg | agt | cag | tgt | gca | gca | ttt | gaa | aac | ccc | aag | gga | cta | att | cat | 2567 |
| Cys | Val | Ser | Gln | Cys | Ala | Ala | Phe | Glu | Asn | Pro | Lys | Gly | Leu | Ile | His | |
| | | | | 805 | | | | 810 | | | | | 815 | | | |
| ggt | tgt | tcc | aaa | gat | aat | aga | aat | gac | aca | gaa | ggc | ttt | aag | tat | cca | 2615 |
| Gly | Cys | Ser | Lys | Asp | Asn | Arg | Asn | Asp | Thr | Glu | Gly | Phe | Lys | Tyr | Pro | |
| | | | 820 | | | | | 825 | | | | | 830 | | | |
| ttg | gga | cat | gaa | gtt | aac | cac | agt | cgg | gaa | aca | agc | ata | gaa | atg | gaa | 2663 |
| Leu | Gly | His | Glu | Val | Asn | His | Ser | Arg | Glu | Thr | Ser | Ile | Glu | Met | Glu | |
| | | 835 | | | | | 840 | | | | | 845 | | | | |
| gaa | agt | gaa | ctt | gat | gct | cag | tat | ttg | cag | aat | aca | ttc | aag | gtt | tca | 2711 |
| Glu | Ser | Glu | Leu | Asp | Ala | Gln | Tyr | Leu | Gln | Asn | Thr | Phe | Lys | Val | Ser | |
| | 850 | | | | | 855 | | | | | 860 | | | | | |
| aag | cgc | cag | tca | ttt | gct | ccg | ttt | tca | aat | cca | gga | aat | gca | gaa | gag | 2759 |
| Lys | Arg | Gln | Ser | Phe | Ala | Pro | Phe | Ser | Asn | Pro | Gly | Asn | Ala | Glu | Glu | |
| 865 | | | | | 870 | | | | | 875 | | | | | 880 | |
| gaa | tgt | gca | aca | ttc | tct | gcc | cac | tct | ggg | tcc | tta | aag | aaa | caa | agt | 2807 |
| Glu | Cys | Ala | Thr | Phe | Ser | Ala | His | Ser | Gly | Ser | Leu | Lys | Lys | Gln | Ser | |
| | | | | 885 | | | | 890 | | | | | 895 | | | |
| cca | aaa | gtc | act | ttt | gaa | tgt | gaa | caa | aag | gaa | gaa | aat | caa | gga | aag | 2855 |
| Pro | Lys | Val | Thr | Phe | Glu | Cys | Glu | Gln | Lys | Glu | Glu | Asn | Gln | Gly | Lys | |
| | | | 900 | | | | | 905 | | | | | 910 | | | |
| aat | gag | tct | aat | atc | aag | cct | gta | cag | aca | gtt | aat | atc | act | gca | ggc | 2903 |
| Asn | Glu | Ser | Asn | Ile | Lys | Pro | Val | Gln | Thr | Val | Asn | Ile | Thr | Ala | Gly | |
| | | 915 | | | | | 920 | | | | | 925 | | | | |
| ttt | cct | gtg | gtt | ggt | cag | aaa | gat | aag | cca | gtt | gat | aat | gcc | aaa | tgt | 2951 |
| Phe | Pro | Val | Val | Gly | Gln | Lys | Asp | Lys | Pro | Val | Asp | Asn | Ala | Lys | Cys | |
| | 930 | | | | | 935 | | | | | 940 | | | | | |
| agt | atc | aaa | gga | ggc | tct | agg | ttt | tgt | cta | tca | tct | cag | ttc | aga | ggc | 2999 |
| Ser | Ile | Lys | Gly | Gly | Ser | Arg | Phe | Cys | Leu | Ser | Ser | Gln | Phe | Arg | Gly | |
| 945 | | | | | 950 | | | | | 955 | | | | | 960 | |
| aac | gaa | act | gga | ctc | att | act | cca | aat | aaa | cat | gga | ctt | tta | caa | aac | 3047 |
| Asn | Glu | Thr | Gly | Leu | Ile | Thr | Pro | Asn | Lys | His | Gly | Leu | Leu | Gln | Asn | |
| | | | | 965 | | | | 970 | | | | | 975 | | | |
| cca | tat | cgt | ata | cca | cca | ctt | ttt | ccc | atc | aag | tca | ttt | gtt | aaa | act | 3095 |
| Pro | Tyr | Arg | Ile | Pro | Pro | Leu | Phe | Pro | Ile | Lys | Ser | Phe | Val | Lys | Thr | |
| | | | 980 | | | | | 985 | | | | | 990 | | | |
| aaa | tgt | aag | aaa | aat | ctg | cta | gag | gaa | aac | ttt | gag | gaa | cat | tca | atg | 3143 |
| Lys | Cys | Lys | Lys | Asn | Leu | Leu | Glu | Glu | Asn | Phe | Glu | Glu | His | Ser | Met | |
| | | | 995 | | | | | 1000 | | | | | 1005 | | | |
| tca | cct | gaa | aga | gaa | atg | gga | aat | gag | aac | att | cca | agt | aca | gtg | agc | 3191 |
| Ser | Pro | Glu | Arg | Glu | Met | Gly | Asn | Glu | Asn | Ile | Pro | Ser | Thr | Val | Ser | |
| | 1010 | | | | | 1015 | | | | | 1020 | | | | | |

| | |
|---|---|
| aca att agc cgt aat aac att aga gaa aat gtt ttt aaa gaa gcc agc<br>Thr Ile Ser Arg Asn Asn Ile Arg Glu Asn Val Phe Lys Glu Ala Ser<br>1025                             1030                        1035                        1040 | 3239 |
| tca agc aat att aat gaa gta ggt tcc agt act aat gaa gtg ggc tcc<br>Ser Ser Asn Ile Asn Glu Val Gly Ser Ser Thr Asn Glu Val Gly Ser<br>                  1045                        1050                        1055 | 3287 |
| agt att aat gaa ata ggt tcc agt gat gaa aac att caa gca gaa cta<br>Ser Ile Asn Glu Ile Gly Ser Ser Asp Glu Asn Ile Gln Ala Glu Leu<br>                  1060                        1065                        1070 | 3335 |
| ggt aga aac aga ggg cca aaa ttg aat gct atg ctt aga tta ggg gtt<br>Gly Arg Asn Arg Gly Pro Lys Leu Asn Ala Met Leu Arg Leu Gly Val<br>1075                             1080                        1085 | 3383 |
| ttg caa cct gag gtc tat aaa caa agt ctt cct gga agt aat tgt aag<br>Leu Gln Pro Glu Val Tyr Lys Gln Ser Leu Pro Gly Ser Asn Cys Lys<br>1090                             1095                        1100 | 3431 |
| cat cct gaa ata aaa aag caa gaa tat gaa gaa gta gtt cag act gtt<br>His Pro Glu Ile Lys Lys Gln Glu Tyr Glu Glu Val Val Gln Thr Val<br>1105                             1110                        1115                        1120 | 3479 |
| aat aca gat ttc tct cca tat ctg att tca gat aac tta gaa cag cct<br>Asn Thr Asp Phe Ser Pro Tyr Leu Ile Ser Asp Asn Leu Glu Gln Pro<br>                  1125                        1130                        1135 | 3527 |
| atg gga agt agt cat gca tct cag gtt tgt tct gag aca cct gat gac<br>Met Gly Ser Ser His Ala Ser Gln Val Cys Ser Glu Thr Pro Asp Asp<br>                  1140                        1145                        1150 | 3575 |
| ctg tta gat gat ggt gaa ata aag gaa gat act agt ttt gct gaa aat<br>Leu Leu Asp Asp Gly Glu Ile Lys Glu Asp Thr Ser Phe Ala Glu Asn<br>                  1155                        1160                        1165 | 3623 |
| gac att aag gaa agt tct gct gtt ttt agc aaa agc gtc cag aaa gga<br>Asp Ile Lys Glu Ser Ser Ala Val Phe Ser Lys Ser Val Gln Lys Gly<br>1170                             1175                        1180 | 3671 |
| gag ctt agc agg agt cct agc cct ttc acc cat aca cat ttg gct cag<br>Glu Leu Ser Arg Ser Pro Ser Pro Phe Thr His Thr His Leu Ala Gln<br>1185                             1190                        1195                        1200 | 3719 |
| ggt tac cga aga ggg gcc aag aaa tta gag tcc tca gaa gag aac tta<br>Gly Tyr Arg Arg Gly Ala Lys Lys Leu Glu Ser Ser Glu Glu Asn Leu<br>                  1205                        1210                        1215 | 3767 |
| tct agt gag gat gaa gag ctt ccc tgc ttc caa cac ttg tta ttt ggt<br>Ser Ser Glu Asp Glu Glu Leu Pro Cys Phe Gln His Leu Leu Phe Gly<br>                  1220                        1225                        1230 | 3815 |
| aaa gta aac aat ata cct tct cag tct act agg cat agc acc gtt gct<br>Lys Val Asn Asn Ile Pro Ser Gln Ser Thr Arg His Ser Thr Val Ala<br>1235                             1240                        1245 | 3863 |
| acc gag tgt ctg tct aag aac aca gag gag aat tta tta tca ttg aag<br>Thr Glu Cys Leu Ser Lys Asn Thr Glu Glu Asn Leu Leu Ser Leu Lys<br>1250                             1255                        1260 | 3911 |
| aat agc tta aat gac tgc agt aac cag gta ata ttg gca aag gca tct<br>Asn Ser Leu Asn Asp Cys Ser Asn Gln Val Ile Leu Ala Lys Ala Ser<br>1265                             1270                        1275                        1280 | 3959 |
| cag gaa cat cac ctt agt gag gaa aca aaa tgt tct gct agc ttg ttt<br>Gln Glu His His Leu Ser Glu Glu Thr Lys Cys Ser Ala Ser Leu Phe<br>                  1285                        1290                        1295 | 4007 |
| tct tca cag tgc agt gaa ttg gaa gac ttg act gca aat aca aac acc<br>Ser Ser Gln Cys Ser Glu Leu Glu Asp Leu Thr Ala Asn Thr Asn Thr<br>                  1300                        1305                        1310 | 4055 |
| cag gat cct ttc ttg att ggt tct tcc aaa caa atg agg cat cag tct<br>Gln Asp Pro Phe Leu Ile Gly Ser Ser Lys Gln Met Arg His Gln Ser<br>                  1315                        1320                        1325 | 4103 |
| gaa agc cag gga gtt ggt ctg agt gac aag gaa ttg gtt tca gat gat<br>Glu Ser Gln Gly Val Gly Leu Ser Asp Lys Glu Leu Val Ser Asp Asp<br>                  1330                        1335                        1340 | 4151 |

```
gaa  gaa  aga  gga  acg  ggc  ttg  gaa  gaa  aat  aat  caa  gaa  gag  caa  agc    4199
Glu  Glu  Arg  Gly  Thr  Gly  Leu  Glu  Glu  Asn  Asn  Gln  Glu  Glu  Gln  Ser
1345               1350                    1355                    1360 atg  gat  tca  aac  tta  ggt  gaa  gca  gca  tct  ggg  tgt  gag  agt  gaa  aca    4247
Met  Asp  Ser  Asn  Leu  Gly  Glu  Ala  Ala  Ser  Gly  Cys  Glu  Ser  Glu  Thr
          1365                    1370                    1375 agc  gtc  tct  gaa  gac  tgc  tca  ggg  cta  tcc  tct  cag  agt  gac  att  tta    4295
Ser  Val  Ser  Glu  Asp  Cys  Ser  Gly  Leu  Ser  Ser  Gln  Ser  Asp  Ile  Leu
               1380                    1385                    1390 acc  act  cag  cag  agg  gat  acc  atg  caa  cat  aac  ctg  ata  aag  ctc  cag    4343
Thr  Thr  Gln  Gln  Arg  Asp  Thr  Met  Gln  His  Asn  Leu  Ile  Lys  Leu  Gln
                    1395                    1400                    1405 cag  gaa  atg  gct  gaa  cta  gaa  gct  gtg  tta  gaa  cag  cat  ggg  agc  cag    4391
Gln  Glu  Met  Ala  Glu  Leu  Glu  Ala  Val  Leu  Glu  Gln  His  Gly  Ser  Gln
          1410                    1415                    1420 cct  tct  aac  agc  tac  cct  tcc  atc  ata  agt  gac  tct  tct  gcc  ctt  gag    4439
Pro  Ser  Asn  Ser  Tyr  Pro  Ser  Ile  Ile  Ser  Asp  Ser  Ser  Ala  Leu  Glu
1425               1430                    1435                         1440 gac  ctg  cga  aat  cca  gaa  caa  agc  aca  tca  gaa  aaa  gca  gta  tta  act    4487
Asp  Leu  Arg  Asn  Pro  Glu  Gln  Ser  Thr  Ser  Glu  Lys  Val  Leu  Gln  Thr
               1445                    1450                    1455 tca  cag  aaa  agt  agt  gaa  tac  cct  ata  agc  cag  aat  cca  gaa  ggc  ctt    4535
Ser  Gln  Lys  Ser  Ser  Glu  Tyr  Pro  Ile  Ser  Gln  Asn  Pro  Glu  Gly  Xaa
          1460                    1465                    1470 tct  gct  gac  aag  ttt  gag  gtg  tct  gca  gat  agt  tct  acc  agt  aaa  aat    4583
Ser  Ala  Asp  Lys  Phe  Glu  Val  Ser  Ala  Asp  Ser  Ser  Thr  Ser  Lys  Asn
               1475                    1480                    1485 aaa  gaa  cca  gga  gtg  gaa  agg  tca  tcc  cct  tct  aaa  tgc  cca  tca  tta    4631
Lys  Glu  Pro  Gly  Val  Glu  Arg  Ser  Ser  Pro  Ser  Lys  Cys  Pro  Ser  Leu
               1490                    1495                    1500 gat  gat  agg  tgg  tac  atg  cac  agt  tgc  tct  ggg  agt  ctt  cag  aat  aga    4679
Asp  Asp  Arg  Trp  Tyr  Met  His  Ser  Cys  Ser  Gly  Ser  Leu  Gln  Asn  Arg
1505               1510                    1515                         1520 aac  tac  cca  tct  caa  gag  gag  ctc  att  aag  gtt  gtt  gat  gtg  gag  gag    4727
Asn  Tyr  Pro  Pro  Gln  Glu  Glu  Leu  Ile  Lys  Val  Val  Asp  Val  Glu  Glu
                    1525                    1530                    1535 caa  cag  ctg  gaa  gag  tct  ggg  cca  cac  gat  ttg  acg  gaa  aca  tct  tac    4775
Gln  Gln  Leu  Glu  Glu  Ser  Gly  Pro  His  Asp  Leu  Thr  Glu  Thr  Ser  Tyr
          1540                    1545                    1550 ttg  cca  agg  caa  gat  cta  gag  gga  acc  cct  tac  ctg  gaa  tct  gga  atc    4823
Leu  Pro  Arg  Gln  Asp  Leu  Glu  Gly  Thr  Pro  Tyr  Leu  Glu  Ser  Gly  Ile
          1555                    1560                    1565 agc  ctc  ttc  tct  gat  gac  cct  gaa  tct  gat  cct  tct  gaa  gac  aga  gcc    4871
Ser  Leu  Phe  Ser  Asp  Asp  Pro  Glu  Ser  Asp  Pro  Ser  Glu  Asp  Arg  Ala
          1570                    1575                    1580 cca  gag  tca  gct  cgt  gtt  ggc  aac  ata  cca  tct  tca  acc  tct  gca  ttg    4919
Pro  Glu  Ser  Ala  Arg  Val  Gly  Asn  Ile  Pro  Ser  Ser  Thr  Ser  Ala  Leu
1585               1590                    1595                         1600 aaa  gtt  ccc  caa  ttg  aaa  gtt  gca  gaa  tct  gcc  cag  agt  cca  gct  gct    4967
Lys  Val  Pro  Gln  Leu  Lys  Val  Ala  Glu  Ser  Ala  Gln  Ser  Pro  Ala  Ala
               1605                    1610                    1615 gct  cat  act  act  gat  act  gct  ggg  tat  aat  gca  atg  gaa  gaa  agt  gtg    5015
Ala  His  Thr  Thr  Asp  Thr  Ala  Gly  Tyr  Asn  Ala  Met  Glu  Glu  Ser  Val
                    1620                    1625                    1630 agc  agg  gag  aag  cca  gaa  ttg  aca  gct  tca  aca  gaa  agg  gtc  aac  aaa    5063
Ser  Arg  Glu  Lys  Pro  Glu  Leu  Thr  Ala  Ser  Thr  Glu  Arg  Val  Asn  Lys
          1635                    1640                    1645 aga  atg  tcc  atg  gtg  gtg  tct  ggc  ctg  acc  cca  gaa  gaa  ttt  atg  ctc    5111
Arg  Met  Ser  Met  Val  Val  Ser  Gly  Leu  Thr  Pro  Glu  Glu  Phe  Met  Leu
          1650                    1655                    1660
```

```
gtg  tac  aag  ttt  gcc  aga  aaa  cac  cac  atc  act  tta  act  aat  cta  att                5159
Val  Tyr  Lys  Phe  Ala  Arg  Lys  His  His  Ile  Thr  Leu  Thr  Asn  Leu  Ile
1665                1670                     1675                     1680 act  gaa  gag  act  act  cat  gtt  gtt  atg  aaa  aca  gat  gct  gag  ttt  gtg                5207
Thr  Glu  Glu  Thr  Thr  His  Val  Val  Met  Lys  Thr  Asp  Ala  Glu  Phe  Val
                    1685                     1690                     1695 tgt  gaa  cgg  aca  ctg  aaa  tat  ttt  cta  gga  att  gcg  gga  gga  aaa  tgg                5255
Cys  Glu  Arg  Thr  Leu  Lys  Tyr  Phe  Leu  Gly  Ile  Ala  Gly  Gly  Lys  Trp
               1700                     1705                     1710 gta  gtt  agc  tat  ttc  tgg  gtg  acc  cag  tct  att  aaa  gaa  aga  aaa  atg                5303
Val  Val  Ser  Tyr  Phe  Trp  Val  Thr  Gln  Ser  Ile  Lys  Glu  Arg  Lys  Met
          1715                     1720                     1725 ctg  aat  gag  cat  gat  ttt  gaa  gtc  aga  gga  gat  gtg  gtc  aat  gga  aga                5351
Leu  Asn  Glu  His  Asp  Phe  Glu  Val  Arg  Gly  Asp  Val  Val  Asn  Gly  Arg
     1730                     1735                     1740 aac  cac  caa  ggt  cca  aag  cga  gca  aga  gaa  tcc  cag  gac  aga  aag  atc                5399
Asn  His  Gln  Gly  Pro  Lys  Arg  Ala  Arg  Glu  Ser  Gln  Asp  Arg  Lys  Ile
1745                1750                     1755                     1760 ttc  agg  ggg  cta  gaa  atc  tgt  tgc  tat  ggg  ccc  ttc  acc  aac  atg  ccc                5447
Phe  Arg  Gly  Leu  Glu  Ile  Cys  Cys  Tyr  Gly  Pro  Phe  Thr  Asn  Met  Pro
                    1765                     1770                     1775 aca  gat  caa  ctg  gaa  tgg  atg  gta  cag  ctg  tgt  ggt  gct  tct  gtg  gtg                5495
Thr  Asp  Gln  Leu  Glu  Trp  Met  Val  Gln  Leu  Cys  Gly  Ala  Ser  Val  Val
               1780                     1785                     1790 aag  gag  ctt  tca  tca  ttc  acc  ctt  ggc  aca  ggt  gtc  cac  cca  att  gtg                5543
Lys  Glu  Leu  Ser  Ser  Phe  Thr  Leu  Gly  Thr  Gly  Val  His  Pro  Ile  Val
          1795                     1800                     1805 gtt  gtg  cag  cca  gat  gcc  tgg  aca  gag  gac  aat  ggc  ttc  cat  gca  att                5591
Val  Val  Gln  Pro  Asp  Ala  Trp  Thr  Glu  Asp  Asn  Gly  Phe  His  Ala  Ile
     1810                     1815                     1820 ggg  cag  atg  tgt  gag  gca  cct  gtg  gtg  acc  cga  gag  tgg  gtg  ttg  gac                5639
Gly  Gln  Met  Cys  Glu  Ala  Pro  Val  Val  Thr  Arg  Glu  Trp  Val  Leu  Asp
1825                1830                     1835                     1840 agt  gta  gca  ctc  tac  cag  tgc  cag  gag  ctg  gac  acc  tac  ctg  ata  ccc                5687
Ser  Val  Ala  Leu  Tyr  Gln  Cys  Gln  Glu  Leu  Asp  Thr  Tyr  Leu  Ile  Pro
                    1845                     1850                     1855 cag  atc  ccc  cac  agc  cac  tac  tgat                                                        5712
Gln  Ile  Pro  His  Ser  His  Tyr
               1860
```

( 2 ) INFORMATION FOR SEQ ID NO:2:

( i ) SEQUENCE CHARACTERISTICS:
        ( A ) LENGTH: 1863
        ( B ) TYPE: amino acid
            ( C ) STRANDEDNESS: single
        ( D ) TOPOLOGY: unknown ( i i ) MOLECULE TYPE: protein ( i i i ) HYPOTHETICAL: no ( i v ) ANTI-SENSE: no ( v ) ORIGINAL SOURCE:
        ( A ) ORGANISM: Homo sapiens
        ( C ) INDIVIDUAL ISOLATE:
        ( D ) DEVELOPMENTAL STAGE: adult
        ( F ) TISSUE TYPE: female breast
        ( G ) CELL TYPE: ductal carcinoma in situ, invasive
            breast cancer and normal breast tissue
        ( H ) CELL LINE: not derived from a cell line
        ( I ) ORGANELLE: no ( v i i ) IMMEDIATE SOURCE:
        ( A ) LIBRARY: cDNA library derived from human
        ( B ) CLONE: obtained using published sequence (viii) POSITION IN GENOME:
    (A) CHROMOSOME/SEGMENT: unknown
    (B) MAP POSITION: unknown
    (C) UNITS: unknown (ix) FEATURE:
    (A) NAME/KEY: BRCA1 protein
    (B) LOCATION: 1 to 1863
    (C) IDENTIFICATION METHOD: observation of mRNA and antisense inhibition of BRCA1 gene
    (D) OTHER INFORMATION: BRCA1 protein has a negative regulatory effect on growth of human mammary cells.

(x) PUBLICATION INFORMATION:
    (A) AUTHORS: Miki, Y., et. al.
    (B) TITLE: A strong candidate gene for the breast and ovarian cancer susceptibility gene BRCA1.
    (C) JOURNAL: Science
    (D) VOLUME: 266
    (E) PAGES: 66-71
    (F) DATE: 1994
    (K) RELEVANT RESIDUES IN SEQ ID NO:2: granin box domain at amino acids 1214-1223

(xi) SEQUENCE DESCRIPTION: SEQ ID NO:2:

| | | | | | | | | | | | | | | |
|---|---|---|---|---|---|---|---|---|---|---|---|---|---|---|
| Met | Asp | Leu | Ser | Ala | Leu | Arg | Val | Glu | Glu | Val | Gln | Asn | Val | Ile | Asn |
| 1 | | | | 5 | | | | | 10 | | | | | 15 | |
| Ala | Met | Gln | Lys | Ile | Leu | Glu | Cys | Pro | Ile | Cys | Leu | Glu | Leu | Ile | Lys |
| | | | 20 | | | | | 25 | | | | | 30 | | |
| Glu | Pro | Val | Ser | Thr | Lys | Cys | Asp | His | Ile | Phe | Cys | Lys | Phe | Cys | Met |
| | | | 35 | | | | 40 | | | | | 45 | | | |
| Leu | Lys | Leu | Leu | Asn | Gln | Lys | Lys | Gly | Pro | Ser | Gln | Cys | Pro | Leu | Cys |
| | 50 | | | | | 55 | | | | | 60 | | | | |
| Lys | Asn | Asp | Ile | Thr | Lys | Arg | Ser | Leu | Gln | Glu | Ser | Thr | Arg | Phe | Ser |
| 65 | | | | | 70 | | | | | 75 | | | | | 80 |
| Gln | Leu | Val | Glu | Glu | Leu | Leu | Lys | Ile | Ile | Cys | Ala | Phe | Gln | Leu | Asp |
| | | | | 85 | | | | | 90 | | | | | 95 | |
| Thr | Gly | Leu | Glu | Tyr | Ala | Asn | Ser | Tyr | Asn | Phe | Ala | Lys | Lys | Glu | Asn |
| | | | | 100 | | | | | 105 | | | | | 110 | |
| Asn | Ser | Pro | Glu | His | Leu | Lys | Asp | Glu | Val | Ser | Ile | Ile | Gln | Ser | Met |
| | | | 115 | | | | 120 | | | | | 125 | | | |
| Gly | Tyr | Arg | Asn | Arg | Ala | Lys | Arg | Leu | Leu | Gln | Ser | Glu | Pro | Glu | Asn |
| | | | 130 | | | | 135 | | | | | 140 | | | |
| Pro | Ser | Leu | Gln | Glu | Thr | Ser | Leu | Ser | Val | Gln | Leu | Ser | Asn | Leu | Gly |
| 145 | | | | | 150 | | | | | 155 | | | | | 160 |
| Thr | Val | Arg | Thr | Leu | Arg | Thr | Lys | Gln | Arg | Ile | Gln | Pro | Gln | Lys | Thr |
| | | | | 165 | | | | | 170 | | | | | 175 | |
| Ser | Val | Tyr | Ile | Glu | Leu | Gly | Ser | Asp | Ser | Ser | Glu | Asp | Thr | Val | Asn |
| | | | 180 | | | | | 185 | | | | | 190 | | |
| Lys | Ala | Thr | Tyr | Cys | Ser | Val | Gly | Asp | Gln | Glu | Leu | Leu | Gln | Ile | Thr |
| | | 195 | | | | | 200 | | | | | 205 | | | |
| Pro | Gln | Gly | Thr | Arg | Asp | Glu | Ile | Ser | Leu | Asp | Ser | Ala | Lys | Lys | Ala |
| | 210 | | | | | 215 | | | | | 220 | | | | |
| Ala | Cys | Glu | Phe | Ser | Glu | Thr | Asp | Val | Thr | Asn | Thr | Glu | His | His | Gln |
| 225 | | | | | 230 | | | | | 235 | | | | | 240 |
| Pro | Ser | Asn | Asn | Asp | Leu | Asn | Thr | Thr | Glu | Lys | Arg | Ala | Ala | Glu | Arg |
| | | | | 245 | | | | | 250 | | | | | 255 | |
| His | Pro | Glu | Lys | Tyr | Gln | Gly | Ser | Ser | Val | Ser | Asn | Leu | His | Val | Glu |
| | | | 260 | | | | | 265 | | | | | 270 | | |
| Pro | Cys | Gly | Thr | Asn | Thr | His | Ala | Ser | Ser | Leu | Gln | His | Glu | Asn | Ser |
| | | | 275 | | | | 280 | | | | | 285 | | | |

| Ser | Leu | Leu | Leu | Thr | Lys | Asp | Arg | Met | Asn | Val | Glu | Lys | Ala | Glu | Phe |
|---|---|---|---|---|---|---|---|---|---|---|---|---|---|---|---|
| | 290 | | | | 295 | | | | | 300 | | | | | |

| Cys | Asn | Lys | Ser | Lys | Gln | Pro | Gly | Leu | Ala | Arg | Ser | Gln | His | Asn | Arg |
|---|---|---|---|---|---|---|---|---|---|---|---|---|---|---|---|
| 305 | | | | | 310 | | | | | 315 | | | | | 320 |

| Trp | Ala | Gly | Ser | Lys | Glu | Thr | Cys | Asn | Asp | Arg | Arg | Thr | Pro | Ser | Thr |
|---|---|---|---|---|---|---|---|---|---|---|---|---|---|---|---|
| | | | | 325 | | | | | 330 | | | | | 335 | |

| Glu | Lys | Lys | Val | Asp | Leu | Asn | Ala | Asp | Pro | Leu | Cys | Glu | Arg | Lys | Glu |
|---|---|---|---|---|---|---|---|---|---|---|---|---|---|---|---|
| | | | 340 | | | | | 345 | | | | | 350 | | |

| Trp | Asn | Lys | Gln | Lys | Leu | Pro | Cys | Ser | Glu | Asn | Pro | Arg | Asp | Thr | Glu |
|---|---|---|---|---|---|---|---|---|---|---|---|---|---|---|---|
| | | | 355 | | | | | 360 | | | | | 365 | | |

| Asp | Val | Pro | Trp | Ile | Thr | Leu | Asn | Ser | Ser | Ile | Gln | Lys | Val | Asn | Glu |
|---|---|---|---|---|---|---|---|---|---|---|---|---|---|---|---|
| | | 370 | | | | 375 | | | | | 380 | | | | |

| Trp | Phe | Ser | Arg | Ser | Asp | Glu | Leu | Leu | Gly | Ser | Asp | Asp | Ser | His | Asp |
|---|---|---|---|---|---|---|---|---|---|---|---|---|---|---|---|
| 385 | | | | | 390 | | | | | 395 | | | | | 400 |

| Gly | Glu | Ser | Glu | Ser | Asn | Ala | Lys | Val | Ala | Asp | Val | Leu | Asp | Val | Leu |
|---|---|---|---|---|---|---|---|---|---|---|---|---|---|---|---|
| | | | | 405 | | | | | 410 | | | | | 415 | |

| Asn | Glu | Val | Asp | Glu | Tyr | Ser | Gly | Ser | Ser | Glu | Lys | Ile | Asp | Leu | Leu |
|---|---|---|---|---|---|---|---|---|---|---|---|---|---|---|---|
| | | | 420 | | | | | 425 | | | | | 430 | | |

| Ala | Ser | Asp | Pro | His | Glu | Ala | Leu | Ile | Cys | Lys | Ser | Asp | Arg | Val | His |
|---|---|---|---|---|---|---|---|---|---|---|---|---|---|---|---|
| | | 435 | | | | 440 | | | | | 445 | | | | |

| Ser | Lys | Ser | Val | Glu | Ser | Asp | Ile | Glu | Asp | Lys | Ile | Phe | Gly | Lys | Thr |
|---|---|---|---|---|---|---|---|---|---|---|---|---|---|---|---|
| | 450 | | | | | 455 | | | | | 460 | | | | |

| Tyr | Arg | Lys | Lys | Ala | Ser | Leu | Pro | Asn | Leu | Ser | His | Val | Thr | Glu | Asn |
|---|---|---|---|---|---|---|---|---|---|---|---|---|---|---|---|
| 465 | | | | | 470 | | | | | 475 | | | | | 480 |

| Leu | Ile | Ile | Gly | Ala | Phe | Val | Ser | Glu | Pro | Gln | Ile | Ile | Gln | Glu | Arg |
|---|---|---|---|---|---|---|---|---|---|---|---|---|---|---|---|
| | | | | 485 | | | | | 490 | | | | | 495 | |

| Pro | Leu | Thr | Asn | Lys | Leu | Lys | Arg | Lys | Arg | Arg | Pro | Thr | Ser | Gly | Leu |
|---|---|---|---|---|---|---|---|---|---|---|---|---|---|---|---|
| | | | 500 | | | | | 505 | | | | | 510 | | |

| His | Pro | Glu | Asp | Phe | Ile | Lys | Lys | Ala | Asp | Leu | Ala | Val | Gln | Lys | Thr |
|---|---|---|---|---|---|---|---|---|---|---|---|---|---|---|---|
| | | | 515 | | | | | 520 | | | | | 525 | | |

| Pro | Glu | Met | Ile | Asn | Gln | Gly | Thr | Asn | Gln | Thr | Glu | Gln | Asn | Gly | Gln |
|---|---|---|---|---|---|---|---|---|---|---|---|---|---|---|---|
| | 530 | | | | | 535 | | | | | 540 | | | | |

| Val | Met | Asn | Ile | Thr | Asn | Ser | Gly | His | Glu | Asn | Lys | Thr | Lys | Gly | Asp |
|---|---|---|---|---|---|---|---|---|---|---|---|---|---|---|---|
| 545 | | | | | 550 | | | | | 555 | | | | | 560 |

| Ser | Ile | Gln | Asn | Glu | Lys | Asn | Pro | Asn | Pro | Ile | Glu | Ser | Leu | Glu | Lys |
|---|---|---|---|---|---|---|---|---|---|---|---|---|---|---|---|
| | | | | 565 | | | | | 570 | | | | | 575 | |

| Glu | Ser | Ala | Phe | Lys | Thr | Lys | Ala | Glu | Pro | Ile | Ser | Ser | Ser | Ile | Ser |
|---|---|---|---|---|---|---|---|---|---|---|---|---|---|---|---|
| | | | 580 | | | | | 585 | | | | | 590 | | |

| Asn | Glu | Leu | Glu | Leu | Asn | Ile | Met | His | Asn | Ser | Lys | Ala | Pro | Lys | Lys |
|---|---|---|---|---|---|---|---|---|---|---|---|---|---|---|---|
| | | | 595 | | | | | 600 | | | | | 605 | | |

| Asn | Arg | Leu | Arg | Arg | Lys | Ser | Ser | Thr | Arg | His | Ile | His | Ala | Leu | Glu |
|---|---|---|---|---|---|---|---|---|---|---|---|---|---|---|---|
| | 610 | | | | | 615 | | | | | 620 | | | | |

| Leu | Val | Val | Ser | Arg | Asn | Leu | Ser | Pro | Pro | Asn | Cys | Thr | Glu | Leu | Gln |
|---|---|---|---|---|---|---|---|---|---|---|---|---|---|---|---|
| 625 | | | | | 630 | | | | | 635 | | | | | 640 |

| Ile | Asp | Ser | Cys | Ser | Ser | Ser | Glu | Glu | Ile | Lys | Lys | Lys | Lys | Tyr | Asn |
|---|---|---|---|---|---|---|---|---|---|---|---|---|---|---|---|
| | | | | 645 | | | | | 650 | | | | | 655 | |

| Gln | Met | Pro | Val | Arg | His | Ser | Arg | Asn | Leu | Gln | Leu | Met | Glu | Gly | Lys |
|---|---|---|---|---|---|---|---|---|---|---|---|---|---|---|---|
| | | | 660 | | | | | 665 | | | | | 670 | | |

| Glu | Pro | Ala | Thr | Gly | Ala | Lys | Lys | Ser | Asn | Lys | Pro | Asn | Glu | Gln | Thr |
|---|---|---|---|---|---|---|---|---|---|---|---|---|---|---|---|
| | | | 675 | | | | | 680 | | | | | 685 | | |

| Ser | Lys | Arg | His | Asp | Ser | Asp | Thr | Phe | Pro | Glu | Leu | Lys | Leu | Thr | Asn |
|---|---|---|---|---|---|---|---|---|---|---|---|---|---|---|---|
| | 690 | | | | | 695 | | | | | 700 | | | | |

-continued

| | | | | | | | | | | | | | | |
|---|---|---|---|---|---|---|---|---|---|---|---|---|---|---|
| Ala | Pro | Gly | Ser | Phe | Thr | Lys | Cys | Ser | Asn | Thr | Ser | Glu | Leu | Lys | Glu |
| 705 | | | | 710 | | | | 715 | | | | | | 720 |
| Phe | Val | Asn | Pro | Ser | Leu | Pro | Arg | Glu | Glu | Lys | Glu | Lys | Leu | Glu |
| | | | 725 | | | | 730 | | | | | 735 | | |
| Thr | Val | Lys | Val | Ser | Asn | Asn | Ala | Glu | Asp | Pro | Lys | Asp | Leu | Met | Leu |
| | | | 740 | | | | 745 | | | | 750 | | | | |
| Ser | Gly | Glu | Arg | Val | Leu | Gln | Thr | Glu | Arg | Ser | Val | Glu | Ser | Ser | Ser |
| | | 755 | | | | | 760 | | | | 765 | | | | |
| Ile | Ser | Leu | Val | Pro | Gly | Thr | Asp | Tyr | Gly | Thr | Gln | Glu | Ser | Ile | Ser |
| | 770 | | | | | 775 | | | | 780 | | | | | |
| Leu | Leu | Glu | Val | Ser | Thr | Leu | Gly | Lys | Ala | Lys | Thr | Glu | Pro | Asn | Lys |
| 785 | | | | 790 | | | | 795 | | | | | | 800 |
| Cys | Val | Ser | Gln | Cys | Ala | Ala | Phe | Glu | Asn | Pro | Lys | Gly | Leu | Ile | His |
| | | | 805 | | | | 810 | | | | | 815 | | |
| Gly | Cys | Ser | Lys | Asp | Asn | Arg | Asn | Asp | Thr | Glu | Gly | Phe | Lys | Tyr | Pro |
| | | 820 | | | | 825 | | | | 830 | | | | |
| Leu | Gly | His | Glu | Val | Asn | His | Ser | Arg | Glu | Thr | Ser | Ile | Glu | Met | Glu |
| | | 835 | | | | 840 | | | | 845 | | | | |
| Glu | Ser | Glu | Leu | Asp | Ala | Gln | Tyr | Leu | Gln | Asn | Thr | Phe | Lys | Val | Ser |
| 850 | | | | 855 | | | | 860 | | | | | | |
| Lys | Arg | Gln | Ser | Phe | Ala | Pro | Phe | Ser | Asn | Pro | Gly | Asn | Ala | Glu | Glu |
| 865 | | | | 870 | | | | 875 | | | | | | 880 |
| Glu | Cys | Ala | Thr | Phe | Ser | Ala | His | Ser | Gly | Ser | Leu | Lys | Lys | Gln | Ser |
| | | | 885 | | | | 890 | | | | 895 | | | |
| Pro | Lys | Val | Thr | Phe | Glu | Cys | Glu | Gln | Lys | Glu | Glu | Asn | Gln | Gly | Lys |
| | | 900 | | | | 905 | | | | 910 | | | | |
| Asn | Glu | Ser | Asn | Ile | Lys | Pro | Val | Gln | Thr | Val | Asn | Ile | Thr | Ala | Gly |
| | 915 | | | | | 920 | | | | 925 | | | | |
| Phe | Pro | Val | Val | Gly | Gln | Lys | Asp | Lys | Pro | Val | Asp | Asn | Ala | Lys | Cys |
| | 930 | | | | 935 | | | | 940 | | | | | |
| Ser | Ile | Lys | Gly | Gly | Ser | Arg | Phe | Cys | Leu | Ser | Ser | Gln | Phe | Arg | Gly |
| 945 | | | | 950 | | | | 955 | | | | | | 960 |
| Asn | Glu | Thr | Gly | Leu | Ile | Thr | Pro | Asn | Lys | His | Gly | Leu | Leu | Gln | Asn |
| | | | 965 | | | | 970 | | | | 975 | | | |
| Pro | Tyr | Arg | Ile | Pro | Pro | Leu | Phe | Pro | Ile | Lys | Ser | Phe | Val | Lys | Thr |
| | | 980 | | | | 985 | | | | 990 | | | | |
| Lys | Cys | Lys | Lys | Asn | Leu | Leu | Glu | Glu | Asn | Phe | Glu | Glu | His | Ser | Met |
| | | 995 | | | | 1000 | | | | 1005 | | | | |
| Ser | Pro | Glu | Arg | Glu | Met | Gly | Asn | Glu | Asn | Ile | Pro | Ser | Thr | Val | Ser |
| | 1010 | | | | | 1015 | | | | 1020 | | | | |
| Thr | Ile | Ser | Arg | Asn | Asn | Ile | Arg | Glu | Asn | Val | Phe | Lys | Glu | Ala | Ser |
| 1025 | | | | 1030 | | | | 1035 | | | | | | 1040 |
| Ser | Ser | Asn | Ile | Asn | Glu | Val | Gly | Ser | Ser | Thr | Asn | Glu | Val | Gly | Ser |
| | | | 1045 | | | | 1050 | | | | 1055 | | | |
| Ser | Ile | Asn | Glu | Ile | Gly | Ser | Ser | Asp | Glu | Asn | Ile | Gln | Ala | Glu | Leu |
| | | | 1060 | | | | 1065 | | | | 1070 | | | |
| Gly | Arg | Asn | Arg | Gly | Pro | Lys | Leu | Asn | Ala | Met | Leu | Arg | Leu | Gly | Val |
| | | 1075 | | | | 1080 | | | | 1085 | | | | |
| Leu | Gln | Pro | Glu | Val | Tyr | Lys | Gln | Ser | Leu | Pro | Gly | Ser | Asn | Cys | Lys |
| | 1090 | | | | 1095 | | | | 1100 | | | | | |
| His | Pro | Glu | Ile | Lys | Lys | Gln | Glu | Tyr | Glu | Glu | Val | Val | Gln | Thr | Val |
| 1105 | | | | 1110 | | | | 1115 | | | | | | 1120 |
| Asn | Thr | Asp | Phe | Ser | Pro | Tyr | Leu | Ile | Ser | Asp | Asn | Leu | Glu | Gln | Pro |
| | | | 1125 | | | | 1130 | | | | 1135 | | | |

Met Gly Ser Ser His Ala Ser Gln Val Cys Ser Glu Thr Pro Asp Asp
              1140                1145                1150

Leu Leu Asp Asp Gly Glu Ile Lys Glu Asp Thr Ser Phe Ala Glu Asn
              1155                1160                1165

Asp Ile Lys Glu Ser Ser Ala Val Phe Ser Lys Ser Val Gln Lys Gly
1170                1175                1180

Glu Leu Ser Arg Ser Pro Ser Pro Phe Thr His Thr His Leu Ala Gln
1185                1190                1195                1200

Gly Tyr Arg Arg Gly Ala Lys Lys Leu Glu Ser Ser Glu Glu Asn Leu
              1205                1210                1215

Ser Ser Glu Asp Glu Glu Leu Pro Cys Phe Gln His Leu Leu Phe Gly
              1220                1225                1230

Lys Val Asn Asn Ile Pro Ser Gln Ser Thr Arg His Ser Thr Val Ala
              1235                1240                1245

Thr Glu Cys Leu Ser Lys Asn Thr Glu Glu Asn Leu Leu Ser Leu Lys
              1250                1255                1260

Asn Ser Leu Asn Asp Cys Ser Asn Gln Val Ile Leu Ala Lys Ala Ser
1265                1270                1275                1280

Gln Glu His His Leu Ser Glu Glu Thr Lys Cys Ser Ala Ser Leu Phe
                    1285                1290                1295

Ser Ser Gln Cys Ser Glu Leu Glu Asp Leu Thr Ala Asn Thr Asn Thr
              1300                1305                1310

Gln Asp Pro Phe Leu Ile Gly Ser Ser Lys Gln Met Arg His Gln Ser
              1315                1320                1325

Glu Ser Gln Gly Val Gly Leu Ser Asp Lys Glu Leu Val Ser Asp Asp
              1330                1335                1340

Glu Glu Arg Gly Thr Gly Leu Glu Glu Asn Asn Gln Glu Glu Gln Ser
1345                1350                1355                1360

Met Asp Ser Asn Leu Gly Glu Ala Ala Ser Gly Cys Glu Ser Glu Thr
              1365                1370                1375

Ser Val Ser Glu Asp Cys Ser Gly Leu Ser Ser Gln Ser Asp Ile Leu
              1380                1385                1390

Thr Thr Gln Gln Arg Asp Thr Met Gln His Asn Leu Ile Lys Leu Gln
              1395                1400                1405

Gln Glu Met Ala Glu Leu Glu Ala Val Leu Glu Gln His Gly Ser Gln
              1410                1415                1420

Pro Ser Asn Ser Tyr Pro Ser Ile Ile Ser Asp Ser Ser Ala Leu Glu
1425                1430                1435                1440

Asp Leu Arg Asn Pro Glu Gln Ser Thr Ser Glu Lys Val Leu Gln Thr
              1445                1450                1455

Ser Gln Lys Ser Ser Glu Tyr Pro Ile Ser Gln Asn Pro Glu Gly Xaa
              1460                1465                1470

Ser Ala Asp Lys Phe Glu Val Ser Ala Asp Ser Ser Thr Ser Lys Asn
              1475                1480                1485

Lys Glu Pro Gly Val Glu Arg Ser Ser Pro Ser Lys Cys Pro Ser Leu
              1490                1495                1500

Asp Asp Arg Trp Tyr Met His Ser Cys Ser Gly Ser Leu Gln Asn Arg
1505                1510                1515                1520

Asn Tyr Pro Pro Gln Glu Glu Leu Ile Lys Val Val Asp Val Glu Glu
              1525                1530                1535

Gln Gln Leu Glu Glu Ser Gly Pro His Asp Leu Thr Glu Thr Ser Tyr
              1540                1545                1550

```
Leu  Pro  Arg  Gln  Asp  Leu  Glu  Gly  Thr  Pro  Tyr  Leu  Glu  Ser  Gly  Ile
          1555                1560                     1565

Ser  Leu  Phe  Ser  Asp  Asp  Pro  Glu  Ser  Asp  Pro  Ser  Glu  Asp  Arg  Ala
          1570                1575                     1580

Pro  Glu  Ser  Ala  Arg  Val  Gly  Asn  Ile  Pro  Ser  Ser  Thr  Ser  Ala  Leu
1585                     1590                     1595                          1600

Lys  Val  Pro  Gln  Leu  Lys  Val  Ala  Glu  Ser  Ala  Gln  Ser  Pro  Ala  Ala
                    1605                     1610                     1615

Ala  His  Thr  Thr  Asp  Thr  Ala  Gly  Tyr  Asn  Ala  Met  Glu  Glu  Ser  Val
                    1620                     1625                     1630

Ser  Arg  Glu  Lys  Pro  Glu  Leu  Thr  Ala  Ser  Thr  Glu  Arg  Val  Asn  Lys
               1635                1640                     1645

Arg  Met  Ser  Met  Val  Val  Ser  Gly  Leu  Thr  Pro  Glu  Glu  Phe  Met  Leu
          1650                1655                     1660

Val  Tyr  Lys  Phe  Ala  Arg  Lys  His  His  Ile  Thr  Leu  Thr  Asn  Leu  Ile
1665                     1670                     1675                          1680

Thr  Glu  Glu  Thr  Thr  His  Val  Val  Met  Lys  Thr  Asp  Ala  Glu  Phe  Val
                    1685                     1690                     1695

Cys  Glu  Arg  Thr  Leu  Lys  Tyr  Phe  Leu  Gly  Ile  Ala  Gly  Gly  Lys  Trp
               1700                1705                     1710

Val  Val  Ser  Tyr  Phe  Trp  Val  Thr  Gln  Ser  Ile  Lys  Glu  Arg  Lys  Met
          1715                1720                     1725

Leu  Asn  Glu  His  Asp  Phe  Glu  Val  Arg  Gly  Asp  Val  Val  Asn  Gly  Arg
          1730                1735                     1740

Asn  His  Gln  Gly  Pro  Lys  Arg  Ala  Arg  Glu  Ser  Gln  Asp  Arg  Lys  Ile
1745                     1750                     1755                          1760

Phe  Arg  Gly  Leu  Glu  Ile  Cys  Cys  Tyr  Gly  Pro  Phe  Thr  Asn  Met  Pro
                    1765                     1770                     1775

Thr  Asp  Gln  Leu  Glu  Trp  Met  Val  Gln  Leu  Cys  Gly  Ala  Ser  Val  Val
               1780                1785                     1790

Lys  Glu  Leu  Ser  Ser  Phe  Thr  Leu  Gly  Thr  Gly  Val  His  Pro  Ile  Val
          1795                1800                     1805

Val  Val  Gln  Pro  Asp  Ala  Trp  Thr  Glu  Asp  Asn  Gly  Phe  His  Ala  Ile
          1810                1815                     1820

Gly  Gln  Met  Cys  Glu  Ala  Pro  Val  Val  Thr  Arg  Glu  Trp  Val  Leu  Asp
1825                     1830                     1835                          1840

Ser  Val  Ala  Leu  Tyr  Gln  Cys  Gln  Glu  Leu  Asp  Thr  Tyr  Leu  Ile  Pro
                    1845                     1850                     1855

Gln  Ile  Pro  His  Ser  His  Tyr
                    1860
```

( 2 ) INFORMATION FOR SEQ ID NO:3:

( i ) SEQUENCE CHARACTERISTICS:
        ( A ) LENGTH: 11283
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: no ( i v ) ANTI-SENSE: no ( v ) ORIGINAL SOURCE:
        ( A ) ORGANISM: Homo sapiens sapiens
        ( C ) INDIVIDUAL ISOLATE:
        ( D ) DEVELOPMENTAL STAGE: adult
        ( F ) TISSUE TYPE: female breast (G) CELL TYPE: normal and cancerous breast cells
(H) CELL LINE: MCF-7
(I) ORGANELLE: no (vii) IMMEDIATE SOURCE:
(A) LIBRARY: cDNA library derived from human
(B) CLONE: obtained using published sequence (viii) POSITION IN GENOME:
(A) CHROMOSOME/SEGMENT: unknown
(B) MAP POSITION: unknown
(C) UNITS: unknown (ix) FEATURE:
(A) NAME/KEY: BRCA2
(B) LOCATION:
(C) IDENTIFICATION METHOD:
(D) OTHER INFORMATION: gene encoding BRCA2 protein (x) PUBLICATION INFORMATION:
(A) AUTHORS: Wooster, R. et al.
(B) TITLE: Identification of the breast cancer
susceptability gene BRCA2
(C) JOURNAL: Nature
(D) VOLUME: 379
(E) PAGES: 789-792
(F) DATE: 1995
(K) RELEVANT RESIDUES IN SEQ ID NO:3

(xi) SEQUENCE DESCRIPTION: SEQ ID NO:3:

```
ggcggagccg ctgtggcact gctgcgcctc tgctgcgcct cgggtgtctt ttgcggcggt      60
gggtcgccgc cgggagaagc gtgaggggac agatttgtga ccggcgcggt ttttgtcagc     120
ttactccggc caaaaaagaa ctgcacctct ggagcggact tatttaccaa gcattggagg     180
aatatcgtag gtaaaa                                                     196 atg  cct  att  gga  tcc  aaa  gag  agg  cca  aca  ttt  ttt  gaa  att  ttt  aag     244
Met  Pro  Ile  Gly  Ser  Lys  Glu  Arg  Pro  Thr  Phe  Phe  Glu  Ile  Phe  Lys
 1             5                        10                       15 aca  cgc  tgc  aac  aaa  gca  gat  tta  gga  cca  ata  agt  ctt  aat  tgg  ttt     292
Thr  Arg  Cys  Asn  Lys  Ala  Asp  Leu  Gly  Pro  Ile  Ser  Leu  Asn  Trp  Phe
              20                        25                       30 gaa  gaa  ctt  tct  tca  gaa  gct  cca  ccc  tat  aat  tct  gaa  cct  gca  gaa     340
Glu  Glu  Leu  Ser  Ser  Glu  Ala  Pro  Pro  Tyr  Asn  Ser  Glu  Pro  Ala  Glu
              35                        40                       45 gaa  tct  gaa  cat  aaa  aac  aac  aat  tac  gaa  cca  aac  cta  ttt  aaa  act     388
Glu  Ser  Glu  His  Lys  Asn  Asn  Asn  Tyr  Glu  Pro  Asn  Leu  Phe  Lys  Thr
      50                        55                        60 cca  caa  agg  aaa  cca  tct  tat  aat  cag  ctg  gct  tca  act  cca  ata  ata     436
Pro  Gln  Arg  Lys  Pro  Ser  Tyr  Asn  Gln  Leu  Ala  Ser  Thr  Pro  Ile  Ile
65                        70                        75                       80 ttc  aaa  gag  caa  ggg  ctg  act  ctg  ccg  ctg  tac  caa  tct  cct  gta  aaa     484
Phe  Lys  Glu  Gln  Gly  Leu  Thr  Leu  Pro  Leu  Tyr  Gln  Ser  Pro  Val  Lys
                          85                        90                       95 gaa  tta  gat  aaa  ttc  aaa  tta  gac  tta  gga  agg  aat  gtt  ccc  aat  agt     532
Glu  Leu  Asp  Lys  Phe  Lys  Leu  Asp  Leu  Gly  Arg  Asn  Val  Pro  Asn  Ser
                  100                       105                      110 aga  cat  aaa  agt  ctt  cgc  aca  gtg  aaa  act  aaa  atg  gat  caa  gca  gat     580
Arg  His  Lys  Ser  Leu  Arg  Thr  Val  Lys  Tyr  Lys  Met  Asp  Gln  Ala  Asp
                  115                       120                      125 gat  gtt  tcc  tgt  cca  ctt  cta  aat  tct  tgt  ctt  agt  gaa  agt  cct  gtt     628
Asp  Val  Ser  Cys  Pro  Leu  Leu  Asn  Ser  Cys  Leu  Ser  Glu  Ser  Pro  Val
      130                       135                       140 gtt  cta  caa  tgt  aca  cat  gta  aca  cca  caa  aga  gat  aag  tca  gtg  gta     676
Val  Leu  Gln  Cys  Thr  His  Val  Thr  Pro  Gln  Arg  Asp  Lys  Ser  Val  Val
145                       150                       155                      160
```

| | | | | | | | | | | | | | | | | |
|---|---|---|---|---|---|---|---|---|---|---|---|---|---|---|---|---|
| tgt | ggg | agt | ttg | ttt | cat | aca | cca | aag | ttt | gtg | aag | ggt | cgt | cag | aca | 724 |
| Cys | Gly | Ser | Leu 165 | Phe | His | Thr | Pro | Lys 170 | Phe | Val | Lys | Gly | Arg 175 | Gln | Thr | |
| cca | aaa | cat | att | tct | gaa | agt | cta | gga | gct | gag | gtg | gat | cct | gat | atg | 772 |
| Pro | Lys | His | Ile 180 | Ser | Glu | Ser | Leu | Gly 185 | Ala | Glu | Val | Asp | Pro 190 | Asp | Met | |
| tct | tgg | tca | agt | tct | tta | gct | aca | cca | ccc | acc | ctt | agt | tct | act | gtg | 820 |
| Ser | Trp | Ser 195 | Ser | Ser | Leu | Ala | Thr 200 | Pro | Pro | Thr | Leu | Ser 205 | Ser | Thr | Val | |
| ctc | ata | gtc | aga | aat | gaa | gaa | gca | tct | gaa | act | gta | ttt | cct | cat | gat | 868 |
| Leu | Ile | Val 210 | Arg | Asn | Glu | Glu | Ala 215 | Ser | Glu | Thr | Val | Phe 220 | Pro | His | Asp | |
| act | act | gct | aat | gtg | aaa | agc | tat | ttt | tcc | aat | cat | gat | gaa | agt | ctg | 916 |
| Thr 225 | Thr | Ala | Asn | Val 230 | Lys | Ser | Tyr | Phe | Ser 235 | Asn | His | Asp | Glu | Ser 240 | Leu | |
| aag | aaa | aat | gat | aga | ttt | atc | gct | tct | gtg | aca | gac | agt | gaa | aac | aca | 964 |
| Lys | Lys | Asn | Asp | Arg 245 | Phe | Ile | Ala | Ser | Val 250 | Thr | Asp | Ser | Glu | Asn 255 | Thr | |
| aat | caa | aga | gaa | gct | gca | agt | cat | gga | ttt | gga | aaa | aca | tca | ggg | aat | 1012 |
| Asn | Gln | Arg | Glu 260 | Ala | Ala | Ser | His | Gly 265 | Phe | Gly | Lys | Thr | Ser 270 | Gly | Asn | |
| tca | ttt | aaa | gta | aat | agc | tgc | aaa | gac | cac | att | gga | aag | tca | atg | cca | 1060 |
| Ser | Phe | Lys 275 | Val | Asn | Ser | Cys | Lys 280 | Asp | His | Ile | Gly | Lys 285 | Ser | Met | Pro | |
| aat | gtc | cta | gaa | gat | gaa | gta | tat | gaa | aca | gtt | gta | gat | acc | tct | gaa | 1108 |
| Asn | Val | Leu | Glu 290 | Asp | Glu | Val | Tyr | Glu 295 | Thr | Val | Val | Asp | Thr 300 | Ser | Glu | |
| gaa | gat | agt | ttt | tca | tta | tgt | ttt | tct | aaa | tgt | aga | aca | aaa | aat | cta | 1156 |
| Glu 305 | Asp | Ser | Phe | Ser | Leu 310 | Cys | Phe | Ser | Lys | Cys 315 | Arg | Thr | Lys | Asn | Leu 320 | |
| caa | aaa | gta | aga | act | agc | aag | act | agg | aaa | aaa | att | ttc | cat | gaa | gca | 1204 |
| Gln | Lys | Val | Arg | Thr 325 | Ser | Lys | Thr | Arg | Lys 330 | Lys | Ile | Phe | His | Glu 335 | Ala | |
| aac | gct | gat | gaa | tgt | gaa | aaa | tct | aaa | aac | caa | gtg | aaa | gaa | aaa | tac | 1252 |
| Asn | Ala | Asp | Glu 340 | Cys | Glu | Lys | Ser | Lys 345 | Asn | Gln | Val | Lys | Glu 350 | Lys | Tyr | |
| tca | ttt | gta | tct | gaa | gtg | gaa | cca | aat | gat | act | gat | cca | tta | gat | tca | 1300 |
| Ser | Phe | Val 355 | Ser | Glu | Val | Glu | Pro 360 | Asn | Asp | Thr | Asp | Pro 365 | Leu | Asp | Ser | |
| aat | gta | gca | cat | cag | aag | ccc | ttt | gag | agt | gga | agt | gac | aaa | atc | tcc | 1348 |
| Asn | Val | Ala | His 370 | Gln | Lys | Pro | Phe | Glu 375 | Ser | Gly | Ser | Asp | Lys 380 | Ile | Ser | |
| aag | gaa | gtt | gta | ccg | tct | ttg | gcc | tgt | gaa | tgg | tct | caa | cta | acc | ctt | 1396 |
| Lys 385 | Glu | Val | Val | Pro | Ser 390 | Leu | Ala | Cys | Glu | Trp 395 | Ser | Gln | Leu | Thr | Leu 400 | |
| tca | ggt | cta | aat | gga | gcc | cag | atg | gag | aaa | ata | ccc | cta | ttg | cat | att | 1444 |
| Ser | Gly | Leu | Asn | Gly 405 | Ala | Gln | Met | Glu | Lys 410 | Ile | Pro | Leu | Leu | His 415 | Ile | |
| tct | tca | tgt | gac | caa | aat | att | tca | gaa | aaa | gac | cta | tta | gac | aca | gag | 1492 |
| Ser | Ser | Cys | Asp 420 | Gln | Asn | Ile | Ser | Glu 425 | Lys | Asp | Leu | Leu | Asp 430 | Thr | Glu | |
| aac | aaa | aga | aag | aaa | gat | ttt | ctt | act | tca | gag | aat | tct | ttg | cca | cgt | 1540 |
| Asn | Lys | Arg | Lys 435 | Lys | Asp | Phe | Leu | Thr 440 | Ser | Glu | Asn | Ser | Leu 445 | Pro | Arg | |
| att | tct | agc | cta | cca | aaa | tca | gag | aag | cca | tta | aat | gag | gaa | aca | gtg | 1588 |
| Ile | Ser | Ser | Leu 450 | Pro | Lys | Ser | Glu | Lys 455 | Pro | Leu | Asn | Glu | Glu 460 | Thr | Val | |
| gta | aat | aag | aga | gat | gaa | gag | cag | cat | ctt | gaa | tct | cat | aca | gac | tgc | 1636 |
| Val | Asn 465 | Lys | Arg | Asp | Glu | Glu 470 | Gln | His | Leu | Glu | Ser 475 | His | Thr | Asp | Cys 480 | |

```
att ctt gca gta aag cag gca ata tct gga act tct cca gtg gct tct    1684
Ile Leu Ala Val Lys Gln Ala Ile Ser Gly Thr Ser Pro Val Ala Ser
                485                 490                 495 tca ttt cag ggt atc aaa aag tct ata ttc aga ata aga gaa tca cct    1732
Ser Phe Gln Gly Ile Lys Lys Ser Ile Phe Arg Ile Arg Glu Ser Pro
            500                 505                 510 aaa gag act ttc aat gca agt ttt tca ggt cat atg act gat cca aac    1780
Lys Glu Thr Phe Asn Ala Ser Phe Ser Gly His Met Thr Asp Pro Asn
        515                 520                 525 ttt aaa aaa gaa act gaa gcc tct gaa agt gga ctg gaa ata cat act    1828
Phe Lys Lys Glu Thr Glu Ala Ser Glu Ser Gly Leu Glu Ile His Thr
530                 535                 540 gtt tgc tca cag aag gag gac tcc tta tgt cca aat tta att gat aat    1876
Val Cys Ser Gln Lys Glu Asp Ser Leu Cys Pro Asn Leu Ile Asp Asn
545                 550                 555                 560 gga agc tgg cca gcc acc acc aca cag aat tct gta gct ttg aag aat    1924
Gly Ser Trp Pro Ala Thr Thr Thr Gln Asn Ser Val Ala Leu Lys Asn
                565                 570                 575 gca ggt tta ata tcc act ttg aaa aag aaa aca aat aag ttt att tat    1972
Ala Gly Leu Ile Ser Thr Leu Lys Lys Lys Thr Asn Lys Phe Ile Tyr
            580                 585                 590 gct ata cat gat gaa aca ttt tat aaa gga aaa aaa ata ccg aaa gac    2020
Ala Ile His Asp Glu Thr Phe Tyr Lys Gly Lys Lys Ile Pro Lys Asp
        595                 600                 605 caa aaa tca gaa cta att aac tgt tca gcc cag ttt gaa gca aat gct    2068
Gln Lys Ser Glu Leu Ile Asn Cys Ser Ala Gln Phe Glu Ala Asn Ala
610                 615                 620 ttt gaa gca cca ctt aca ttt gca aat gct gat tca ggt tta ttg cat    2116
Phe Glu Ala Pro Leu Thr Phe Ala Asn Ala Asp Ser Gly Leu Leu His
625                 630                 635                 640 tct tct gtg aaa aga agc tgt tca cag aat gat tct gaa gaa cca act    2164
Ser Ser Val Lys Arg Ser Cys Ser Gln Asn Asp Ser Glu Glu Pro Thr
                645                 650                 655 ttg tcc tta act agc tct ttt ggg aca att ctg agg aaa tgt tct aga    2212
Leu Ser Leu Thr Ser Ser Phe Gly Thr Ile Leu Arg Lys Cys Ser Arg
            660                 665                 670 aat gaa aca tgt tct aat aat aca gta atc tct cag gat ctt gat tat    2260
Asn Glu Thr Cys Ser Asn Asn Thr Val Ile Ser Gln Asp Leu Asp Tyr
        675                 680                 685 aaa gaa gca aaa tgt aat aag gaa aaa cta cag tta ttt att acc cca    2308
Lys Glu Ala Lys Cys Asn Lys Glu Lys Leu Gln Leu Phe Ile Thr Pro
690                 695                 700 gaa gct gat tct ctg tca tgc ctg cag gaa gga cag tgt gaa aat gat    2356
Glu Ala Asp Ser Leu Ser Cys Leu Gln Glu Gly Gln Cys Glu Asn Asp
705                 710                 715                 720 cca aaa agc aaa aaa gtt tca gat ata aaa gaa gag gtc ttg gct gca    2404
Pro Lys Ser Lys Lys Val Ser Asp Ile Lys Glu Glu Val Leu Ala Ala
                725                 730                 735 gca tgt cac cca gta caa cat tca aaa gtg gaa tac agt gat act gac    2452
Ala Cys His Pro Val Gln His Ser Lys Val Glu Tyr Ser Asp Thr Asp
            740                 745                 750 ttt caa tcc cag aaa agt ctt tta tat gat cat gaa aat gcc agc act    2500
Phe Gln Ser Gln Lys Ser Leu Leu Tyr Asp His Glu Asn Ala Ser Thr
        755                 760                 765 ctt att tta act cct act tcc aag gat gtt ctg tca aac cta gtc atg    2548
Leu Ile Leu Thr Pro Thr Ser Lys Asp Val Leu Ser Asn Leu Val Met
770                 775                 780 att tct aga ggc aaa gaa tca tac aaa atg tca gac aag ctc aaa ggt    2596
Ile Ser Arg Gly Lys Glu Ser Tyr Lys Met Ser Asp Lys Leu Lys Gly
785                 790                 795                 800
```

| | | | | | | | | | | | | | | | | |
|---|---|---|---|---|---|---|---|---|---|---|---|---|---|---|---|---|
| aac | aat | tat | gaa | tct | gat | gtt | gaa | tta | acc | aaa | aat | att | ccc | atg | gaa | 2644 |
| Asn | Asn | Tyr | Glu | Ser | Asp | Val | Glu | Leu | Thr | Lys | Asn | Ile | Pro | Met | Glu | |
| | | | | 805 | | | | 810 | | | | | | 815 | | |
| aag | aat | caa | gat | gta | tgt | gct | tta | aat | gaa | aat | tat | aaa | aac | gtt | gag | 2692 |
| Lys | Asn | Gln | Asp | Val | Cys | Ala | Leu | Asn | Glu | Asn | Tyr | Lys | Asn | Val | Glu | |
| | | | 820 | | | | | 825 | | | | | 830 | | | |
| ctg | ttg | cca | cct | gaa | aaa | tac | atg | aga | gta | gca | tca | cct | tca | aga | aag | 2740 |
| Leu | Leu | Pro | Pro | Glu | Lys | Tyr | Met | Arg | Val | Ala | Ser | Pro | Ser | Arg | Lys | |
| | | | 835 | | | | | 840 | | | | | 845 | | | |
| gta | caa | ttc | aac | caa | aac | aca | aat | cta | aga | gta | atc | caa | aaa | aat | caa | 2788 |
| Val | Gln | Phe | Asn | Gln | Asn | Thr | Asn | Leu | Arg | Val | Ile | Gln | Lys | Asn | Gln | |
| | | | | 850 | | | | | 855 | | | | | 860 | | |
| gaa | gaa | act | act | tca | att | tca | aaa | ata | act | gtc | aat | cca | gac | tct | gaa | 2836 |
| Glu | Glu | Thr | Thr | Ser | Ile | Ser | Lys | Ile | Thr | Val | Asn | Pro | Asp | Ser | Glu | |
| 865 | | | | | 870 | | | | | 875 | | | | | 880 | |
| gaa | ctt | ttc | tca | gac | aat | gag | aat | aat | ttt | gtc | ttc | caa | gta | gct | aat | 2884 |
| Glu | Leu | Phe | Ser | Asp | Asn | Glu | Asn | Asn | Phe | Val | Phe | Gln | Val | Ala | Asn | |
| | | | | 885 | | | | | 890 | | | | | 895 | | |
| gaa | agg | aat | aat | ctt | gct | tta | gga | aat | act | aag | gaa | ctt | cat | gaa | aca | 2932 |
| Glu | Arg | Asn | Asn | Leu | Ala | Leu | Gly | Asn | Thr | Lys | Glu | Leu | His | Glu | Thr | |
| | | | 900 | | | | | 905 | | | | | 910 | | | |
| gac | ttg | act | tgt | gta | aac | gaa | ccc | att | ttc | aag | aac | tct | acc | atg | gtt | 2980 |
| Asp | Leu | Thr | Cys | Val | Asn | Glu | Pro | Ile | Phe | Lys | Asn | Ser | Thr | Met | Val | |
| | | | 915 | | | | | 920 | | | | | 925 | | | |
| tta | tat | gga | gac | aca | ggt | gat | aaa | caa | gca | acc | caa | gtg | tca | att | aaa | 3028 |
| Leu | Tyr | Gly | Asp | Thr | Gly | Asp | Lys | Gln | Ala | Thr | Gln | Val | Ser | Ile | Lys | |
| | | 930 | | | | | 935 | | | | | 940 | | | | |
| aaa | gat | ttg | gtt | tat | gtt | ctt | gca | gag | gag | aac | aaa | aat | agt | gta | aag | 3076 |
| Lys | Asp | Leu | Val | Tyr | Val | Leu | Ala | Glu | Glu | Asn | Lys | Asn | Ser | Val | Lys | |
| 945 | | | | | 950 | | | | | 955 | | | | | 960 | |
| cag | cat | ata | aaa | atg | act | cta | ggt | caa | gat | tta | aaa | tcg | gac | atc | tcc | 3124 |
| Gln | His | Ile | Lys | Met | Thr | Leu | Gly | Gln | Asp | Leu | Lys | Ser | Asp | Ile | Ser | |
| | | | | 965 | | | | | 970 | | | | | 975 | | |
| ttg | aat | ata | gat | aaa | ata | cca | gaa | aaa | aat | aat | gat | tac | atg | aac | aaa | 3172 |
| Leu | Asn | Ile | Asp | Lys | Ile | Pro | Glu | Lys | Asn | Asn | Asp | Tyr | Met | Asn | Lys | |
| | | | 980 | | | | | 985 | | | | | 990 | | | |
| tgg | gca | gga | ctc | tta | ggt | cca | att | tca | aat | cac | agt | ttt | gga | ggt | agc | 3220 |
| Trp | Ala | Gly | Leu | Leu | Gly | Pro | Ile | Ser | Asn | His | Ser | Phe | Gly | Gly | Ser | |
| | | 995 | | | | | 1000 | | | | | 1005 | | | | |
| ttc | aga | aca | gct | tca | aat | aag | gaa | atc | aag | ctc | tct | gaa | cat | aac | att | 3268 |
| Phe | Arg | Thr | Ala | Ser | Asn | Lys | Glu | Ile | Lys | Leu | Ser | Glu | His | Asn | Ile | |
| | | | 1010 | | | | | 1015 | | | | | 1020 | | | |
| aag | aag | agc | aaa | atg | ttc | ttc | aaa | gat | att | gaa | gaa | caa | tat | cct | act | 3316 |
| Lys | Lys | Ser | Lys | Met | Phe | Phe | Lys | Asp | Ile | Glu | Glu | Gln | Tyr | Pro | Thr | |
| 1025 | | | | | 1030 | | | | | 1035 | | | | | 1040 | |
| agt | tta | gct | tgt | gtt | gaa | att | gta | aat | acc | ttg | gca | tta | gat | aat | caa | 3364 |
| Ser | Leu | Ala | Cys | Val | Glu | Ile | Val | Asn | Thr | Leu | Ala | Leu | Asp | Asn | Gln | |
| | | | | 1045 | | | | | 1050 | | | | | 1055 | | |
| aag | aaa | ctg | agc | aag | cct | cag | tca | att | aat | act | gta | tct | gca | cat | tta | 3412 |
| Lys | Lys | Leu | Ser | Lys | Pro | Gln | Ser | Ile | Asn | Thr | Val | Ser | Ala | His | Leu | |
| | | | | 1060 | | | | | 1065 | | | | | 1070 | | |
| cag | agt | agt | gta | gtt | gtt | tct | gat | tgt | aaa | aat | agt | cat | ata | acc | cct | 3460 |
| Gln | Ser | Ser | Val | Val | Val | Ser | Asp | Cys | Lys | Asn | Ser | His | Ile | Thr | Pro | |
| | | | 1075 | | | | | 1080 | | | | | 1085 | | | |
| cag | atg | tta | ttt | tcc | aag | cag | gat | ttt | aat | tca | aac | cat | aat | tta | aca | 3508 |
| Gln | Met | Leu | Phe | Ser | Lys | Gln | Asp | Phe | Asn | Ser | Asn | His | Asn | Leu | Thr | |
| | | | 1090 | | | | | 1095 | | | | | 1100 | | | |
| cct | agc | caa | aag | gca | gaa | att | aca | gaa | ctt | tct | act | ata | tta | gaa | gaa | 3556 |
| Pro | Ser | Gln | Lys | Ala | Glu | Ile | Thr | Glu | Leu | Ser | Thr | Ile | Leu | Glu | Glu | |
| 1105 | | | | | 1110 | | | | | 1115 | | | | | 1120 | |

```
tca  gga  agt  cag  ttt  gaa  ttt  act  cag  ttt  aga  aaa  cca  agc  tac  ata    3604
Ser  Gly  Ser  Gln  Phe  Glu  Phe  Thr  Gln  Phe  Arg  Lys  Pro  Ser  Tyr  Ile
               1125                1130                1135 ttg  cag  aag  agt  aca  ttt  gaa  gtg  cct  gaa  aac  cag  atg  act  atc  tta    3652
Leu  Gln  Lys  Ser  Thr  Phe  Glu  Val  Pro  Glu  Asn  Gln  Met  Thr  Ile  Leu
               1140                1145                1150 aag  acc  act  tct  gag  gaa  tgc  aga  gat  gct  gat  ctt  cat  gtc  ata  atg    3700
Lys  Thr  Thr  Ser  Glu  Glu  Cys  Arg  Asp  Ala  Asp  Leu  His  Val  Ile  Met
               1155                1160                1165 aat  gcc  cca  tcg  att  ggt  cag  gta  gac  agc  agc  aag  caa  ttt  gaa  ggt    3748
Asn  Ala  Pro  Ser  Ile  Gly  Gln  Val  Asp  Ser  Ser  Lys  Gln  Phe  Glu  Gly
               1170                1175                1180 aca  gtt  gaa  att  aaa  cgg  aag  ttt  gct  ggc  ctg  ttg  aaa  aat  gac  tgt    3796
Thr  Val  Glu  Ile  Lys  Arg  Lys  Phe  Ala  Gly  Leu  Leu  Lys  Asn  Asp  Cys
1185                1190                1195                1200 aac  aaa  agt  gct  tct  ggt  tat  tta  aca  gat  gaa  aat  gaa  gtg  ggg  ttt    3844
Asn  Lys  Ser  Ala  Ser  Gly  Tyr  Leu  Thr  Asp  Glu  Asn  Glu  Val  Gly  Phe
               1205                1210                1215 agg  ggc  ttt  tat  tct  gct  cat  ggc  aca  aaa  ctg  aat  gtt  tct  act  gaa    3892
Arg  Gly  Phe  Tyr  Ser  Ala  His  Gly  Thr  Lys  Leu  Asn  Val  Ser  Thr  Glu
               1220                1225                1230 gct  ctg  caa  aaa  gct  gtg  aaa  ctg  ttt  agt  gat  att  gag  aat  att  agt    3940
Ala  Leu  Gln  Lys  Ala  Val  Lys  Leu  Phe  Ser  Asp  Ile  Glu  Asn  Ile  Ser
               1235                1240                1245 gag  gaa  act  tct  gca  gag  gta  cat  cca  ata  agt  tta  tct  tca  agt  aaa    3988
Glu  Glu  Thr  Ser  Ala  Glu  Val  His  Pro  Ile  Ser  Leu  Ser  Ser  Ser  Lys
               1250                1255                1260 tgt  cat  gat  tct  gtt  gtt  tca  atg  ttt  aag  ata  gaa  aat  cat  aat  gat    4036
Cys  His  Asp  Ser  Val  Val  Ser  Met  Phe  Lys  Ile  Glu  Asn  His  Asn  Asp
1265                1270                1275                1280 aaa  act  gta  agt  gaa  aaa  aat  aat  aaa  tgc  caa  ctg  ata  tta  caa  aat    4084
Lys  Thr  Val  Ser  Glu  Lys  Asn  Asn  Lys  Cys  Gln  Leu  Ile  Leu  Gln  Asn
               1285                1290                1295 aat  att  gaa  atg  act  act  ggc  act  ttt  gtt  gaa  gaa  att  act  gaa  aat    4132
Asn  Ile  Glu  Met  Thr  Thr  Gly  Thr  Phe  Val  Glu  Glu  Ile  Thr  Glu  Asn
               1300                1305                1310 tac  aag  aga  aat  act  gaa  aat  gaa  gat  aac  aaa  tat  act  gct  gcc  agt    4180
Tyr  Lys  Arg  Asn  Thr  Glu  Asn  Glu  Asp  Asn  Lys  Tyr  Thr  Ala  Ala  Ser
               1315                1320                1325 aga  aat  tct  cat  aac  tta  gaa  ttt  gat  ggc  agt  gat  tca  agt  aaa  aat    4228
Arg  Asn  Ser  His  Asn  Leu  Glu  Phe  Asp  Gly  Ser  Asp  Ser  Ser  Lys  Asn
               1330                1335                1340 gat  act  gtt  tgt  att  cat  aaa  gat  gaa  acg  gac  ttg  cta  ttt  act  gat    4276
Asp  Thr  Val  Cys  Ile  His  Lys  Asp  Glu  Thr  Asp  Leu  Leu  Phe  Thr  Asp
1345                1350                1355                1360 cag  cac  aac  ata  tgt  ctt  aaa  tta  tct  ggc  cag  ttt  atg  aag  gag  gga    4324
Gln  His  Asn  Ile  Cys  Leu  Lys  Leu  Ser  Gly  Gln  Phe  Met  Lys  Glu  Gly
               1365                1370                1375 aac  act  cag  att  aaa  gaa  gat  ttg  tca  gat  tta  act  ttt  ttg  gaa  gtt    4372
Asn  Thr  Gln  Ile  Lys  Glu  Asp  Leu  Ser  Asp  Leu  Thr  Phe  Leu  Glu  Val
               1380                1385                1390 gcg  aaa  gct  caa  gaa  gca  tgt  cat  ggt  aat  act  tca  aat  aaa  gaa  cag    4420
Ala  Lys  Ala  Gln  Glu  Ala  Cys  His  Gly  Asn  Thr  Ser  Asn  Lys  Glu  Gln
               1395                1400                1405 tta  act  gct  act  aaa  acg  gag  caa  aat  ata  aaa  gat  ttt  gag  act  tct    4468
Leu  Thr  Ala  Thr  Lys  Thr  Glu  Gln  Asn  Ile  Lys  Asp  Phe  Glu  Thr  Ser
               1410                1415                1420 gat  aca  ttt  ttt  cag  act  gca  agt  ggg  aaa  aat  att  agt  gtc  gcc  aaa    4516
Asp  Thr  Phe  Phe  Gln  Thr  Ala  Ser  Gly  Lys  Asn  Ile  Ser  Val  Ala  Lys
1425                1430                1435                1440
```

```
gag  tta  ttt  aat  aaa  att  gta  aat  ttc  ttt  gat  cag  aaa  cca  gaa  gaa        4564
Glu  Leu  Phe  Asn  Lys  Ile  Val  Asn  Phe  Phe  Asp  Gln  Lys  Pro  Glu  Glu
               1445                    1450                    1455 ttg  cat  aac  ttt  tcc  tta  aat  tct  gaa  tta  cat  tct  gac  ata  aga  aag        4612
Leu  His  Asn  Phe  Ser  Leu  Asn  Ser  Glu  Leu  His  Ser  Asp  Ile  Arg  Lys
               1460                    1465                    1470 aac  aaa  atg  gac  att  cta  agt  tat  gag  gaa  aca  gac  ata  gtt  aaa  cac        4660
Asn  Lys  Met  Asp  Ile  Leu  Ser  Tyr  Glu  Glu  Thr  Asp  Ile  Val  Lys  His
               1475                    1480                    1485 aaa  ata  ctg  aaa  gaa  agt  gtc  cca  gtt  ggt  act  gga  aat  caa  cta  gtg        4708
Lys  Ile  Leu  Lys  Glu  Ser  Val  Pro  Val  Gly  Thr  Gly  Asn  Gln  Leu  Val
               1490                    1495                    1500 acc  ttc  cag  gga  caa  ccc  gaa  cgt  gat  gaa  aag  atc  aaa  gaa  cct  act        4756
Thr  Phe  Gln  Gly  Gln  Pro  Glu  Arg  Asp  Glu  Lys  Ile  Lys  Glu  Pro  Thr
1505                    1510                    1515                    1520 ctg  ttg  ggt  ttt  cat  aca  gct  agc  gga  aaa  aaa  gtt  aaa  att  gca  aag        4804
Leu  Leu  Gly  Phe  His  Thr  Ala  Ser  Gly  Lys  Lys  Val  Lys  Ile  Ala  Lys
               1525                    1530                    1535 gaa  tct  ttg  gac  aaa  gtg  aaa  aac  ctt  ttt  gat  gaa  aaa  gag  caa  ggt        4852
Glu  Ser  Leu  Asp  Lys  Val  Lys  Asn  Leu  Phe  Asp  Glu  Lys  Glu  Gln  Gly
               1540                    1545                    1550 act  agt  gaa  atc  acc  agt  ttt  agc  cat  caa  tgg  gca  aag  acc  cta  aag        4900
Thr  Ser  Glu  Ile  Thr  Ser  Phe  Ser  His  Gln  Trp  Ala  Lys  Thr  Leu  Lys
               1555                    1560                    1565 tac  aga  gag  gcc  tgt  aaa  gac  ctt  gaa  tta  gca  tgt  gag  acc  att  gag        4948
Tyr  Arg  Glu  Ala  Cys  Lys  Asp  Leu  Glu  Leu  Ala  Cys  Glu  Thr  Ile  Glu
               1570                    1575                    1580 atc  aca  gct  gcc  cca  aag  tgt  aaa  gaa  atg  cag  aat  tct  ctc  aat  aat        4996
Ile  Thr  Ala  Ala  Pro  Lys  Cys  Lys  Glu  Met  Gln  Asn  Ser  Leu  Asn  Asn
1585                    1590                    1595                    1600 gat  aaa  aac  ctt  gtt  tct  att  gag  act  gtg  gtg  cca  cct  aag  ctc  tta        5044
Asp  Lys  Asn  Leu  Val  Ser  Ile  Glu  Thr  Val  Val  Pro  Pro  Lys  Leu  Leu
               1605                    1610                    1615 agt  gat  aat  tta  tgt  aga  caa  act  gaa  aat  ctc  aaa  aca  tca  aaa  agt        5092
Ser  Asp  Asn  Leu  Cys  Arg  Gln  Thr  Glu  Asn  Leu  Lys  Thr  Ser  Lys  Ser
               1620                    1625                    1630 atc  ttt  ttg  aaa  gtt  aaa  gta  cat  gaa  aat  gta  gaa  aaa  gaa  aca  gca        5140
Ile  Phe  Leu  Lys  Val  Lys  Val  His  Glu  Asn  Val  Glu  Lys  Glu  Thr  Ala
               1635                    1640                    1645 aaa  agt  cct  gca  act  tgt  tac  aca  aat  cag  tcc  cct  tat  tca  gtc  att        5188
Lys  Ser  Pro  Ala  Thr  Cys  Tyr  Thr  Asn  Gln  Ser  Pro  Tyr  Ser  Val  Ile
               1650                    1655                    1660 gaa  aat  tca  gcc  tta  gct  ttt  tac  aca  agt  tgt  agt  aga  aaa  act  tct        5236
Glu  Asn  Ser  Ala  Leu  Ala  Phe  Tyr  Thr  Ser  Cys  Ser  Arg  Lys  Thr  Ser
1665                    1670                    1675                    1680 gtg  agt  cag  act  tca  tta  ctt  gaa  gca  aaa  aaa  tgg  ctt  aga  gaa  gga        5284
Val  Ser  Gln  Thr  Ser  Leu  Leu  Glu  Ala  Lys  Lys  Trp  Leu  Arg  Glu  Gly
               1685                    1690                    1695 ata  ttt  gat  ggt  caa  cca  gaa  aga  ata  aat  act  gca  gat  tat  gta  gga        5332
Ile  Phe  Asp  Gly  Gln  Pro  Glu  Arg  Ile  Asn  Thr  Ala  Asp  Tyr  Val  Gly
               1700                    1705                    1710 aat  tat  ttg  tat  gaa  aat  aat  tca  aac  agt  act  ata  gct  gaa  aat  gac        5380
Asn  Tyr  Leu  Tyr  Glu  Asn  Asn  Ser  Asn  Ser  Thr  Ile  Ala  Glu  Asn  Asp
               1715                    1720                    1725 aaa  aat  cat  ctc  tcc  gaa  aaa  caa  gat  act  tat  tta  agt  aac  agt  agc        5428
Lys  Asn  His  Leu  Ser  Glu  Lys  Gln  Asp  Thr  Tyr  Leu  Ser  Asn  Ser  Ser
               1730                    1735                    1740 atg  tct  aac  agc  tat  tcc  tac  cat  tct  gat  gag  gta  tat  aat  gat  tca        5476
Met  Ser  Asn  Ser  Tyr  Ser  Tyr  His  Ser  Asp  Glu  Val  Tyr  Asn  Asp  Ser
1745                    1750                    1755                    1760
```

```
gga  tat  ctc  tca  aaa  aat  aaa  ctt  gat  tct  ggt  att  gag  cca  gta  ttg    5524
Gly  Tyr  Leu  Ser  Lys  Asn  Lys  Leu  Asp  Ser  Gly  Ile  Glu  Pro  Val  Leu
              1765               1770                    1775 aag  aat  gtt  gaa  gat  caa  aaa  aac  act  agt  ttt  tcc  aaa  gta  ata  tcc    5572
Lys  Asn  Val  Glu  Asp  Gln  Lys  Asn  Thr  Ser  Phe  Ser  Lys  Val  Ile  Ser
         1780                    1785                    1790 aat  gta  aaa  gat  gca  aat  gca  tac  cca  caa  act  gta  aat  gaa  gat  att    5620
Asn  Val  Lys  Asp  Ala  Asn  Ala  Tyr  Pro  Gln  Thr  Val  Asn  Glu  Asp  Ile
    1795                    1800                    1805 tgc  gtt  gag  gaa  ctt  gtg  act  agc  tct  tca  ccc  tgc  aaa  aat  aaa  aat    5668
Cys  Val  Glu  Glu  Leu  Val  Thr  Ser  Ser  Ser  Pro  Cys  Lys  Asn  Lys  Asn
1810                    1815                    1820 gca  gcc  att  aaa  ttg  tcc  ata  tct  aat  agt  aat  aat  ttt  gag  gta  ggg    5716
Ala  Ala  Ile  Lys  Leu  Ser  Ile  Ser  Asn  Ser  Asn  Asn  Phe  Glu  Val  Gly
1825                    1830                    1835                    1840 cca  cct  gca  ttt  agg  ata  gcc  agt  ggt  aaa  atc  cgt  ttg  tgt  tca  cat    5764
Pro  Pro  Ala  Phe  Arg  Ile  Ala  Ser  Gly  Lys  Ile  Arg  Leu  Cys  Ser  His
              1845                    1850                    1855 gaa  aca  att  aaa  aaa  gtg  aaa  gac  ata  ttt  aca  gac  agt  ttc  agc  aaa    5812
Glu  Thr  Ile  Lys  Lys  Val  Lys  Asp  Ile  Phe  Thr  Asp  Ser  Phe  Ser  Lys
         1860                    1865                    1870 gta  att  aag  gaa  aac  aac  gag  aat  aaa  tca  aaa  att  tgc  caa  acg  aaa    5860
Val  Ile  Lys  Glu  Asn  Asn  Glu  Asn  Lys  Ser  Lys  Ile  Cys  Gln  Thr  Lys
    1875                    1880                    1885 att  atg  gca  ggt  tgt  tac  gag  gca  ttg  gat  gat  tca  gag  gat  att  ctt    5908
Ile  Met  Ala  Gly  Cys  Tyr  Glu  Ala  Leu  Asp  Asp  Ser  Glu  Asp  Ile  Leu
1890                    1895                    1900 cat  aac  tct  cta  gat  aat  gat  gaa  tgt  agc  atg  cat  tca  cat  aag  gtt    5956
His  Asn  Ser  Leu  Asp  Asn  Asp  Glu  Cys  Ser  Met  His  Ser  His  Lys  Val
1905                    1910                    1915                    1920 ttt  gct  gac  att  cag  agt  gaa  gaa  att  tta  caa  cat  aac  caa  aat  atg    6004
Phe  Ala  Asp  Ile  Gln  Ser  Glu  Glu  Ile  Leu  Gln  His  Asn  Gln  Asn  Met
              1925                    1930                    1935 tct  gga  ttg  gag  aaa  gtt  tct  aaa  ata  tca  cct  tgt  gat  gtt  agt  ttg    6052
Ser  Gly  Leu  Glu  Lys  Val  Ser  Lys  Ile  Ser  Pro  Cys  Asp  Val  Ser  Leu
         1940                    1945                    1950 gaa  act  tca  gat  ata  tgt  aaa  tgt  agt  ata  ggg  aag  ctt  cat  aag  tca    6100
Glu  Thr  Ser  Asp  Ile  Cys  Lys  Cys  Ser  Ile  Gly  Lys  Leu  His  Lys  Ser
    1955                    1960                    1965 gtc  tca  tct  gca  aat  act  tgt  ggg  att  ttt  agc  aca  gca  agt  gga  aaa    6148
Val  Ser  Ser  Ala  Asn  Thr  Cys  Gly  Ile  Phe  Ser  Thr  Ala  Ser  Gly  Lys
1970                    1975                    1980 tct  gtc  cag  gta  tca  gat  gct  tca  tta  caa  aac  gca  aga  caa  gtg  ttt    6196
Ser  Val  Gln  Val  Ser  Asp  Ala  Ser  Leu  Gln  Asn  Ala  Arg  Gln  Val  Phe
1985                    1990                    1995                    2000 tct  gaa  ata  gaa  gat  agt  acc  aag  caa  gtc  ttt  tcc  aaa  gta  ttg  ttt    6244
Ser  Glu  Ile  Glu  Asp  Ser  Thr  Lys  Gln  Val  Phe  Ser  Lys  Val  Leu  Phe
              2005                    2010                    2015 aaa  agt  aac  gaa  cat  tca  gac  cag  ctc  aca  aga  gaa  gaa  aat  act  gct    6292
Lys  Ser  Asn  Glu  His  Ser  Asp  Gln  Leu  Thr  Arg  Glu  Glu  Asn  Thr  Ala
         2020                    2025                    2030 ata  cgt  act  cca  gaa  cat  tta  ata  tcc  caa  aaa  ggc  ttt  tca  tat  aat    6340
Ile  Arg  Thr  Pro  Glu  His  Leu  Ile  Ser  Gln  Lys  Gly  Phe  Ser  Tyr  Asn
    2035                    2040                    2045 gtg  gta  aat  tca  tct  gct  ttc  tct  gga  ttt  agt  aca  gca  agt  gga  aag    6388
Val  Val  Asn  Ser  Ser  Ala  Phe  Ser  Gly  Phe  Ser  Thr  Ala  Ser  Gly  Lys
2050                    2055                    2060 caa  gtt  tcc  att  tta  gaa  agt  tcc  tta  cac  aaa  gtt  aag  gga  gtg  tta    6436
Gln  Val  Ser  Ile  Leu  Glu  Ser  Ser  Leu  His  Lys  Val  Lys  Gly  Val  Leu
2065                    2070                    2075                    2080
```

```
gag gaa ttt gat tta atc aga act gag cat agt ctt cac tat tca cct     6484
Glu Glu Phe Asp Leu Ile Arg Thr Glu His Ser Leu His Tyr Ser Pro
        2085                2090                2095 acg tct aga caa aat gta tca aaa ata ctt cct cgt gtt gat aag aga     6532
Thr Ser Arg Gln Asn Val Ser Lys Ile Leu Pro Arg Val Asp Lys Arg
    2100                2105                2110 aac cca gag cac tgt gta aac tca gaa atg gaa aaa acc tgc agt aaa     6580
Asn Pro Glu His Cys Val Asn Ser Glu Met Glu Lys Thr Cys Ser Lys
            2115                2120                2125 gaa ttt aaa tta tca aat aac tta aat gtt gaa ggt ggt tct tca gaa     6628
Glu Phe Lys Leu Ser Asn Asn Leu Asn Val Glu Gly Gly Ser Ser Glu
        2130                2135                2140 aat aat cac tct att aaa gtt tct cca tat ctc tct caa ttt caa caa     6676
Asn Asn His Ser Ile Lys Val Ser Pro Tyr Leu Ser Gln Phe Gln Gln
2145                2150                2155                2160 gac aaa caa cag ttg gta tta gga acc aaa gtc tca ctt gtt gag aac     6724
Asp Lys Gln Gln Leu Val Leu Gly Thr Lys Val Ser Leu Val Glu Asn
            2165                2170                2175 att cat gtt ttg gga aaa gaa cag gct tca cct aaa aac gta aaa atg     6772
Ile His Val Leu Gly Lys Glu Gln Ala Ser Pro Lys Asn Val Lys Met
        2180                2185                2190 gaa att ggt aaa act gaa act ttt tct gat gtt cct gtg aaa aca aat     6820
Glu Ile Gly Lys Thr Glu Thr Phe Ser Asp Val Pro Val Lys Thr Asn
    2195                2200                2205 ata gaa gtt tgt tct act tac tcc aaa gat tca gaa aac tac ttt gaa     6868
Ile Glu Val Cys Ser Thr Tyr Ser Lys Asp Ser Glu Asn Tyr Phe Glu
        2210                2215                2220 aca gaa gca gta gaa att gct aaa gct ttt atg gaa gat gat gaa ctg     6916
Thr Glu Ala Val Glu Ile Ala Lys Ala Phe Met Glu Asp Asp Glu Leu
2225                2230                2235                2240 aca gat tct aaa ctg cca agt cat gcc aca cat tct ctt ttt aca tgt     6964
Thr Asp Ser Lys Leu Pro Ser His Ala Thr His Ser Leu Phe Thr Cys
            2245                2250                2255 ccc gaa aat gag gaa atg gtt ttg tca aat tca aga att gga aaa aga     7012
Pro Glu Asn Glu Glu Met Val Leu Ser Asn Ser Arg Ile Gly Lys Arg
        2260                2265                2270 aga gga gag ccc ctt atc tta gtg gga gaa ccc tca atc aaa aga aac     7060
Arg Gly Glu Pro Leu Ile Leu Val Gly Glu Pro Ser Ile Lys Arg Asn
    2275                2280                2285 tta tta aat gaa ttt gac agg ata ata gaa aat caa gaa aaa tcc tta     7108
Leu Leu Asn Glu Phe Asp Arg Ile Ile Glu Asn Gln Glu Lys Ser Leu
        2290                2295                2300 aag gct tca aaa agc act cca gat ggc aca ata aaa gat cga aga ttg     7156
Lys Ala Ser Lys Ser Thr Pro Asp Gly Thr Ile Lys Asp Arg Arg Leu
2305                2310                2315                2320 ttt atg cat cat gtt tct tta gag ccg att acc tgt gta ccc ttt cgc     7204
Phe Met His His Val Ser Leu Glu Pro Ile Thr Cys Val Pro Phe Arg
            2325                2330                2335 aca act aag gaa cgt caa gag ata cag aat cca aat ttt acc gca cct     7252
Thr Thr Lys Glu Arg Gln Glu Ile Gln Asn Pro Asn Phe Thr Ala Pro
        2340                2345                2350 ggt caa gaa ttt ctg tct aaa tct cat ttg tat gaa cat ctg act ttg     7300
Gly Gln Glu Phe Leu Ser Lys Ser His Leu Tyr Glu His Leu Thr Leu
    2355                2360                2365 gaa aaa tct tca agc aat tta gca gtt tca gga cat cca ttt tat caa     7348
Glu Lys Ser Ser Ser Asn Leu Ala Val Ser Gly His Pro Phe Tyr Gln
        2370                2375                2380 gtt tct gct aca aga aat gaa aaa atg aga cac ttg att act aca ggc     7396
Val Ser Ala Thr Arg Asn Glu Lys Met Arg His Leu Ile Thr Thr Gly
2385                2390                2395                2400
```

```
aga  cca  acc  aaa  gtc  ttt  gtt  cca  cct  ttt  aaa  act  aaa  tca  cat  ttt       7444
Arg  Pro  Thr  Lys  Val  Phe  Val  Pro  Pro  Phe  Lys  Thr  Lys  Ser  His  Phe
                    2405                    2410                    2415 cac  aga  gtt  gaa  cag  tgt  gtt  agg  aat  att  aac  ttg  gag  gaa  aac  aga       7492
His  Arg  Val  Glu  Gln  Cys  Val  Arg  Asn  Ile  Asn  Leu  Glu  Glu  Asn  Arg
               2420                    2425                    2430 caa  aag  caa  aac  att  gat  gga  cat  ggc  tct  gat  gat  agt  aaa  aat  aag       7540
Gln  Lys  Gln  Asn  Ile  Asp  Gly  His  Gly  Ser  Asp  Asp  Ser  Lys  Asn  Lys
               2435                    2440                    2445 att  aat  gac  aat  gag  att  cat  cag  ttt  aac  aaa  aac  aac  tcc  aat  caa       7588
Ile  Asn  Asp  Asn  Glu  Ile  His  Gln  Phe  Asn  Lys  Asn  Asn  Ser  Asn  Gln
               2450                    2455                    2460 gca  gca  gct  gta  act  ttc  aca  aag  tgt  gaa  gaa  gaa  cct  tta  gat  tta       7636
Ala  Ala  Ala  Val  Thr  Phe  Thr  Lys  Cys  Glu  Glu  Glu  Pro  Leu  Asp  Leu
2465                     2470                    2475                    2480 att  aca  agt  ctt  cag  aat  gcc  aga  gat  ata  cag  gat  atg  cga  att  aag       7684
Ile  Thr  Ser  Leu  Gln  Asn  Ala  Arg  Asp  Ile  Gln  Asp  Met  Arg  Ile  Lys
                    2485                    2490                    2495 aag  aaa  caa  agg  caa  cgc  gtc  ttt  cca  cag  cca  ggc  agt  ctg  tat  ctt       7732
Lys  Lys  Gln  Arg  Gln  Arg  Val  Phe  Pro  Gln  Pro  Gly  Ser  Leu  Tyr  Leu
               2500                    2505                    2510 gca  aaa  aca  tcc  act  ctg  cct  cga  atc  tct  ctg  aaa  gca  gca  gta  gga       7780
Ala  Lys  Thr  Ser  Thr  Leu  Pro  Arg  Ile  Ser  Leu  Lys  Ala  Ala  Val  Gly
               2515                    2520                    2525 ggc  caa  gtt  ccc  tct  gcg  tgt  tct  cat  aaa  cag  ctg  tat  acg  tat  ggc       7828
Gly  Gln  Val  Pro  Ser  Ala  Cys  Ser  His  Lys  Gln  Leu  Tyr  Thr  Tyr  Gly
               2530                    2535                    2540 gtt  tct  aaa  cat  tgc  ata  aaa  att  aac  agc  aaa  aat  gca  gag  tct  ttt       7876
Val  Ser  Lys  His  Cys  Ile  Lys  Ile  Asn  Ser  Lys  Asn  Ala  Glu  Ser  Phe
2545                     2550                    2555                    2560 cag  ttt  cac  act  gaa  gat  tat  ttt  ggt  aag  gaa  agt  tta  tgg  act  gga       7924
Gln  Phe  His  Thr  Glu  Asp  Tyr  Phe  Gly  Lys  Glu  Ser  Leu  Trp  Thr  Gly
                    2565                    2570                    2575 aaa  gga  ata  cag  ttg  gct  gat  ggt  gga  tgg  ctc  ata  ccc  tcc  aat  gat       7972
Lys  Gly  Ile  Gln  Leu  Ala  Asp  Gly  Gly  Trp  Leu  Ile  Pro  Ser  Asn  Asp
               2580                    2585                    2590 gga  aag  gct  gga  aaa  gaa  gaa  ttt  tat  agg  gct  ctg  tgt  gac  act  cca       8020
Gly  Lys  Ala  Gly  Lys  Glu  Glu  Phe  Tyr  Arg  Ala  Leu  Cys  Asp  Thr  Pro
               2595                    2600                    2605 ggt  gtg  gat  cca  aag  ctt  att  tct  aga  att  tgg  gtt  tat  aat  cac  tat       8068
Gly  Val  Asp  Pro  Lys  Leu  Ile  Ser  Arg  Ile  Trp  Val  Tyr  Asn  His  Tyr
               2610                    2615                    2620 aga  tgg  atc  ata  tgg  aaa  ctg  gca  gct  atg  gaa  tgt  gcc  ttt  cct  aag       8116
Arg  Trp  Ile  Ile  Trp  Lys  Leu  Ala  Ala  Met  Glu  Cys  Ala  Phe  Pro  Lys
2625                     2630                    2635                    2640 gaa  ttt  gct  aat  aga  tgc  cta  agc  cca  gaa  agg  gtg  ctt  ctt  caa  cta       8164
Glu  Phe  Ala  Asn  Arg  Cys  Leu  Ser  Pro  Glu  Arg  Val  Leu  Leu  Gln  Leu
               2645                    2650                    2655 aaa  tac  aga  tat  gat  acg  gaa  att  gat  aga  agc  aga  aga  tcg  gct  ata       8212
Lys  Tyr  Arg  Tyr  Asp  Thr  Glu  Ile  Asp  Arg  Ser  Arg  Arg  Ser  Ala  Ile
               2660                    2665                    2670 aaa  aag  ata  atg  gaa  agg  gat  gac  aca  gct  gca  aaa  aca  ctt  gtt  ctc       8260
Lys  Lys  Ile  Met  Glu  Arg  Asp  Asp  Thr  Ala  Ala  Lys  Thr  Leu  Val  Leu
               2675                    2680                    2685 tgt  gtt  tct  gac  ata  att  tca  ttg  agc  gca  aat  ata  tct  gaa  act  tct       8308
Cys  Val  Ser  Asp  Ile  Ile  Ser  Leu  Ser  Ala  Asn  Ile  Ser  Glu  Thr  Ser
               2690                    2695                    2700 agc  aat  aaa  act  agt  agt  gca  gat  acc  caa  aaa  gtg  gcc  att  att  gaa       8356
Ser  Asn  Lys  Thr  Ser  Ser  Ala  Asp  Thr  Gln  Lys  Val  Ala  Ile  Ile  Glu
2705                     2710                    2715                    2720
```

```
ctt  aca  gat  ggg  tgg  tat  gct  gtt  aag  gcc  cag  tta  gat  cct  ccc  ctc        8404
Leu  Thr  Asp  Gly  Trp  Tyr  Ala  Val  Lys  Ala  Gln  Leu  Asp  Pro  Pro  Leu
              2725                    2730                    2735 tta  gct  gtc  tta  aag  aat  ggc  aga  ctg  aca  gtt  ggt  cag  aag  att  att        8452
Leu  Ala  Val  Leu  Lys  Asn  Gly  Arg  Leu  Thr  Val  Gly  Gln  Lys  Ile  Ile
         2740                    2745                    2750 ctt  cat  gga  gca  gaa  ctg  gtg  ggc  tct  cct  gat  gcc  tgt  aca  cct  ctt        8500
Leu  His  Gly  Ala  Glu  Leu  Val  Gly  Ser  Pro  Asp  Ala  Cys  Thr  Pro  Leu
         2755                    2760                    2765 gaa  gcc  cca  gaa  tct  ctt  atg  tta  aag  att  tct  gct  aac  agt  act  cgg        8548
Glu  Ala  Pro  Glu  Ser  Leu  Met  Leu  Lys  Ile  Ser  Ala  Asn  Ser  Thr  Arg
         2770                    2775                    2780 cct  gct  cgc  tgg  tat  acc  aaa  ctt  gga  ttc  ttt  cct  gac  cct  aga  cct        8596
Pro  Ala  Arg  Trp  Tyr  Thr  Lys  Leu  Gly  Phe  Phe  Pro  Asp  Pro  Arg  Pro
2785                    2790                    2795                    2800 ttt  cct  ctg  ccc  tta  tca  tcg  ctt  ttc  agt  gat  gga  gga  aat  gtt  ggt        8644
Phe  Pro  Leu  Pro  Leu  Ser  Ser  Leu  Phe  Ser  Asp  Gly  Gly  Asn  Val  Gly
                    2805                    2810                    2815 tgt  gtt  gat  gta  att  att  caa  aga  gca  tac  cct  ata  cag  cgg  atg  gag        8692
Cys  Val  Asp  Val  Ile  Ile  Gln  Arg  Ala  Tyr  Pro  Ile  Gln  Arg  Met  Glu
              2820                    2825                    2830 aag  aca  tca  tct  gga  tta  tac  ata  ttt  cgc  aat  gaa  aga  gag  gaa  gaa        8740
Lys  Thr  Ser  Ser  Gly  Leu  Tyr  Ile  Phe  Arg  Asn  Glu  Arg  Glu  Glu  Glu
         2835                    2840                    2845 aag  gaa  gca  gca  aaa  tat  gtg  gag  gcc  caa  caa  aag  aga  cta  gaa  gcc        8788
Lys  Glu  Ala  Ala  Lys  Tyr  Val  Glu  Ala  Gln  Gln  Lys  Arg  Leu  Glu  Ala
         2850                    2855                    2860 tta  ttc  act  aaa  att  cag  gag  gaa  ttt  gaa  gaa  cat  gaa  gaa  aac  aca        8836
Leu  Phe  Thr  Lys  Ile  Gln  Glu  Glu  Phe  Glu  Glu  His  Glu  Glu  Asn  Thr
2865                    2870                    2875                    2880 aca  aaa  cca  tat  tta  cca  tca  cgt  gca  cta  aca  aga  cag  caa  gtt  cgt        8884
Thr  Lys  Pro  Tyr  Leu  Pro  Ser  Arg  Ala  Leu  Thr  Arg  Gln  Gln  Val  Arg
                    2885                    2890                    2895 gct  ttg  caa  gat  ggt  gca  gag  ctt  tat  gaa  gca  gtg  aag  aat  gca  gca        8932
Ala  Leu  Gln  Asp  Gly  Ala  Glu  Leu  Tyr  Glu  Ala  Val  Lys  Asn  Ala  Ala
         2900                    2905                    2910 gac  cca  gct  tac  ctt  gag  ggt  tat  ttc  agt  gaa  gag  cag  tta  aga  gcc        8980
Asp  Pro  Ala  Tyr  Leu  Glu  Gly  Tyr  Phe  Ser  Glu  Glu  Gln  Leu  Arg  Ala
         2915                    2920                    2925 ttg  aat  aat  cac  agg  caa  atg  ttg  aat  gat  aag  aaa  caa  gct  cag  atc        9028
Leu  Asn  Asn  His  Arg  Gln  Met  Leu  Asn  Asp  Lys  Lys  Gln  Ala  Gln  Ile
2930                    2935                    2940 cag  ttg  gaa  att  agg  aag  gcc  atg  gaa  tct  gct  gaa  caa  aag  gaa  caa        9076
Gln  Leu  Glu  Ile  Arg  Lys  Ala  Met  Glu  Ser  Ala  Glu  Gln  Lys  Glu  Gln
2945                    2950                    2955                    2960 ggt  tta  tca  agg  gat  gtc  aca  acc  gtg  tgg  aag  ttg  cgt  att  gta  agc        9124
Gly  Leu  Ser  Arg  Asp  Val  Thr  Thr  Val  Trp  Lys  Leu  Arg  Ile  Val  Ser
              2965                    2970                    2975 tat  tca  aaa  aaa  gaa  aaa  gat  tca  gtt  ata  ctg  agt  att  tgg  cgt  cca        9172
Tyr  Ser  Lys  Lys  Glu  Lys  Asp  Ser  Val  Ile  Leu  Ser  Ile  Trp  Arg  Pro
         2980                    2985                    2990 tca  tca  gat  tta  tat  tct  ctg  tta  aca  gaa  gga  aag  aga  tac  aga  att        9220
Ser  Ser  Asp  Leu  Tyr  Ser  Leu  Leu  Thr  Glu  Gly  Lys  Arg  Tyr  Arg  Ile
         2995                    3000                    3005 tat  cat  ctt  gca  act  tca  aaa  tct  aaa  agt  aaa  tct  gaa  aga  gct  aac        9268
Tyr  His  Leu  Ala  Thr  Ser  Lys  Ser  Lys  Ser  Lys  Ser  Glu  Arg  Ala  Asn
         3010                    3015                    3020 ata  cag  tta  gca  gcg  aca  aaa  aaa  act  cag  tat  caa  caa  cta  ccg  gtt        9316
Ile  Gln  Leu  Ala  Ala  Thr  Lys  Lys  Thr  Gln  Tyr  Gln  Gln  Leu  Pro  Val
         3025                    3030                    3035                    3040
```

```
tca  gat  gaa  att  tta  ttt  cag  att  tac  cag  cca  cgg  gag  ccc  ctt  cac              9364
Ser  Asp  Glu  Ile  Leu  Phe  Gln  Ile  Tyr  Gln  Pro  Arg  Glu  Pro  Leu  His
               3045                    3050                    3055 ttc  agc  aaa  ttt  tta  gat  cca  gac  ttt  cag  cca  tct  tgt  tct  gag  gtg              9412
Phe  Ser  Lys  Phe  Leu  Asp  Pro  Asp  Phe  Gln  Pro  Ser  Cys  Ser  Glu  Val
               3060                    3065                    3070 gac  cta  ata  gga  ttt  gtc  gtt  tct  gtt  gtg  aaa  aaa  aca  gga  ctt  gcc              9460
Asp  Leu  Ile  Gly  Phe  Val  Val  Ser  Val  Val  Lys  Lys  Thr  Gly  Leu  Ala
               3075                    3080                    3085 cct  ttc  gtc  tat  ttg  tca  gac  gaa  tgt  tac  aat  tta  ctg  gca  ata  aag              9508
Pro  Phe  Val  Tyr  Leu  Ser  Asp  Glu  Cys  Tyr  Asn  Leu  Leu  Ala  Ile  Lys
               3090                    3095                    3100 ttt  tgg  ata  gac  ctt  aat  gag  gac  att  att  aag  cct  cat  atg  tta  att              9556
Phe  Trp  Ile  Asp  Leu  Asn  Glu  Asp  Ile  Ile  Lys  Pro  His  Met  Leu  Ile
3105                3110                     3115                    3120 gct  gca  agc  aac  ctc  cag  tgg  cga  cca  gaa  tcc  aaa  tca  ggc  ctt  ctt              9604
Ala  Ala  Ser  Asn  Leu  Gln  Trp  Arg  Pro  Glu  Ser  Lys  Ser  Gly  Leu  Leu
               3125                    3130                    3135 act  tta  ttt  gct  gga  gat  ttt  tct  gtg  ttt  tct  gct  agt  cca  aaa  gag              9652
Thr  Leu  Phe  Ala  Gly  Asp  Phe  Ser  Val  Phe  Ser  Ala  Ser  Pro  Lys  Glu
               3140                    3145                    3150 ggc  cac  ttt  caa  gag  aca  ttc  aac  aaa  atg  aaa  aat  act  gtt  gag  aat              9700
Gly  His  Phe  Gln  Glu  Thr  Phe  Asn  Lys  Met  Lys  Asn  Thr  Val  Glu  Asn
               3155                    3160                    3165 att  gac  ata  ctt  tgc  aat  gaa  gca  gaa  aac  aag  ctt  atg  cat  ata  ctg              9748
Ile  Asp  Ile  Leu  Cys  Asn  Glu  Ala  Glu  Asn  Lys  Leu  Met  His  Ile  Leu
               3170                    3175                    3180 cat  gca  aat  gat  ccc  aag  tgg  tcc  acc  cca  act  aaa  gac  tgt  act  tca              9796
His  Ala  Asn  Asp  Pro  Lys  Trp  Ser  Thr  Pro  Thr  Lys  Asp  Cys  Thr  Ser
3185                3190                    3195                     3200 ggg  ccg  tac  act  gct  caa  atc  att  cct  ggt  aca  gga  aac  aag  ctt  ctg              9844
Gly  Pro  Tyr  Thr  Ala  Gln  Ile  Ile  Pro  Gly  Thr  Gly  Asn  Lys  Leu  Leu
               3205                    3210                    3215 atg  tct  tct  cct  aat  tgt  gag  ata  tat  tat  caa  agt  cct  tta  tca  ctt              9892
Met  Ser  Ser  Pro  Asn  Cys  Glu  Ile  Tyr  Tyr  Gln  Ser  Pro  Leu  Ser  Leu
               3220                    3225                    3230 tgt  atg  gcc  aaa  agg  aag  tct  gtt  tcc  aca  cct  gtc  tca  gcc  cag  atg              9940
Cys  Met  Ala  Lys  Arg  Lys  Ser  Val  Ser  Thr  Pro  Val  Ser  Ala  Gln  Met
               3235                    3240                    3245 act  tca  aag  tct  tgt  aaa  ggg  gag  aaa  gag  att  gat  gac  caa  aag  aac              9988
Thr  Ser  Lys  Ser  Cys  Lys  Gly  Glu  Lys  Glu  Ile  Asp  Asp  Gln  Lys  Asn
               3250                    3255                    3260 tgc  aaa  aag  aga  aga  gcc  ttg  gat  ttc  ttg  agt  aga  ctg  cct  tta  cct              10036
Cys  Lys  Lys  Arg  Arg  Ala  Leu  Asp  Phe  Leu  Ser  Arg  Leu  Pro  Leu  Pro
3265                3270                    3275                     3280 cca  cct  gtt  agt  ccc  att  tgt  aca  ttt  gtt  tct  ccg  gct  gca  cag  aag              10084
Pro  Pro  Val  Ser  Pro  Ile  Cys  Thr  Phe  Val  Ser  Pro  Ala  Ala  Gln  Lys
               3285                    3290                    3295 gca  ttt  cag  cca  cca  agg  agt  tgt  ggc  acc  aaa  tac  gaa  aca  ccc  ata              10132
Ala  Phe  Gln  Pro  Pro  Arg  Ser  Cys  Gly  Thr  Lys  Tyr  Glu  Thr  Pro  Ile
               3300                    3305                    3310 aag  aaa  aaa  gaa  ctg  aat  tct  cct  cag  atg  act  cca  ttt  aaa  aaa  ttc              10180
Lys  Lys  Lys  Glu  Leu  Asn  Ser  Pro  Gln  Met  Thr  Pro  Phe  Lys  Lys  Phe
               3315                    3320                    3325 aat  gaa  att  tct  ctt  ttg  gaa  agt  aat  tca  ata  gct  gac  gaa  gaa  ctt              10228
Asn  Glu  Ile  Ser  Leu  Leu  Glu  Ser  Asn  Ser  Ile  Ala  Asp  Glu  Glu  Leu
               3330                    3335                    3340 gca  ttg  ata  aat  acc  caa  gct  ctt  ttg  tct  ggt  tca  aca  gga  gaa  aaa              10276
Ala  Leu  Ile  Asn  Thr  Gln  Ala  Leu  Leu  Ser  Gly  Ser  Thr  Gly  Glu  Lys
3345                3350                    3355                     3360
```

```
caa  ttt  ata  tct  gtc  agt  gaa  tcc  act  agg  act  gct  ccc  acc  agt  tca       10324
Gln  Phe  Ile  Ser  Val  Ser  Glu  Ser  Thr  Arg  Thr  Ala  Pro  Thr  Ser  Ser
                    3365                3370                     3375 gaa  gat  tat  ctc  aga  ctg  aaa  cga  cgt  tgt  act  aca  tct  ctg  atc  aaa       10372
Glu  Asp  Tyr  Leu  Arg  Leu  Lys  Arg  Arg  Cys  Thr  Thr  Ser  Leu  Ile  Lys
                    3380                3385                     3390 gaa  cag  gag  agt  tcc  cag  gcc  agt  acg  gaa  gaa  tgt  gag  aaa  aat  aag       10420
Glu  Gln  Glu  Ser  Ser  Gln  Ala  Ser  Thr  Glu  Glu  Cys  Glu  Lys  Asn  Lys
                    3395                3400                     3405 cag  gac  aca  att  aca  act  aaa  aaa  tat  atc  taagcatttg  caaaggcgac             10470
Gln  Asp  Thr  Ile  Thr  Thr  Lys  Lys  Tyr  Ile
                    3410                3415 aataaattat  tgacgcttaa  cctttccagt  ttataagact  ggaatataat  ttcaaaccac                10530
acattagtac  ttatgttgcm  caatgagaaa  agaaattagt  ttcaaattta  cctcagcgtt                10590
tgtgtatcgg  gcaaaaatcg  ttttgcccga  ttccgtattg  gtatacttt   gcctcagttg                10650 catatcctaa  aactaaatgt  aatttattaa  ctaatcaaga  aaaacatctt  tggctgagct                10710
cggtggctca  tgcctgtaat  cccaacactt  tgagaagctg  aggtgggagg  agtgcttgag                10770
gccaggagtt  caagaccagc  ctgggcaaca  tagggagacc  ccatctttac  gaagaaaaaa                10830 aaaaggga   aaagaaaatc  ttttaaatct  ttggatttca  ctacaagtat  tattttacaa                 10890
gtgaaataaa  cataccattt  tcttttagat  tgtgtcatta  aatggaatga  ggtctcttag                10950
tacagttatt  ttgatgcaga  taattccttt  tagtttagct  actatttag   gggatttttt                11010 ttagaggtaa  ctcactatga  aatagttccc  cttaatgcaa  atatgttggt  tctgcaatag                11070
ttccatcctg  ttcaaaartc  rggrtgaawa  tgaagagtgg  tgttyccttt  tgagcaattc                11130
tcatccttaa  gtcagcrtga  ttataagaaa  aatagaaccc  ycagtgtaac  yctaattcct                11190
ttttrctatt  ccagtgtgat  ctctgaaakt  aaattacttc  mactaaaaat  tcaaaaactt                11250
waamtcagaa  rawttcawag  twgatttatt  ttt                                               11283
```

(2) INFORMATION FOR SEQ ID NO:4:

(i) SEQUENCE CHARACTERISTICS:
        (A) LENGTH: 3418
        (B) TYPE: amino acid
        (C) STRANDEDNESS: single
        (D) TOPOLOGY: unknown (ii) MOLECULE TYPE: protein (iii) HYPOTHETICAL: no (iv) ANTI-SENSE: no (v) ORIGINAL SOURCE:
        (A) ORGANISM: Homo sapiens sapiens
        (C) INDIVIDUAL ISOLATE:
        (D) DEVELOPMENTAL STAGE: adult
        (F) TISSUE TYPE: female breast
        (G) CELL TYPE: normal breast tissue
        (H) CELL LINE: HMEC
        (I) ORGANELLE: no (ix) FEATURE:
        (A) NAME/KEY: BRCA2 protein
        (B) LOCATION: 1 to 3418; Genbank locus HSU43746
        (C) IDENTIFICATION METHOD:
        (D) OTHER INFORMATION: BRCA2 protein has a negative
            regulatory effect on growth of human mammary cells.

(x) PUBLICATION INFORMATION:
        (A) AUTHORS: Wooster, R. et al.
        (B) TITLE: Identification of the breast cancer
            susceptability gene BRCA2
        (C) JOURNAL: Nature (D) VOLUME: 379
(E) PAGES: 789-792
(F) DATE: 1995
(K) RELEVANT RESIDUES IN SEQ ID NO:4: granin box
    domain at amino acids 3334-3344

(xi) SEQUENCE DESCRIPTION: SEQ ID NO:4:

```
Met Pro Ile Gly Ser Lys Glu Arg Pro Thr Phe Phe Glu Ile Phe Lys
 1               5                  10                  15

Thr Arg Cys Asn Lys Ala Asp Leu Gly Pro Ile Ser Leu Asn Trp Phe
                 20                  25                  30

Glu Glu Leu Ser Ser Glu Ala Pro Pro Tyr Asn Ser Glu Pro Ala Glu
             35                  40                  45

Glu Ser Glu His Lys Asn Asn Asn Tyr Glu Pro Asn Leu Phe Lys Thr
         50                  55                  60

Pro Gln Arg Lys Pro Ser Tyr Asn Gln Leu Ala Ser Thr Pro Ile Ile
 65                  70                  75                  80

Phe Lys Glu Gln Gly Leu Thr Leu Pro Leu Tyr Gln Ser Pro Val Lys
                 85                  90                  95

Glu Leu Asp Lys Phe Lys Leu Asp Leu Gly Arg Asn Val Pro Asn Ser
             100                 105                 110

Arg His Lys Ser Leu Arg Thr Val Lys Tyr Lys Met Asp Gln Ala Asp
         115                 120                 125

Asp Val Ser Cys Pro Leu Leu Asn Ser Cys Leu Ser Glu Ser Pro Val
     130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                 165                 170                 175

Pro Lys His Ile Ser Glu Ser Leu Gly Ala Glu Val Asp Pro Asp Met
             180                 185                 190

Ser Trp Ser Ser Ser Leu Ala Thr Pro Pro Thr Leu Ser Ser Thr Val
         195                 200                 205

Leu Ile Val Arg Asn Glu Glu Ala Ser Glu Thr Val Phe Pro His Asp
     210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                 245                 250                 255

Asn Gln Arg Glu Ala Ala Ser His Gly Phe Gly Lys Thr Ser Gly Asn
             260                 265                 270

Ser Phe Lys Val Asn Ser Cys Lys Asp His Ile Gly Lys Ser Met Pro
         275                 280                 285

Asn Val Leu Glu Asp Glu Val Tyr Glu Thr Val Val Asp Thr Ser Glu
     290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                 325                 330                 335

Asn Ala Asp Glu Cys Glu Lys Ser Lys Asn Gln Val Lys Glu Lys Tyr
             340                 345                 350

Ser Phe Val Ser Glu Val Glu Pro Asn Asp Thr Asp Pro Leu Asp Ser
         355                 360                 365

Asn Val Ala His Gln Lys Pro Phe Glu Ser Gly Ser Asp Lys Ile Ser
     370                 375                 380
```

| | | | | | | | | | | | | | | | |
|---|---|---|---|---|---|---|---|---|---|---|---|---|---|---|---|
| Lys | Glu | Val | Val | Pro | Ser | Leu | Ala | Cys | Glu | Trp | Ser | Gln | Leu | Thr | Leu |
| 385 | | | | 390 | | | | | 395 | | | | | | 400 |
| Ser | Gly | Leu | Asn | Gly | Ala | Gln | Met | Glu | Lys | Ile | Pro | Leu | Leu | His | Ile |
| | | | | 405 | | | | | 410 | | | | | 415 | |
| Ser | Ser | Cys | Asp | Gln | Asn | Ile | Ser | Glu | Lys | Asp | Leu | Leu | Asp | Thr | Glu |
| | | | 420 | | | | | 425 | | | | | 430 | | |
| Asn | Lys | Arg | Lys | Lys | Asp | Phe | Leu | Thr | Ser | Glu | Asn | Ser | Leu | Pro | Arg |
| | | 435 | | | | | 440 | | | | | 445 | | | |
| Ile | Ser | Ser | Leu | Pro | Lys | Ser | Glu | Lys | Pro | Leu | Asn | Glu | Glu | Thr | Val |
| | 450 | | | | | 455 | | | | | 460 | | | | |
| Val | Asn | Lys | Arg | Asp | Glu | Glu | Gln | His | Leu | Glu | Ser | His | Thr | Asp | Cys |
| 465 | | | | | 470 | | | | | 475 | | | | | 480 |
| Ile | Leu | Ala | Val | Lys | Gln | Ala | Ile | Ser | Gly | Thr | Ser | Pro | Val | Ala | Ser |
| | | | | 485 | | | | | 490 | | | | | 495 | |
| Ser | Phe | Gln | Gly | Ile | Lys | Lys | Ser | Ile | Phe | Arg | Ile | Arg | Glu | Ser | Pro |
| | | | 500 | | | | | 505 | | | | | 510 | | |
| Lys | Glu | Thr | Phe | Asn | Ala | Ser | Phe | Ser | Gly | His | Met | Thr | Asp | Pro | Asn |
| | | | 515 | | | | | 520 | | | | | 525 | | |
| Phe | Lys | Lys | Glu | Thr | Glu | Ala | Ser | Glu | Ser | Gly | Leu | Glu | Ile | His | Thr |
| | | 530 | | | | | 535 | | | | | 540 | | | |
| Val | Cys | Ser | Gln | Lys | Glu | Asp | Ser | Leu | Cys | Pro | Asn | Leu | Ile | Asp | Asn |
| 545 | | | | | 550 | | | | | 555 | | | | | 560 |
| Gly | Ser | Trp | Pro | Ala | Thr | Thr | Thr | Gln | Asn | Ser | Val | Ala | Leu | Lys | Asn |
| | | | | 565 | | | | | 570 | | | | | 575 | |
| Ala | Gly | Leu | Ile | Ser | Thr | Leu | Lys | Lys | Lys | Thr | Asn | Lys | Phe | Ile | Tyr |
| | | | | 580 | | | | | 585 | | | | | 590 | |
| Ala | Ile | His | Asp | Glu | Thr | Phe | Tyr | Lys | Gly | Lys | Lys | Ile | Pro | Lys | Asp |
| | | | 595 | | | | | 600 | | | | | 605 | | |
| Gln | Lys | Ser | Glu | Leu | Ile | Asn | Cys | Ser | Ala | Gln | Phe | Glu | Ala | Asn | Ala |
| | | 610 | | | | | 615 | | | | | 620 | | | |
| Phe | Glu | Ala | Pro | Leu | Thr | Phe | Ala | Asn | Ala | Asp | Ser | Gly | Leu | Leu | His |
| 625 | | | | | 630 | | | | | 635 | | | | | 640 |
| Ser | Ser | Val | Lys | Arg | Ser | Cys | Ser | Gln | Asn | Asp | Ser | Glu | Glu | Pro | Thr |
| | | | | 645 | | | | | 650 | | | | | 655 | |
| Leu | Ser | Leu | Thr | Ser | Ser | Phe | Gly | Thr | Ile | Leu | Arg | Lys | Cys | Ser | Arg |
| | | | 660 | | | | | 665 | | | | | 670 | | |
| Asn | Glu | Thr | Cys | Ser | Asn | Asn | Thr | Val | Ile | Ser | Gln | Asp | Leu | Asp | Tyr |
| | | | 675 | | | | | 680 | | | | | 685 | | |
| Lys | Glu | Ala | Lys | Cys | Asn | Lys | Glu | Lys | Leu | Gln | Leu | Phe | Ile | Thr | Pro |
| | | 690 | | | | | 695 | | | | | 700 | | | |
| Glu | Ala | Asp | Ser | Leu | Ser | Cys | Leu | Gln | Glu | Gly | Gln | Cys | Glu | Asn | Asp |
| 705 | | | | | 710 | | | | | 715 | | | | | 720 |
| Pro | Lys | Ser | Lys | Lys | Val | Ser | Asp | Ile | Lys | Glu | Glu | Val | Leu | Ala | Ala |
| | | | | 725 | | | | | 730 | | | | | 735 | |
| Ala | Cys | His | Pro | Val | Gln | His | Ser | Lys | Val | Glu | Tyr | Ser | Asp | Thr | Asp |
| | | | 740 | | | | | 745 | | | | | 750 | | |
| Phe | Gln | Ser | Gln | Lys | Ser | Leu | Leu | Tyr | Asp | His | Glu | Asn | Ala | Ser | Thr |
| | | | 755 | | | | | 760 | | | | | 765 | | |
| Leu | Ile | Leu | Thr | Pro | Thr | Ser | Lys | Asp | Val | Leu | Ser | Asn | Leu | Val | Met |
| | | | 770 | | | | | 775 | | | | | 780 | | |
| Ile | Ser | Arg | Gly | Lys | Glu | Ser | Tyr | Lys | Met | Ser | Asp | Lys | Leu | Lys | Gly |
| 785 | | | | | 790 | | | | | 795 | | | | | 800 |
| Asn | Asn | Tyr | Glu | Ser | Asp | Val | Glu | Leu | Thr | Lys | Asn | Ile | Pro | Met | Glu |
| | | | | 805 | | | | | 810 | | | | | 815 | |

```
Lys  Asn  Gln  Asp  Val  Cys  Ala  Leu  Asn  Glu  Asn  Tyr  Lys  Asn  Val  Glu
               820                 825                 830

Leu  Leu  Pro  Pro  Glu  Lys  Tyr  Met  Arg  Val  Ala  Ser  Pro  Ser  Arg  Lys
               835                 840                 845

Val  Gln  Phe  Asn  Gln  Asn  Thr  Asn  Leu  Arg  Val  Ile  Gln  Lys  Asn  Gln
               850                 855                 860

Glu  Glu  Thr  Thr  Ser  Ile  Ser  Lys  Ile  Thr  Val  Asn  Pro  Asp  Ser  Glu
865                      870                 875                           880

Glu  Leu  Phe  Ser  Asp  Asn  Glu  Asn  Asn  Phe  Val  Phe  Gln  Val  Ala  Asn
                    885                 890                      895

Glu  Arg  Asn  Asn  Leu  Ala  Leu  Gly  Asn  Thr  Lys  Glu  Leu  His  Glu  Thr
               900                 905                      910

Asp  Leu  Thr  Cys  Val  Asn  Glu  Pro  Ile  Phe  Lys  Asn  Ser  Thr  Met  Val
               915                 920                 925

Leu  Tyr  Gly  Asp  Thr  Gly  Asp  Lys  Gln  Ala  Thr  Gln  Val  Ser  Ile  Lys
          930                 935                 940

Lys  Asp  Leu  Val  Tyr  Val  Leu  Ala  Glu  Glu  Asn  Lys  Asn  Ser  Val  Lys
945                      950                 955                           960

Gln  His  Ile  Lys  Met  Thr  Leu  Gly  Gln  Asp  Leu  Lys  Ser  Asp  Ile  Ser
                    965                 970                      975

Leu  Asn  Ile  Asp  Lys  Ile  Pro  Glu  Lys  Asn  Asn  Asp  Tyr  Met  Asn  Lys
               980                 985                      990

Trp  Ala  Gly  Leu  Leu  Gly  Pro  Ile  Ser  Asn  His  Ser  Phe  Gly  Gly  Ser
               995                      1000                1005

Phe  Arg  Thr  Ala  Ser  Asn  Lys  Glu  Ile  Lys  Leu  Ser  Glu  His  Asn  Ile
               1010                1015                1020

Lys  Lys  Ser  Lys  Met  Phe  Phe  Lys  Asp  Ile  Glu  Glu  Gln  Tyr  Pro  Thr
1025                     1030                1035                          1040

Ser  Leu  Ala  Cys  Val  Glu  Ile  Val  Asn  Thr  Leu  Ala  Leu  Asp  Asn  Gln
               1045                1050                1055

Lys  Lys  Leu  Ser  Lys  Pro  Gln  Ser  Ile  Asn  Thr  Val  Ser  Ala  His  Leu
               1060                1065                1070

Gln  Ser  Ser  Val  Val  Val  Ser  Asp  Cys  Lys  Asn  Ser  His  Ile  Thr  Pro
               1075                1080                1085

Gln  Met  Leu  Phe  Ser  Lys  Gln  Asp  Phe  Asn  Ser  His  Asn  Leu  Thr
               1090                1095                1100

Pro  Ser  Gln  Lys  Ala  Glu  Ile  Thr  Glu  Leu  Ser  Thr  Ile  Leu  Glu  Glu
1105                     1110                1115                          1120

Ser  Gly  Ser  Gln  Phe  Glu  Phe  Thr  Gln  Phe  Arg  Lys  Pro  Ser  Tyr  Ile
                    1125                1130                     1135

Leu  Gln  Lys  Ser  Thr  Phe  Glu  Val  Pro  Glu  Asn  Gln  Met  Thr  Ile  Leu
               1140                1145                1150

Lys  Thr  Thr  Ser  Glu  Glu  Cys  Arg  Asp  Ala  Asp  Leu  His  Val  Ile  Met
               1155                1160                1165

Asn  Ala  Pro  Ser  Ile  Gly  Gln  Val  Asp  Ser  Ser  Lys  Gln  Phe  Glu  Gly
               1170                1175                1180

Thr  Val  Glu  Ile  Lys  Arg  Lys  Phe  Ala  Gly  Leu  Leu  Lys  Asn  Asp  Cys
1185                     1190                1195                          1200

Asn  Lys  Ser  Ala  Ser  Gly  Tyr  Leu  Thr  Asp  Glu  Asn  Glu  Val  Gly  Phe
               1205                1210                     1215

Arg  Gly  Phe  Tyr  Ser  Ala  His  Gly  Thr  Lys  Leu  Asn  Val  Ser  Thr  Glu
               1220                1225                1230
```

```
Ala  Leu  Gln  Lys  Ala  Val  Lys  Leu  Phe  Ser  Asp  Ile  Glu  Asn  Ile  Ser
          1235                1240                1245

Glu  Glu  Thr  Ser  Ala  Glu  Val  His  Pro  Ile  Ser  Leu  Ser  Ser  Ser  Lys
          1250                1255                1260

Cys  His  Asp  Ser  Val  Val  Ser  Met  Phe  Lys  Ile  Glu  Asn  His  Asn  Asp
1265                1270                1275                     1280

Lys  Thr  Val  Ser  Glu  Lys  Asn  Asn  Lys  Cys  Gln  Leu  Ile  Leu  Gln  Asn
          1285                1290                1295

Asn  Ile  Glu  Met  Thr  Thr  Gly  Thr  Phe  Val  Glu  Glu  Ile  Thr  Glu  Asn
          1300                1305                1310

Tyr  Lys  Arg  Asn  Thr  Glu  Asn  Glu  Asp  Asn  Lys  Tyr  Thr  Ala  Ala  Ser
          1315                1320                1325

Arg  Asn  Ser  His  Asn  Leu  Glu  Phe  Asp  Gly  Ser  Asp  Ser  Ser  Lys  Asn
          1330                1335                1340

Asp  Thr  Val  Cys  Ile  His  Lys  Asp  Glu  Thr  Asp  Leu  Leu  Phe  Thr  Asp
1345                1350                1355                     1360

Gln  His  Asn  Ile  Cys  Leu  Lys  Leu  Ser  Gly  Gln  Phe  Met  Lys  Glu  Gly
                    1365                1370                1375

Asn  Thr  Gln  Ile  Lys  Glu  Asp  Leu  Ser  Asp  Leu  Thr  Phe  Leu  Glu  Val
               1380                1385                1390

Ala  Lys  Ala  Gln  Glu  Ala  Cys  His  Gly  Asn  Thr  Ser  Asn  Lys  Glu  Gln
               1395                1400                1405

Leu  Thr  Ala  Thr  Lys  Thr  Glu  Gln  Asn  Ile  Lys  Asp  Phe  Glu  Thr  Ser
          1410                1415                1420

Asp  Thr  Phe  Phe  Gln  Thr  Ala  Ser  Gly  Lys  Asn  Ile  Ser  Val  Ala  Lys
1425                1430                1435                     1440

Glu  Leu  Phe  Asn  Lys  Ile  Val  Asn  Phe  Phe  Asp  Gln  Lys  Pro  Glu  Glu
                    1445                1450                1455

Leu  His  Asn  Phe  Ser  Leu  Asn  Ser  Glu  Leu  His  Ser  Asp  Ile  Arg  Lys
                    1460                1465                1470

Asn  Lys  Met  Asp  Ile  Leu  Ser  Tyr  Glu  Glu  Thr  Asp  Ile  Val  Lys  His
                    1475                1480                1485

Lys  Ile  Leu  Lys  Glu  Ser  Val  Pro  Val  Gly  Thr  Gly  Asn  Gln  Leu  Val
          1490                1495                1500

Thr  Phe  Gln  Gly  Gln  Pro  Glu  Arg  Asp  Glu  Lys  Ile  Lys  Glu  Pro  Thr
1505                1510                1515                     1520

Leu  Leu  Gly  Phe  His  Thr  Ala  Ser  Gly  Lys  Lys  Val  Lys  Ile  Ala  Lys
                    1525                1530                1535

Glu  Ser  Leu  Asp  Lys  Val  Lys  Asn  Leu  Phe  Asp  Glu  Lys  Glu  Gln  Gly
               1540                1545                1550

Thr  Ser  Glu  Ile  Thr  Ser  Phe  Ser  His  Gln  Trp  Ala  Lys  Thr  Leu  Lys
          1555                1560                1565

Tyr  Arg  Glu  Ala  Cys  Lys  Asp  Leu  Glu  Leu  Ala  Cys  Glu  Thr  Ile  Glu
          1570                1575                1580

Ile  Thr  Ala  Ala  Pro  Lys  Cys  Lys  Glu  Met  Gln  Asn  Ser  Leu  Asn  Asn
1585                1590                1595                     1600

Asp  Lys  Asn  Leu  Val  Ser  Ile  Glu  Thr  Val  Val  Pro  Pro  Lys  Leu  Leu
                    1605                1610                1615

Ser  Asp  Asn  Leu  Cys  Arg  Gln  Thr  Glu  Asn  Leu  Lys  Thr  Ser  Lys  Ser
                    1620                1625                1630

Ile  Phe  Leu  Lys  Val  Lys  Val  His  Glu  Asn  Val  Glu  Lys  Glu  Thr  Ala
               1635                1640                1645

Lys  Ser  Pro  Ala  Thr  Cys  Tyr  Thr  Asn  Gln  Ser  Pro  Tyr  Ser  Val  Ile
          1650                1655                1660
```

```
Glu Asn Ser Ala Leu Ala Phe Tyr Thr Ser Cys Ser Arg Lys Thr Ser
1665                1670                1675                1680

Val Ser Gln Thr Ser Leu Leu Glu Ala Lys Lys Trp Leu Arg Glu Gly
                1685                1690                1695

Ile Phe Asp Gly Gln Pro Glu Arg Ile Asn Thr Ala Asp Tyr Val Gly
                1700                1705                1710

Asn Tyr Leu Tyr Glu Asn Asn Ser Asn Ser Thr Ile Ala Glu Asn Asp
            1715                1720                1725

Lys Asn His Leu Ser Glu Lys Gln Asp Thr Tyr Leu Ser Asn Ser Ser
            1730                1735                1740

Met Ser Asn Ser Tyr Ser Tyr His Ser Asp Glu Val Tyr Asn Asp Ser
1745                1750                1755                1760

Gly Tyr Leu Ser Lys Asn Lys Leu Asp Ser Gly Ile Glu Pro Val Leu
                1765                1770                1775

Lys Asn Val Glu Asp Gln Lys Asn Thr Ser Phe Ser Lys Val Ile Ser
                1780                1785                1790

Asn Val Lys Asp Ala Asn Ala Tyr Pro Gln Thr Val Asn Glu Asp Ile
                1795                1800                1805

Cys Val Glu Glu Leu Val Thr Ser Ser Ser Pro Cys Lys Asn Lys Asn
            1810                1815                1820

Ala Ala Ile Lys Leu Ser Ile Ser Asn Ser Asn Asn Phe Glu Val Gly
1825                1830                1835                1840

Pro Pro Ala Phe Arg Ile Ala Ser Gly Lys Ile Arg Leu Cys Ser His
                1845                1850                1855

Glu Thr Ile Lys Lys Val Lys Asp Ile Phe Thr Asp Ser Phe Ser Lys
                1860                1865                1870

Val Ile Lys Glu Asn Asn Glu Asn Lys Ser Lys Ile Cys Gln Thr Lys
                1875                1880                1885

Ile Met Ala Gly Cys Tyr Glu Ala Leu Asp Asp Ser Glu Asp Ile Leu
                1890                1895                1900

His Asn Ser Leu Asp Asn Asp Glu Cys Ser Met His Ser His Lys Val
1905                1910                1915                1920

Phe Ala Asp Ile Gln Ser Glu Glu Ile Leu Gln His Asn Gln Asn Met
                1925                1930                1935

Ser Gly Leu Glu Lys Val Ser Lys Ile Ser Pro Cys Asp Val Ser Leu
                1940                1945                1950

Glu Thr Ser Asp Ile Cys Lys Cys Ser Ile Gly Lys Leu His Lys Ser
                1955                1960                1965

Val Ser Ser Ala Asn Thr Cys Gly Ile Phe Ser Thr Ala Ser Gly Lys
                1970                1975                1980

Ser Val Gln Val Ser Asp Ala Ser Leu Gln Asn Ala Arg Gln Val Phe
1985                1990                1995                2000

Ser Glu Ile Glu Asp Ser Thr Lys Gln Val Phe Ser Lys Val Leu Phe
                2005                2010                2015

Lys Ser Asn Glu His Ser Asp Gln Leu Thr Arg Glu Glu Asn Thr Ala
                2020                2025                2030

Ile Arg Thr Pro Glu His Leu Ile Ser Gln Lys Gly Phe Ser Tyr Asn
                2035                2040                2045

Val Val Asn Ser Ser Ala Phe Ser Gly Phe Ser Thr Ala Ser Gly Lys
                2050                2055                2060

Gln Val Ser Ile Leu Glu Ser Ser Leu His Lys Val Lys Gly Val Leu
2065                2070                2075                2080
```

```
Glu  Glu  Phe  Asp  Leu  Ile  Arg  Thr  Glu  His  Ser  Leu  His  Tyr  Ser  Pro
               2085                    2090                    2095

Thr  Ser  Arg  Gln  Asn  Val  Ser  Lys  Ile  Leu  Pro  Arg  Val  Asp  Lys  Arg
2100                         2105                    2110

Asn  Pro  Glu  His  Cys  Val  Asn  Ser  Glu  Met  Glu  Lys  Thr  Cys  Ser  Lys
          2115                    2120                         2125

Glu  Phe  Lys  Leu  Ser  Asn  Asn  Leu  Asn  Val  Glu  Gly  Gly  Ser  Ser  Glu
2130                         2135                    2140

Asn  Asn  His  Ser  Ile  Lys  Val  Ser  Pro  Tyr  Leu  Ser  Gln  Phe  Gln  Gln
2145                    2150                    2155                         2160

Asp  Lys  Gln  Gln  Leu  Val  Leu  Gly  Thr  Lys  Val  Ser  Leu  Val  Glu  Asn
               2165                    2170                         2175

Ile  His  Val  Leu  Gly  Lys  Glu  Gln  Ala  Ser  Pro  Lys  Asn  Val  Lys  Met
               2180                    2185                    2190

Glu  Ile  Gly  Lys  Thr  Glu  Thr  Phe  Ser  Asp  Val  Pro  Val  Lys  Thr  Asn
               2195                    2200                    2205

Ile  Glu  Val  Cys  Ser  Thr  Tyr  Ser  Lys  Asp  Ser  Glu  Asn  Tyr  Phe  Glu
          2210                    2215                    2220

Thr  Glu  Ala  Val  Glu  Ile  Ala  Lys  Ala  Phe  Met  Glu  Asp  Asp  Glu  Leu
2225                    2230                    2235                         2240

Thr  Asp  Ser  Lys  Leu  Pro  Ser  His  Ala  Thr  His  Ser  Leu  Phe  Thr  Cys
                    2245                    2250                    2255

Pro  Glu  Asn  Glu  Glu  Met  Val  Leu  Ser  Asn  Ser  Arg  Ile  Gly  Lys  Arg
               2260                    2265                    2270

Arg  Gly  Glu  Pro  Leu  Ile  Leu  Val  Gly  Glu  Pro  Ser  Ile  Lys  Arg  Asn
          2275                    2280                    2285

Leu  Leu  Asn  Glu  Phe  Asp  Arg  Ile  Ile  Glu  Asn  Gln  Glu  Lys  Ser  Leu
2290                         2295                    2300

Lys  Ala  Ser  Lys  Ser  Thr  Pro  Asp  Gly  Thr  Ile  Lys  Asp  Arg  Arg  Leu
2305                    2310                    2315                         2320

Phe  Met  His  His  Val  Ser  Leu  Glu  Pro  Ile  Thr  Cys  Val  Pro  Phe  Arg
                    2325                    2330                    2335

Thr  Thr  Lys  Glu  Arg  Gln  Glu  Ile  Gln  Asn  Pro  Asn  Phe  Thr  Ala  Pro
               2340                    2345                    2350

Gly  Gln  Glu  Phe  Leu  Ser  Lys  Ser  His  Leu  Tyr  Glu  His  Leu  Thr  Leu
          2355                    2360                    2365

Glu  Lys  Ser  Ser  Ser  Asn  Leu  Ala  Val  Ser  Gly  His  Pro  Phe  Tyr  Gln
     2370                    2375                    2380

Val  Ser  Ala  Thr  Arg  Asn  Glu  Lys  Met  Arg  His  Leu  Ile  Thr  Thr  Gly
2385                    2390                    2395                         2400

Arg  Pro  Thr  Lys  Val  Phe  Val  Pro  Pro  Phe  Lys  Thr  Lys  Ser  His  Phe
               2405                    2410                         2415

His  Arg  Val  Glu  Gln  Cys  Val  Arg  Asn  Ile  Asn  Leu  Glu  Glu  Asn  Arg
               2420                    2425                    2430

Gln  Lys  Gln  Asn  Ile  Asp  Gly  His  Gly  Ser  Asp  Asp  Ser  Lys  Asn  Lys
               2435                    2440                    2445

Ile  Asn  Asp  Asn  Glu  Ile  His  Gln  Phe  Asn  Lys  Asn  Asn  Ser  Asn  Gln
          2450                    2455                    2460

Ala  Ala  Ala  Val  Thr  Phe  Thr  Lys  Cys  Glu  Glu  Glu  Pro  Leu  Asp  Leu
2465                    2470                    2475                         2480

Ile  Thr  Ser  Leu  Gln  Asn  Ala  Arg  Asp  Ile  Gln  Asp  Met  Arg  Ile  Lys
                    2485                    2490                    2495

Lys  Lys  Gln  Arg  Gln  Arg  Val  Phe  Pro  Gln  Pro  Gly  Ser  Leu  Tyr  Leu
               2500                    2505                    2510
```

```
Ala Lys Thr Ser Thr Leu Pro Arg Ile Ser Leu Lys Ala Ala Val Gly
        2515                2520                2525
Gly Gln Val Pro Ser Ala Cys Ser His Lys Gln Leu Tyr Thr Tyr Gly
        2530                2535                2540
Val Ser Lys His Cys Ile Lys Ile Asn Ser Lys Asn Ala Glu Ser Phe
2545                2550                2555                2560
Gln Phe His Thr Glu Asp Tyr Phe Gly Lys Glu Ser Leu Trp Thr Gly
        2565                2570                2575
Lys Gly Ile Gln Leu Ala Asp Gly Gly Trp Leu Ile Pro Ser Asn Asp
        2580                2585                2590
Gly Lys Ala Gly Lys Glu Glu Phe Tyr Arg Ala Leu Cys Asp Thr Pro
        2595                2600                2605
Gly Val Asp Pro Lys Leu Ile Ser Arg Ile Trp Val Tyr Asn His Tyr
        2610                2615                2620
Arg Trp Ile Ile Trp Lys Leu Ala Ala Met Glu Cys Ala Phe Pro Lys
2625                2630                2635                2640
Glu Phe Ala Asn Arg Cys Leu Ser Pro Glu Arg Val Leu Leu Gln Leu
        2645                2650                2655
Lys Tyr Arg Tyr Asp Thr Glu Ile Asp Arg Ser Arg Arg Ser Ala Ile
        2660                2665                2670
Lys Lys Ile Met Glu Arg Asp Asp Thr Ala Ala Lys Thr Leu Val Leu
        2675                2680                2685
Cys Val Ser Asp Ile Ile Ser Leu Ser Ala Asn Ile Ser Glu Thr Ser
        2690                2695                2700
Ser Asn Lys Thr Ser Ser Ala Asp Thr Gln Lys Val Ala Ile Ile Glu
2705                2710                2715                2720
Leu Thr Asp Gly Trp Tyr Ala Val Lys Ala Gln Leu Asp Pro Pro Leu
        2725                2730                2735
Leu Ala Val Leu Lys Asn Gly Arg Leu Thr Val Gly Gln Lys Ile Ile
        2740                2745                2750
Leu His Gly Ala Glu Leu Val Gly Ser Pro Asp Ala Cys Thr Pro Leu
        2755                2760                2765
Glu Ala Pro Glu Ser Leu Met Leu Lys Ile Ser Ala Asn Ser Thr Arg
2770                2775                2780
Pro Ala Arg Trp Tyr Thr Lys Leu Gly Phe Phe Pro Asp Pro Arg Pro
2785                2790                2795                2800
Phe Pro Leu Pro Leu Ser Ser Leu Phe Ser Asp Gly Gly Asn Val Gly
        2805                2810                2815
Cys Val Asp Val Ile Ile Gln Arg Ala Tyr Pro Ile Gln Arg Met Glu
        2820                2825                2830
Lys Thr Ser Ser Gly Leu Tyr Ile Phe Arg Asn Glu Arg Glu Glu Glu
        2835                2840                2845
Lys Glu Ala Ala Lys Tyr Val Glu Ala Gln Gln Lys Arg Leu Glu Ala
        2850                2855                2860
Leu Phe Thr Lys Ile Gln Glu Glu Phe Glu Glu His Glu Glu Asn Thr
2865                2870                2875                2880
Thr Lys Pro Tyr Leu Pro Ser Arg Ala Leu Thr Arg Gln Gln Val Arg
        2885                2890                2895
Ala Leu Gln Asp Gly Ala Glu Leu Tyr Glu Ala Val Lys Asn Ala Ala
        2900                2905                2910
Asp Pro Ala Tyr Leu Glu Gly Tyr Phe Ser Glu Glu Gln Leu Arg Ala
        2915                2920                2925
```

```
Leu Asn Asn His Arg Gln Met Leu Asn Asp Lys Lys Gln Ala Gln Ile
    2930                2935                2940

Gln Leu Glu Ile Arg Lys Ala Met Glu Ser Ala Glu Gln Lys Glu Gln
2945                2950                2955                2960

Gly Leu Ser Arg Asp Val Thr Thr Val Trp Leu Arg Ile Val Ser
            2965                2970                2975

Tyr Ser Lys Lys Glu Lys Asp Ser Val Ile Leu Ser Ile Trp Arg Pro
            2980                2985                2990

Ser Ser Asp Leu Tyr Ser Leu Leu Thr Glu Gly Lys Arg Tyr Arg Ile
        2995                3000                3005

Tyr His Leu Ala Thr Ser Lys Ser Lys Ser Lys Ser Glu Arg Ala Asn
        3010                3015                3020

Ile Gln Leu Ala Ala Thr Lys Lys Thr Gln Tyr Gln Gln Leu Pro Val
3025                3030                3035                3040

Ser Asp Glu Ile Leu Phe Gln Ile Tyr Gln Pro Arg Glu Pro Leu His
            3045                3050                3055

Phe Ser Lys Phe Leu Asp Pro Asp Phe Gln Pro Ser Cys Ser Glu Val
            3060                3065                3070

Asp Leu Ile Gly Phe Val Val Ser Val Val Lys Lys Thr Gly Leu Ala
        3075                3080                3085

Pro Phe Val Tyr Leu Ser Asp Glu Cys Tyr Asn Leu Leu Ala Ile Lys
3090                3095                3100

Phe Trp Ile Asp Leu Asn Glu Asp Ile Ile Lys Pro His Met Leu Ile
3105                3110                3115                3120

Ala Ala Ser Asn Leu Gln Trp Arg Pro Glu Ser Lys Ser Gly Leu Leu
            3125                3130                3135

Thr Leu Phe Ala Gly Asp Phe Ser Val Phe Ser Ala Ser Pro Lys Glu
            3140                3145                3150

Gly His Phe Gln Glu Thr Phe Asn Lys Met Lys Asn Thr Val Glu Asn
        3155                3160                3165

Ile Asp Ile Leu Cys Asn Glu Ala Glu Asn Lys Leu Met His Ile Leu
        3170                3175                3180

His Ala Asn Asp Pro Lys Trp Ser Thr Pro Thr Lys Asp Cys Thr Ser
3185                3190                3195                3200

Gly Pro Tyr Thr Ala Gln Ile Ile Pro Gly Thr Gly Asn Lys Leu Leu
            3205                3210                3215

Met Ser Ser Pro Asn Cys Glu Ile Tyr Tyr Gln Ser Pro Leu Ser Leu
            3220                3225                3230

Cys Met Ala Lys Arg Lys Ser Val Ser Thr Pro Val Ser Ala Gln Met
            3235                3240                3245

Thr Ser Lys Ser Cys Lys Gly Glu Lys Glu Ile Asp Asp Gln Lys Asn
    3250                3255                3260

Cys Lys Lys Arg Arg Ala Leu Asp Phe Leu Ser Arg Leu Pro Leu Pro
3265                3270                3275                3280

Pro Pro Val Ser Pro Ile Cys Thr Phe Val Ser Pro Ala Ala Gln Lys
            3285                3290                3295

Ala Phe Gln Pro Pro Arg Ser Cys Gly Thr Lys Tyr Glu Thr Pro Ile
            3300                3305                3310

Lys Lys Lys Glu Leu Asn Ser Pro Gln Met Thr Pro Phe Lys Lys Phe
        3315                3320                3325

Asn Glu Ile Ser Leu Leu Glu Ser Asn Ser Ile Ala Asp Glu Glu Leu
    3330                3335                3340

Ala Leu Ile Asn Thr Gln Ala Leu Leu Ser Gly Ser Thr Gly Glu Lys
3345                3350                3355                3360
```

Gln Phe Ile Ser Val Ser Glu Ser Thr Arg Thr Ala Pro Thr Ser Ser
                3365            3370                    3375

Glu Asp Tyr Leu Arg Leu Lys Arg Arg Cys Thr Thr Ser Leu Ile Lys
            3380            3385                    3390

Glu Gln Glu Ser Ser Gln Ala Ser Thr Glu Glu Cys Glu Lys Asn Lys
            3395            3400            3405

Gln Asp Thr Ile Thr Thr Lys Lys Tyr Ile
    3410                3415

( 2 ) INFORMATION FOR SEQ ID NO:5:

( i ) SEQUENCE CHARACTERISTICS:
        ( A ) LENGTH:19
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
        ( A ) ORGANISM: Homo sapiens sapiens
        ( C ) INDIVIDUAL ISOLATE:
        ( D ) DEVELOPMENTAL STAGE: adult
        ( F ) TISSUE TYPE: female breast
        ( G ) CELL TYPE: normal breast tissue
        ( H ) CELL LINE: HMEC
        ( I ) ORGANELLE: no ( i x ) FEATURE:
        ( A ) NAME/KEY: BRCA1 C-19 antigen
        ( B ) LOCATION: 1845 to 1863
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) PAGES:
        ( F ) DATE:
        ( K ) RELEVANT RESIDUES IN SEQ ID NO:5

( x i ) SEQUENCE DESCRIPTION: SEQ ID NO:5:

Tyr Gln Cys Gln Glu Leu Asp Thr Tyr Leu Ile Pro Gln Ile Pro His
1                5                    10                  15

Ser His Tyr ( 2 ) INFORMATION FOR SEQ ID NO:6:

( i ) SEQUENCE CHARACTERISTICS:
        ( A ) LENGTH: 20
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
        ( A ) ORGANISM: Homo sapiens sapiens
        ( C ) INDIVIDUAL ISOLATE:
        ( D ) DEVELOPMENTAL STAGE: adult
        ( F ) TISSUE TYPE: female breast
        ( G ) CELL TYPE: normal breast tissue (H) CELL LINE: HMEC
                    (I) ORGANELLE: no (ix) FEATURE:
                    (A) NAME/KEY: BRCA1 C-20 antigen
                    (B) LOCATION: 1844 to 1863
                    (C) IDENTIFICATION METHOD:
                    (D) OTHER INFORMATION:

(x) PUBLICATION INFORMATION:
                    (A) AUTHORS:
                    (B) TITLE:
                    (C) JOURNAL:
                    (D) VOLUME:
                    (E) PAGES:
                    (F) DATE:
                    (K) RELEVANT RESIDUES IN SEQ ID NO:6

(xi) SEQUENCE DESCRIPTION: SEQ ID NO:6:

Leu Tyr Gln Cys Gln Glu Leu Asp Thr Tyr Leu Ile Pro Gln Ile Pro
1               5                   10                  15
His Ser His Tyr
            20

(2) INFORMATION FOR SEQ ID NO:7:

(i) SEQUENCE CHARACTERISTICS:
                    (A) LENGTH: 20
                    (B) TYPE: amino acid
                    (C) STRANDEDNESS: single
                    (D) TOPOLOGY: unknown (ii) MOLECULE TYPE: peptide (iii) HYPOTHETICAL: no (iv) ANTI-SENSE: no (v) ORIGINAL SOURCE:
                    (A) ORGANISM: Homo sapiens sapiens
                    (C) INDIVIDUAL ISOLATE:
                    (D) DEVELOPMENTAL STAGE: adult
                    (F) TISSUE TYPE: female breast
                    (G) CELL TYPE: normal breast tissue
                    (H) CELL LINE: HMEC
                    (I) ORGANELLE: no (ix) FEATURE:
                    (A) NAME/KEY: BRCA1 D-20 antigen
                    (B) LOCATION: 1 to 20
                    (C) IDENTIFICATION METHOD:
                    (D) OTHER INFORMATION:

(x) PUBLICATION INFORMATION:
                    (A) AUTHORS:
                    (B) TITLE:
                    (C) JOURNAL:
                    (D) VOLUME:
                    (E) PAGES:
                    (F) DATE:
                    (K) RELEVANT RESIDUES IN SEQ ID NO:7

(xi) SEQUENCE DESCRIPTION: SEQ ID NO:7:

Met Asp Leu Ser Ala Leu Arg Val Glu Glu Val Gln Asn Val Ile Asn
1               5                   10                  15
Ala Met Gln Lys
            20

(2) INFORMATION FOR SEQ ID NO:8:

(i) SEQUENCE CHARACTERISTICS:
                    (A) LENGTH: 10
                    (B) TYPE: amino acid
                    (C) STRANDEDNESS: single (D) TOPOLOGY: unknown (ii) MOLECULE TYPE: peptide (iii) HYPOTHETICAL:

(iv) ANTI-SENSE: no (v) ORIGINAL SOURCE:
              (A) ORGANISM:
              (C) INDIVIDUAL ISOLATE:
              (D) DEVELOPMENTAL STAGE:
              (F) TISSUE TYPE:
              (G) CELL TYPE:
              (H) CELL LINE:
              (I) ORGANELLE:

(ix) FEATURE:
              (A) NAME/KEY: Granin Consensus Sequence
              (B) LOCATION:
              (C) IDENTIFICATION METHOD:
              (D) OTHER INFORMATION:

(x) PUBLICATION INFORMATION:
              (A) AUTHORS:
              (B) TITLE:
              (C) JOURNAL:
              (D) VOLUME:
              (E) PAGES:
              (F) DATE:
              (K) RELEVANT RESIDUES IN SEQ ID NO:8:

(xi) SEQUENCE DESCRIPTION: SEQ ID NO:8:

Glu  Asn  Leu  Ser  Xaa  Xaa  Asp  Xaa  Glu  Leu
1                 5                          10

(2) INFORMATION FOR SEQ ID NO:9:

(i) SEQUENCE CHARACTERISTICS:
              (A) LENGTH: 10
              (B) TYPE: amino acid
              (C) STRANDEDNESS: single
              (D) TOPOLOGY: unknown (ii) MOLECULE TYPE: peptide (iii) HYPOTHETICAL: no (iv) ANTI-SENSE: no (v) ORIGINAL SOURCE:
              (A) ORGANISM: Human
              (C) INDIVIDUAL ISOLATE:
              (D) DEVELOPMENTAL STAGE:
              (F) TISSUE TYPE:
              (G) CELL TYPE:
              (H) CELL LINE:
              (I) ORGANELLE:

(ix) FEATURE:
              (A) NAME/KEY: BRCA1 Granin Sequence
              (B) LOCATION: amino acids 1214-1223 of BRCA1 protein
              (C) IDENTIFICATION METHOD:
              (D) OTHER INFORMATION:

(x) PUBLICATION INFORMATION:
              (A) AUTHORS:
              (B) TITLE:
              (C) JOURNAL:
              (D) VOLUME:
              (E) PAGES:
              (F) DATE:
              (K) RELEVANT RESIDUES IN SEQ ID NO:9:

(xi) SEQUENCE DESCRIPTION: SEQ ID NO:9:

Glu  Asn  Leu  Ser  Ser  Glu  Asp  Glu  Glu  Leu
1                 5                          10

( 2 ) INFORMATION FOR SEQ ID NO:10:

( i ) SEQUENCE CHARACTERISTICS:
        ( A ) LENGTH: 10
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
        ( A ) ORGANISM: Rhesus
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: BRCA1 Granin Sequence
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) PAGES:
        ( F ) DATE:
        ( K ) RELEVANT RESIDUES IN SEQ ID NO:10:

( x i ) SEQUENCE DESCRIPTION: SEQ ID NO:10:

```
Glu  Asn  Leu  Ser  Ser  Glu  Asp  Glu  Glu  Leu
1                   5                        10
```

( 2 ) INFORMATION FOR SEQ ID NO:11:

( i ) SEQUENCE CHARACTERISTICS:
        ( A ) LENGTH: 10
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
        ( A ) ORGANISM: Mouse
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: BRCA1 Granin Sequence
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:

( E ) PAGES:
( F ) DATE:
( K ) RELEVANT RESIDUES IN SEQ ID NO:11:

( x i ) SEQUENCE DESCRIPTION: SEQ ID NO:11:

| Glu | Ser | Asp | Ser | Thr | Glu | Asp | Glu | Asp | Leu |
|---|---|---|---|---|---|---|---|---|---|
| 1 | | | | 5 | | | | | 10 |

( 2 ) INFORMATION FOR SEQ ID NO:12:

( i ) SEQUENCE CHARACTERISTICS:
        ( A ) LENGTH: 10
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
        ( A ) ORGANISM: Human
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: BRCA2 Granin Sequence
        ( B ) LOCATION: amino acids 3334-3344 of BRCA2 protein
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) PAGES:
        ( F ) DATE:
        ( K ) RELEVANT RESIDUES IN SEQ ID NO:12:

( x i ) SEQUENCE DESCRIPTION: SEQ ID NO:12:

| Glu | Ser | Asn | Ser | Ile | Ala | Asp | Glu | Glu | Leu |
|---|---|---|---|---|---|---|---|---|---|
| 1 | | | | 5 | | | | | 10 |

( 2 ) INFORMATION FOR SEQ ID NO:13:

( i ) SEQUENCE CHARACTERISTICS:
        ( A ) LENGTH: 10
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
        ( A ) ORGANISM: Human
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: Chromogranin A Granin Sequence
        ( B ) LOCATION:

( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) PAGES:
                    ( F ) DATE:
                    ( K ) RELEVANT RESIDUES IN SEQ ID NO:13:

( x i ) SEQUENCE DESCRIPTION: SEQ ID NO:13:

Glu  Ser  Leu  Ser  Ala  Ile  Glu  Ala  Glu  Leu
1                   5                        1 0

( 2 ) INFORMATION FOR SEQ ID NO:14:

( i ) SEQUENCE CHARACTERISTICS:
                    ( A ) LENGTH: 10
                    ( B ) TYPE: amino acid
                    ( C ) STRANDEDNESS: single
                    ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
                    ( A ) ORGANISM: Bovine
                    ( C ) INDIVIDUAL ISOLATE:
                    ( D ) DEVELOPMENTAL STAGE:
                    ( F ) TISSUE TYPE:
                    ( G ) CELL TYPE:
                    ( H ) CELL LINE:
                    ( I ) ORGANELLE:

( i x ) FEATURE:
                    ( A ) NAME/KEY: Chromogranin A Granin Sequence
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) PAGES:
                    ( F ) DATE:
                    ( K ) RELEVANT RESIDUES IN SEQ ID NO:14:

( x i ) SEQUENCE DESCRIPTION: SEQ ID NO:14:

Glu  Ser  Leu  Ser  Ala  Ile  Glu  Ala  Glu  Leu
1                   5                        1 0

( 2 ) INFORMATION FOR SEQ ID NO:15:

( i ) SEQUENCE CHARACTERISTICS:
                    ( A ) LENGTH: 10
                    ( B ) TYPE: amino acid
                    ( C ) STRANDEDNESS: single
                    ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
                    ( A ) ORGANISM: Rat
                    ( C ) INDIVIDUAL ISOLATE:
                    ( D ) DEVELOPMENTAL STAGE:

(F) TISSUE TYPE:
(G) CELL TYPE:
(H) CELL LINE:
(I) ORGANELLE:

(ix) FEATURE:
(A) NAME/KEY: Chromogranin A Granin Sequence
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) PAGES:
(F) DATE:
(K) RELEVANT RESIDUES IN SEQ ID NO:15:

(xi) SEQUENCE DESCRIPTION: SEQ ID NO:15:

```
Glu  Ser  Leu  Ser  Ala  Ile  Glu  Ala  Glu  Leu
1                  5                        10
```

(2) INFORMATION FOR SEQ ID NO:16:

(i) SEQUENCE CHARACTERISTICS:
(A) LENGTH: 10
(B) TYPE: amino acid
(C) STRANDEDNESS: single
(D) TOPOLOGY: unknown (ii) MOLECULE TYPE: peptide (iii) HYPOTHETICAL: no (iv) ANTI-SENSE: no (v) ORIGINAL SOURCE:
(A) ORGANISM: Pig
(C) INDIVIDUAL ISOLATE:
(D) DEVELOPMENTAL STAGE:
(F) TISSUE TYPE:
(G) CELL TYPE:
(H) CELL LINE:
(I) ORGANELLE:

(ix) FEATURE:
(A) NAME/KEY: Chromogranin A Granin Sequence
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) PAGES:
(F) DATE:
(K) RELEVANT RESIDUES IN SEQ ID NO:16:

(xi) SEQUENCE DESCRIPTION: SEQ ID NO:16:

```
Glu  Ser  Leu  Ser  Ala  Ile  Glu  Ala  Glu  Leu
1                  5                        10
```

(2) INFORMATION FOR SEQ ID NO:17:

(i) SEQUENCE CHARACTERISTICS:
(A) LENGTH: 10
(B) TYPE: amino acid
(C) STRANDEDNESS: single
(D) TOPOLOGY: unknown (ii) MOLECULE TYPE: peptide ( i i i ) HYPOTHETICAL: no ( i v ) ANTI-SENSE: no ( v ) ORIGINAL SOURCE:
    ( A ) ORGANISM: Human
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:
    ( I ) ORGANELLE:

( i x ) FEATURE:
    ( A ) NAME/KEY: Chromogranin B Granin Sequence
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) PAGES:
    ( F ) DATE:
    ( K ) RELEVANT RESIDUES IN SEQ ID NO:17:

( x i ) SEQUENCE DESCRIPTION: SEQ ID NO:17:

```
Glu Asn Leu Ala Ala Met Asp Leu Glu Leu
1               5                   10
```

( 2 ) INFORMATION FOR SEQ ID NO:18:

( i ) SEQUENCE CHARACTERISTICS:
    ( A ) LENGTH: 10
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
    ( A ) ORGANISM: Bovine
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:
    ( I ) ORGANELLE:

( i x ) FEATURE:
    ( A ) NAME/KEY: Chromogranin B Granin Sequence
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) PAGES:
    ( F ) DATE:
    ( K ) RELEVANT RESIDUES IN SEQ ID NO:18:

( x i ) SEQUENCE DESCRIPTION: SEQ ID NO:18:

```
Glu Asn Leu Ala Ala Met Asp Leu Glu Leu
1               5                   10
```

( 2 ) INFORMATION FOR SEQ ID NO:19:

( i ) SEQUENCE CHARACTERISTICS:

(A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no (iv) ANTI-SENSE: no (v) ORIGINAL SOURCE:
            (A) ORGANISM: Mouse
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: Chromogranin B Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:19:

(xi) SEQUENCE DESCRIPTION: SEQ ID NO:19:

```
Glu Asn Leu Ala Ala Met Asp Leu Glu Leu
1               5                   10
```

(2) INFORMATION FOR SEQ ID NO:20:

(i) SEQUENCE CHARACTERISTICS:
            (A) LENGTH: 10
            (B) TYPE: amino acid
            (C) STRANDEDNESS: single
            (D) TOPOLOGY: unknown (ii) MOLECULE TYPE: peptide (iii) HYPOTHETICAL: no (iv) ANTI-SENSE: no (v) ORIGINAL SOURCE:
            (A) ORGANISM: Human
            (C) INDIVIDUAL ISOLATE:
            (D) DEVELOPMENTAL STAGE:
            (F) TISSUE TYPE:
            (G) CELL TYPE:
            (H) CELL LINE:
            (I) ORGANELLE:

(ix) FEATURE:
            (A) NAME/KEY: Secretogranin II Granin Sequence
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) PAGES:
            (F) DATE:
            (K) RELEVANT RESIDUES IN SEQ ID NO:20:

(xi) SEQUENCE DESCRIPTION: SEQ ID NO:20:

```
Glu  Asn  Leu  Asn  Asp  Lys  Asp  Gln  Glu  Leu
1                   5                        10
```

( 2 ) INFORMATION FOR SEQ ID NO:21:

( i ) SEQUENCE CHARACTERISTICS:
        ( A ) LENGTH: 10
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
        ( A ) ORGANISM: Bovine
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: Secretogranin II Granin Sequence
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) PAGES:
        ( F ) DATE:
        ( K ) RELEVANT RESIDUES IN SEQ ID NO:21:

( x i ) SEQUENCE DESCRIPTION: SEQ ID NO:21:

```
Glu  Asn  Leu  Asn  Asp  Lys  Asp  Gln  Glu  Leu
1                   5                        10
```

( 2 ) INFORMATION FOR SEQ ID NO:22:

( i ) SEQUENCE CHARACTERISTICS:
        ( A ) LENGTH: 10
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
        ( A ) ORGANISM: Rat
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:
        ( I ) ORGANELLE:

( i x ) FEATURE:
        ( A ) NAME/KEY: Secretogranin II Granin Sequence
        ( B ) LOCATION:
        ( C ) IDENTIFICATION METHOD:
        ( D ) OTHER INFORMATION:

( x ) PUBLICATION INFORMATION:
        ( A ) AUTHORS:

(B) TITLE:
(C) JOURNAL:
(D) VOLUME:
(E) PAGES:
(F) DATE:
(K) RELEVANT RESIDUES IN SEQ ID NO:22:

(xi) SEQUENCE DESCRIPTION: SEQ ID NO:22:

```
Asp Asn Leu Asn Asp Lys Asp Gln Glu Leu
1               5                   10
```

(2) INFORMATION FOR SEQ ID NO:23:

(i) SEQUENCE CHARACTERISTICS:
        (A) LENGTH: 10
        (B) TYPE: amino acid
        (C) STRANDEDNESS: single
        (D) TOPOLOGY: unknown (ii) MOLECULE TYPE: peptide (iii) HYPOTHETICAL: no (iv) ANTI-SENSE: no (v) ORIGINAL SOURCE:
        (A) ORGANISM: Mouse
        (C) INDIVIDUAL ISOLATE:
        (D) DEVELOPMENTAL STAGE:
        (F) TISSUE TYPE:
        (G) CELL TYPE:
        (H) CELL LINE:
        (I) ORGANELLE:

(ix) FEATURE:
        (A) NAME/KEY: Secretogranin II Granin Sequence
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) PAGES:
        (F) DATE:
        (K) RELEVANT RESIDUES IN SEQ ID NO:23:

(xi) SEQUENCE DESCRIPTION: SEQ ID NO:23:

```
Glu Asn Leu Asn Xaa Xaa Asp Gln Glu Leu
1               5                   10
```

(2) INFORMATION FOR SEQ ID NO:24:

(i) SEQUENCE CHARACTERISTICS:
        (A) LENGTH: 10
        (B) TYPE: amino acid
        (C) STRANDEDNESS: single
        (D) TOPOLOGY: unknown (ii) MOLECULE TYPE: peptide (iii) HYPOTHETICAL: no (iv) ANTI-SENSE: no (v) ORIGINAL SOURCE:
        (A) ORGANISM: Rat
        (C) INDIVIDUAL ISOLATE:
        (D) DEVELOPMENTAL STAGE:
        (F) TISSUE TYPE:
        (G) CELL TYPE:
        (H) CELL LINE:
        (I) ORGANELLE:

( i x ) FEATURE:
  ( A ) NAME/KEY: Secretogranin III Granin Sequence
  ( B ) LOCATION:
  ( C ) IDENTIFICATION METHOD:
  ( D ) OTHER INFORMATION:

( x ) PUBLICATION INFORMATION:
  ( A ) AUTHORS:
  ( B ) TITLE:
  ( C ) JOURNAL:
  ( D ) VOLUME:
  ( E ) PAGES:
  ( F ) DATE:
  ( K ) RELEVANT RESIDUES IN SEQ ID NO:24:

( x i ) SEQUENCE DESCRIPTION: SEQ ID NO:24:

```
Glu Asn Leu Asp Glu Thr Ile Ala Leu Gln
1               5                   10
```

( 2 ) INFORMATION FOR SEQ ID NO:25:

( i ) SEQUENCE CHARACTERISTICS:
    ( A ) LENGTH: 10
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:
    ( A ) ORGANISM: Mouse
    ( C ) INDIVIDUAL ISOLATE:
    ( D ) DEVELOPMENTAL STAGE:
    ( F ) TISSUE TYPE:
    ( G ) CELL TYPE:
    ( H ) CELL LINE:
    ( I ) ORGANELLE:

( i x ) FEATURE:
    ( A ) NAME/KEY: Secretogranin III Granin Sequence
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) PAGES:
    ( F ) DATE:
    ( K ) RELEVANT RESIDUES IN SEQ ID NO:25:

( x i ) SEQUENCE DESCRIPTION: SEQ ID NO:25:

```
Glu Asn Leu Asp Glu Thr Ile Ala Leu Gln
1               5                   10
```

( 2 ) INFORMATION FOR SEQ ID NO:26:

( i ) SEQUENCE CHARACTERISTICS:
    ( A ) LENGTH: 10
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: no ( i v ) ANTI-SENSE: no ( v ) ORIGINAL SOURCE:

(A) ORGANISM: Human
                (C) INDIVIDUAL ISOLATE:
                (D) DEVELOPMENTAL STAGE:
                (F) TISSUE TYPE:
                (G) CELL TYPE:
                (H) CELL LINE:
                (I) ORGANELLE:

(ix) FEATURE:
                (A) NAME/KEY: Secretogranin V Granin Sequence
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) PAGES:
                (F) DATE:
                (K) RELEVANT RESIDUES IN SEQ ID NO:26:

(xi) SEQUENCE DESCRIPTION: SEQ ID NO:26:

Gly Asn Ile Pro Asn Ile Val Ala Glu Leu
1               5                   10

(2) INFORMATION FOR SEQ ID NO:27:

(i) SEQUENCE CHARACTERISTICS:
                (A) LENGTH: 10
                (B) TYPE: amino acid
                (C) STRANDEDNESS: single
                (D) TOPOLOGY: unknown (ii) MOLECULE TYPE: peptide (iii) HYPOTHETICAL: no (iv) ANTI-SENSE: no (v) ORIGINAL SOURCE:
                (A) ORGANISM: Pig
                (C) INDIVIDUAL ISOLATE:
                (D) DEVELOPMENTAL STAGE:
                (F) TISSUE TYPE:
                (G) CELL TYPE:
                (H) CELL LINE:
                (I) ORGANELLE:

(ix) FEATURE:
                (A) NAME/KEY: Secretogranin V Granin Sequence
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) PAGES:
                (F) DATE:
                (K) RELEVANT RESIDUES IN SEQ ID NO:27:

(xi) SEQUENCE DESCRIPTION: SEQ ID NO:27:

Gly Asn Ile Pro Asn Ile Val Ala Glu Leu
1               5                   10

(2) INFORMATION FOR SEQ ID NO:28:

(i) SEQUENCE CHARACTERISTICS:
                (A) LENGTH: 10
                (B) TYPE: amino acid
                (C) STRANDEDNESS: single
                (D) TOPOLOGY: unknown (ii) MOLECULE TYPE: peptide (iii) HYPOTHETICAL: no (iv) ANTI-SENSE: no (v) ORIGINAL SOURCE:
(A) ORGANISM: Rat
(C) INDIVIDUAL ISOLATE:
(D) DEVELOPMENTAL STAGE:
(F) TISSUE TYPE:
(G) CELL TYPE:
(H) CELL LINE:
(I) ORGANELLE:

(ix) FEATURE:
(A) NAME/KEY: Secretogranin V Granin Sequence
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) PAGES:
(F) DATE:
(K) RELEVANT RESIDUES IN SEQ ID NO:28:

(xi) SEQUENCE DESCRIPTION: SEQ ID NO:28:

Gly Asn Ile Pro Asn Ile Val Ala Glu Leu
1               5                   10

(2) INFORMATION FOR SEQ ID NO:29:

(i) SEQUENCE CHARACTERISTICS:
(A) LENGTH: 10
(B) TYPE: amino acid
(C) STRANDEDNESS: single
(D) TOPOLOGY: unknown (ii) MOLECULE TYPE: peptide (iii) HYPOTHETICAL: no (iv) ANTI-SENSE: no (v) ORIGINAL SOURCE:
(A) ORGANISM: Xenopus
(C) INDIVIDUAL ISOLATE:
(D) DEVELOPMENTAL STAGE:
(F) TISSUE TYPE:
(G) CELL TYPE:
(H) CELL LINE:
(I) ORGANELLE:

(ix) FEATURE:
(A) NAME/KEY: Secretogranin V Granin Sequence
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) PAGES:
(F) DATE:
(K) RELEVANT RESIDUES IN SEQ ID NO:29:

(xi) SEQUENCE DESCRIPTION: SEQ ID NO:29:

Gly Asn Ile Pro Asn Ile Val Ala Glu Leu
1               5                   10